(12) United States Patent
Fening et al.

(10) Patent No.: US 10,675,064 B2
(45) Date of Patent: Jun. 9, 2020

(54) DISTRACTION OSTEOGENESIS SYSTEM

(71) Applicants: Children's Hospital Medical Center of Akron, Akron, OH (US); Austen BioInnovation Institute In Akron, Akron, OH (US)

(72) Inventors: Stephen D. Fening, Brecksville, OH (US); Todd Ritzman, Akron, OH (US); John F. Zak, Chagrin Falls, OH (US)

(73) Assignees: CHILDREN'S HOSPITAL MEDICAL CENTER OF AKRON, Akron, OH (US); AUSTEN BIOINNOVATION INSTITUTE IN AKRON, Akron, OH (US)

( * ) Notice: Subject to any disclaimer, the term of this patent is extended or adjusted under 35 U.S.C. 154(b) by 0 days.

(21) Appl. No.: 15/808,454

(22) Filed: Nov. 9, 2017

(65) Prior Publication Data

US 2018/0132900 A1 May 17, 2018

Related U.S. Application Data

(63) Continuation-in-part of application No. 14/303,169, filed on Jun. 12, 2014, now Pat. No. 10,016,226,
(Continued)

(51) Int. Cl.
*A61B 17/72* (2006.01)
*A61B 17/70* (2006.01)
(Continued)

(52) U.S. Cl.
CPC ........ *A61B 17/7016* (2013.01); *A61B 17/707* (2013.01); *A61B 17/7216* (2013.01);
(Continued)

(58) Field of Classification Search
CPC ...... A61B 17/72–7291; Y10T 403/7005–7011
See application file for complete search history.

(56) References Cited

U.S. PATENT DOCUMENTS

RE24,066 E   9/1948  Brown
5,575,790 A  11/1996 Chen et al.
(Continued)

FOREIGN PATENT DOCUMENTS

CN   101466321 A   6/2009
DE   198 07 663 A1  9/1999
(Continued)

OTHER PUBLICATIONS

PCT Written Opinion of the International Searching Authority and International Search Report, International Application PCT/US2017/060908, dated Jun. 26, 2018, 14 pages.
(Continued)

*Primary Examiner* — Nicholas J Plionis
*Assistant Examiner* — Steven J Cotroneo
(74) *Attorney, Agent, or Firm* — Tucker Ellis LLP; Heather M. Barnes; Michael G. Craig

(57) ABSTRACT

One or more techniques and/or systems are disclosed for a system for distraction osteogenesis of long bones. Selectively adjustable drive magnets disposed in the system can be used to distract the device. An external drive device generating a magnetic field may be used to rotate the drive in externally.

20 Claims, 52 Drawing Sheets

Related U.S. Application Data which is a continuation-in-part of application No. 13/712,387, filed on Dec. 12, 2012.

(60) Provisional application No. 62/419,732, filed on Nov. 9, 2016, provisional application No. 61/569,453, filed on Dec. 12, 2011, provisional application No. 61/585,450, filed on Jan. 11, 2012.

(51) Int. Cl.
- *A61B 17/68* (2006.01)
- *A61B 17/00* (2006.01)
- *A61B 17/80* (2006.01)
- *A61B 17/84* (2006.01)

(52) U.S. Cl.
CPC ......... *A61B 17/8019* (2013.01); *A61B 17/844* (2013.01); *A61B 2017/00199* (2013.01); *A61B 2017/00221* (2013.01); *A61B 2017/00398* (2013.01); *A61B 2017/00411* (2013.01); *A61B 2017/00477* (2013.01); *A61B 2017/00876* (2013.01); *A61B 2017/681* (2013.01)

(56) References Cited

U.S. PATENT DOCUMENTS

| | | | |
|---|---|---|---|
| 5,704,939 A | 1/1998 | Justin | |
| 6,004,349 A | 12/1999 | Jackson | |
| 6,033,412 A * | 3/2000 | Losken | A61B 17/663 606/105 |
| 6,336,929 B1 * | 1/2002 | Justin | A61B 17/7216 606/63 |
| 6,514,255 B1 | 2/2003 | Ferree | |
| 6,849,076 B2 | 2/2005 | Blunn et al. | |
| 7,650,888 B2 | 1/2010 | Maschke | |
| 7,753,915 B1 * | 7/2010 | Eksler | A61B 17/663 606/105 |
| 7,763,053 B2 | 7/2010 | Gordon | |
| 7,862,502 B2 | 1/2011 | Pool et al. | |
| 7,955,357 B2 | 6/2011 | Kiester | |
| 7,963,978 B2 | 6/2011 | Winslow et al. | |
| 7,981,025 B2 | 7/2011 | Pool et al. | |
| 8,016,837 B2 | 9/2011 | Giger | |
| 8,057,472 B2 | 11/2011 | Walker et al. | |
| 8,197,490 B2 | 6/2012 | Pool et al. | |
| 8,240,942 B2 | 8/2012 | Baur et al. | |
| 8,343,192 B2 | 1/2013 | Kiester | |
| 8,382,756 B2 | 2/2013 | Pool et al. | |
| 8,419,734 B2 | 4/2013 | Walker et al. | |
| 8,529,609 B2 | 9/2013 | Helgerson et al. | |
| 8,568,457 B2 | 10/2013 | Hunziker | |
| 8,632,548 B2 | 1/2014 | Souberian | |
| 8,852,236 B2 | 10/2014 | Kiester | |
| 9,011,499 B1 | 4/2015 | Kiester | |
| 9,668,773 B2 | 6/2017 | Alexander et al. | |
| 2004/0030395 A1 | 2/2004 | Blunn et al. | |
| 2004/0236329 A1 | 11/2004 | Panjabi | |
| 2004/0254575 A1 | 12/2004 | Obenchain et al. | |
| 2005/0090827 A1 | 4/2005 | Gedebou | |
| 2006/0047282 A1 | 3/2006 | Gordon | |
| 2006/0058792 A1 | 3/2006 | Hynes | |
| 2006/0074448 A1 | 4/2006 | Harrison et al. | |
| 2006/0079897 A1 | 4/2006 | Harrison et al. | |
| 2006/0229615 A1 | 10/2006 | Abdou | |
| 2007/0233098 A1 | 10/2007 | Mastrorio et al. | |
| 2007/0270803 A1 * | 11/2007 | Giger | A61B 17/8076 606/60 |
| 2007/0276378 A1 | 11/2007 | Harrison et al. | |
| 2008/0027436 A1 | 1/2008 | Cournoyer et al. | |
| 2008/0033436 A1 | 2/2008 | Song et al. | |
| 2009/0005821 A1 | 1/2009 | Chirico et al. | |
| 2009/0012565 A1 | 1/2009 | Sach et al. | |
| 2009/0082815 A1 | 3/2009 | Zylber et al. | |
| 2009/0112207 A1 | 4/2009 | Walker et al. | |
| 2009/0112262 A1 | 4/2009 | Pool et al. | |
| 2009/0112263 A1 | 4/2009 | Pool et al. | |
| 2009/0198273 A1 | 8/2009 | Zhang et al. | |
| 2009/0198279 A1 | 8/2009 | Zhang et al. | |
| 2009/0204154 A1 | 8/2009 | Kiester | |
| 2009/0254088 A1 * | 10/2009 | Soubeiran | A61B 17/7216 606/63 |
| 2010/0049204 A1 | 2/2010 | Soubeiran | |
| 2010/0094303 A1 | 4/2010 | Chang et al. | |
| 2010/0094306 A1 | 4/2010 | Chang et al. | |
| 2010/0111599 A1 | 5/2010 | Baur et al. | |
| 2010/0114103 A1 | 5/2010 | Harrison et al. | |
| 2010/0121323 A1 | 5/2010 | Pool et al. | |
| 2010/0137911 A1 | 6/2010 | Dant | |
| 2010/0217271 A1 | 8/2010 | Pool et al. | |
| 2010/0280551 A1 | 11/2010 | Pool | |
| 2011/0060336 A1 * | 3/2011 | Pool | A61B 17/1725 606/57 |
| 2011/0137347 A1 | 6/2011 | Hunziker | |
| 2011/0230883 A1 * | 9/2011 | Zahrly | A61B 17/7216 606/63 |
| 2012/0035656 A1 | 2/2012 | Pool et al. | |
| 2012/0035661 A1 | 2/2012 | Pool et al. | |
| 2012/0130428 A1 | 5/2012 | Hunziker | |
| 2012/0179215 A1 * | 7/2012 | Soubeiran | A61B 17/7014 606/86 R |
| 2013/0150889 A1 | 6/2013 | Fening et al. | |
| 2014/0250674 A1 * | 9/2014 | Pool | A61B 17/7016 29/525.11 |
| 2014/0296919 A1 | 10/2014 | Culbert et al. | |
| 2014/0371796 A1 | 12/2014 | Kiester | |
| 2017/0095273 A1 | 4/2017 | Lynch et al. | |
| 2017/0172624 A1 * | 6/2017 | Brunner | A61B 17/7016 |

FOREIGN PATENT DOCUMENTS

| | | |
|---|---|---|
| DE | 200 13 178 U1 | 11/2000 |
| DE | 20 2008 016 178 U1 | 4/2009 |
| DE | 20 2008 016 179 U1 | 4/2009 |
| DE | 10 2009 042 844 A1 | 9/2010 |
| DE | 10 2009 043 179 A1 | 9/2011 |
| EP | 2 602 494 A1 | 6/2013 |
| JP | 2009-532190 | 9/2009 |
| JP | 2011-502003 | 1/2011 |
| WO | 0178614 A1 | 10/2001 |
| WO | 2004019796 A1 | 3/2004 |
| WO | 2007118179 A2 | 10/2007 |
| WO | 2008135250 A2 | 11/2008 |
| WO | 2009058546 A1 | 5/2009 |
| WO | 2012021378 A2 | 2/2012 |
| WO | 2012021378 A3 | 2/2012 |
| WO | 2012071373 A1 | 5/2012 |

OTHER PUBLICATIONS

PCT International Preliminary Report of Patentability, International Application PCT/US2015/035597, dated Dec. 15, 2016, 11 pages.
PCT International Preliminary Report of Patentability, International Application PCT/US2012/069118, dated Jun. 17, 2014, 8 pages.
PCT Written Opinion of the International Searching Authority and International Search Report, International Application PCT/US2012/069118, dated Feb. 26, 2013, 12 pages.
PCT Written Opinion of the International Searching Authority and International Search Report, International Application PCT/US2015/035597, dated Sep. 1, 2015, 15 pages.
Crown Heritage, Crown Heritage—EasAlign, Brochure, 2012, 3 pages.
INVIS (North America), Inc., INVIS Invisible, detachable joining. Brochure, 2010, 6 pages, North America.

* cited by examiner

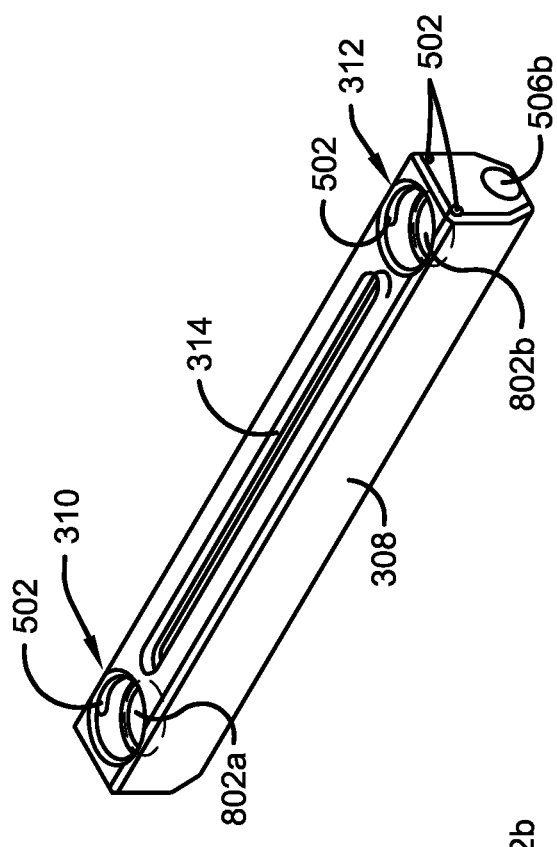
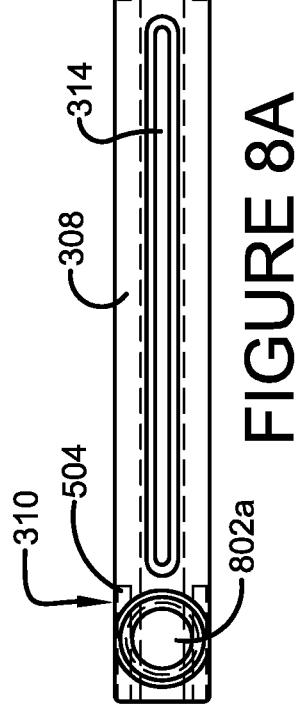
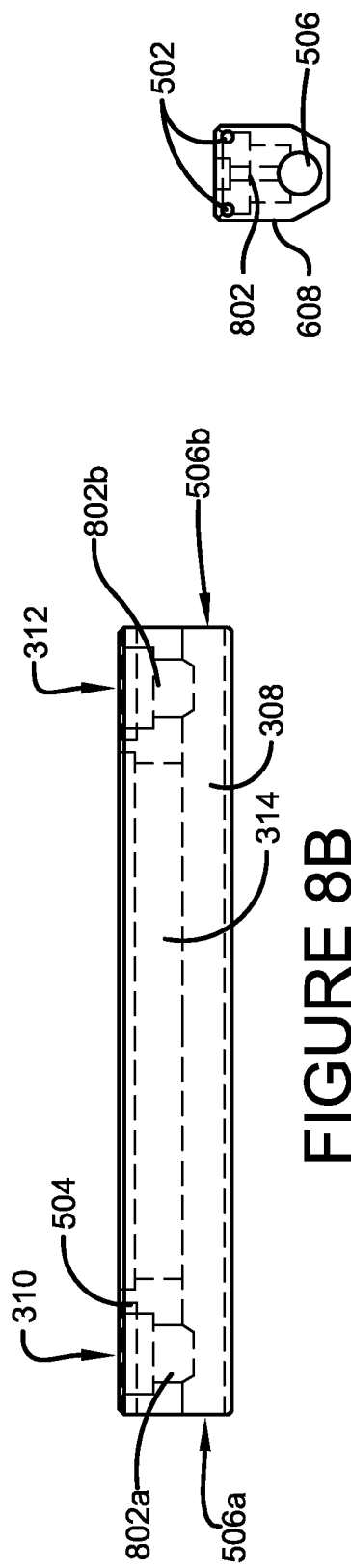

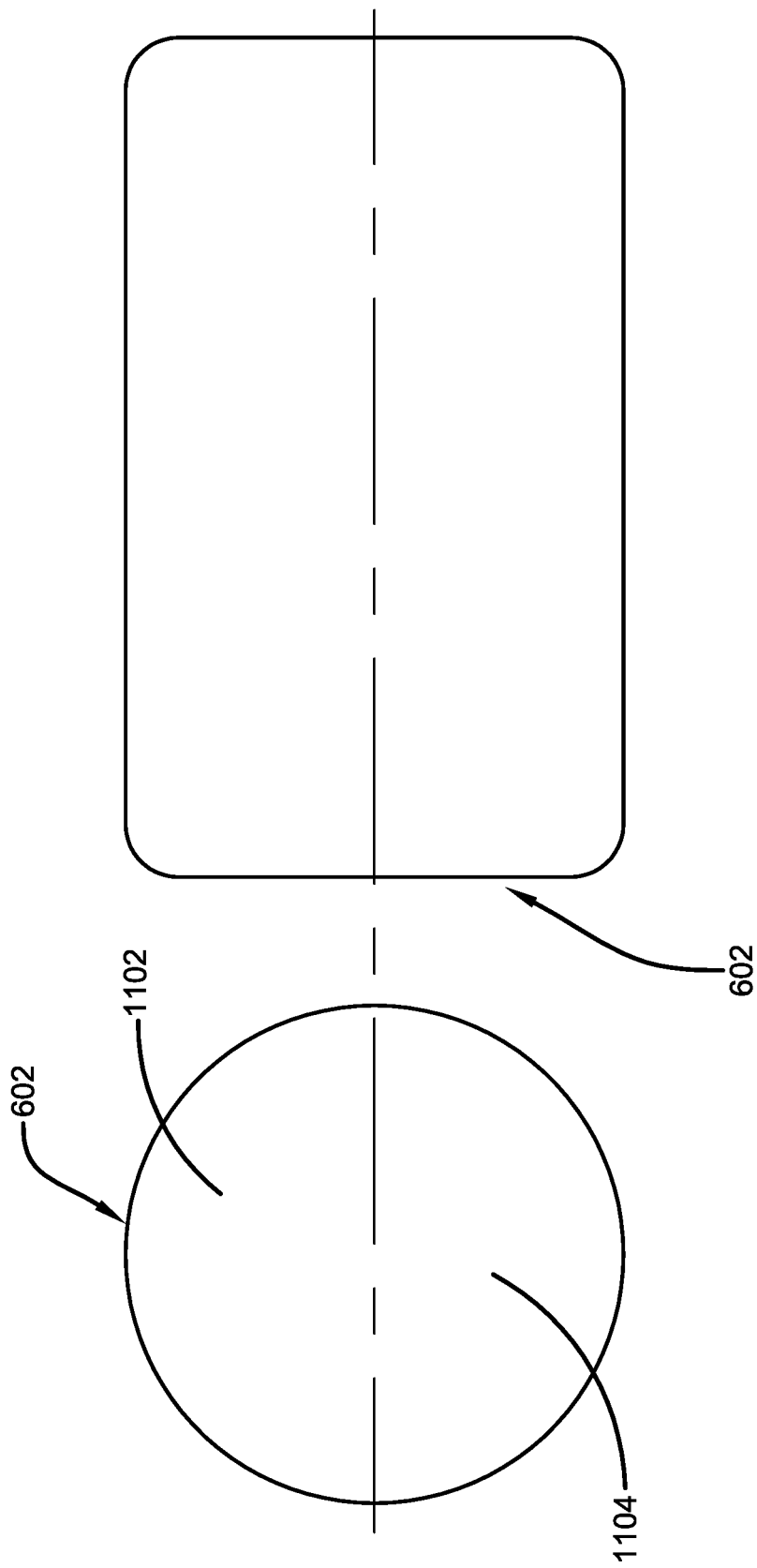

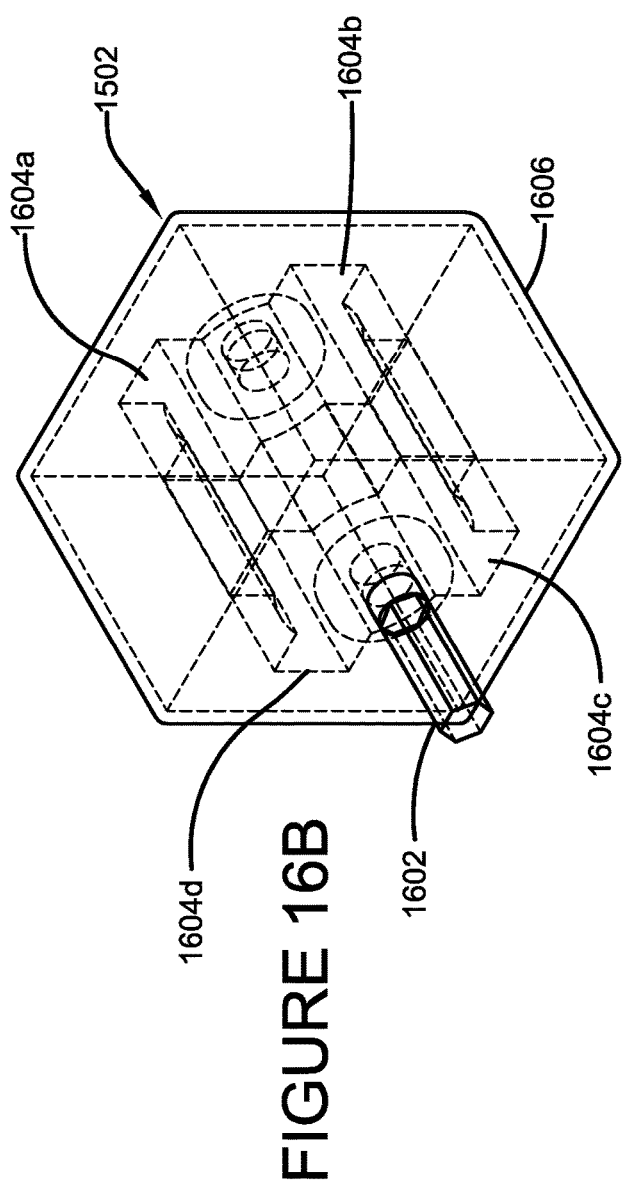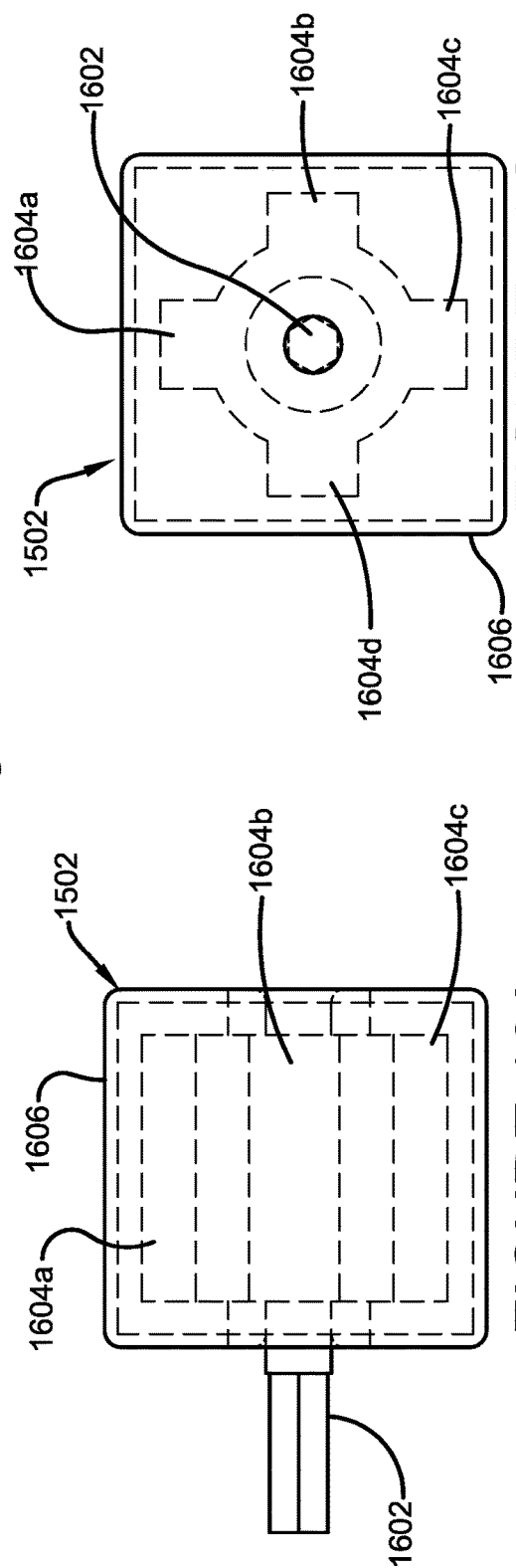
FIGURE 16B
FIGURE 16C
FIGURE 16A

DETAIL C

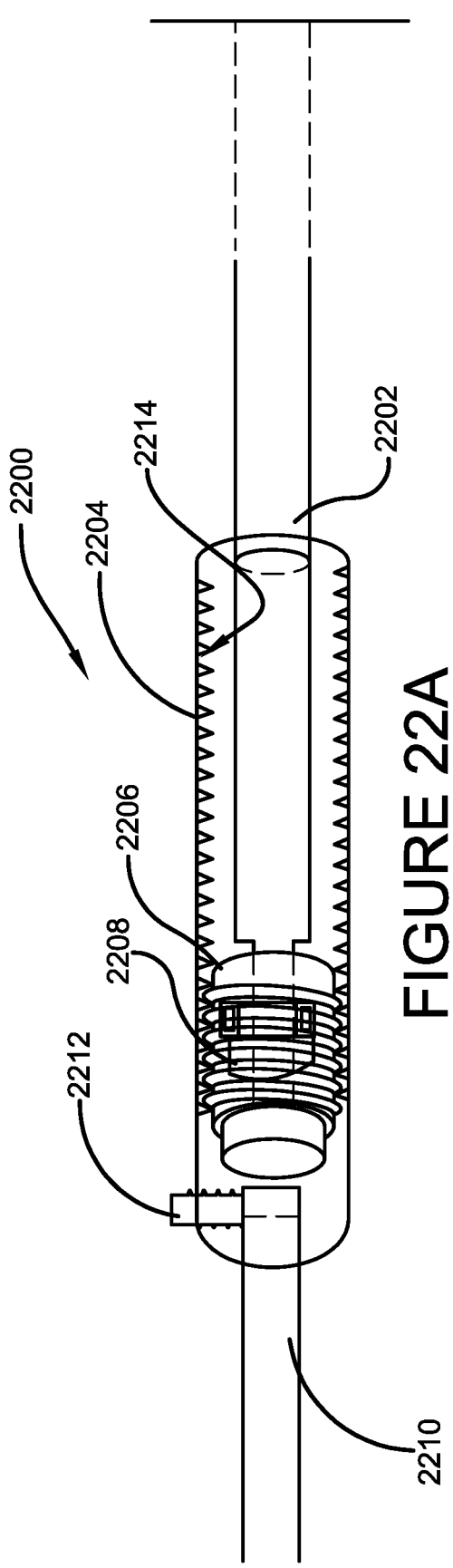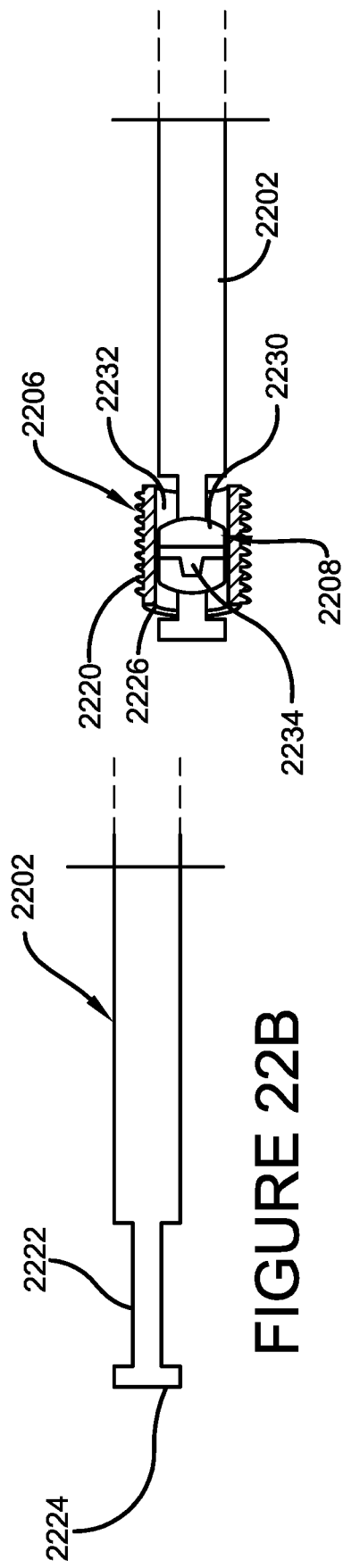

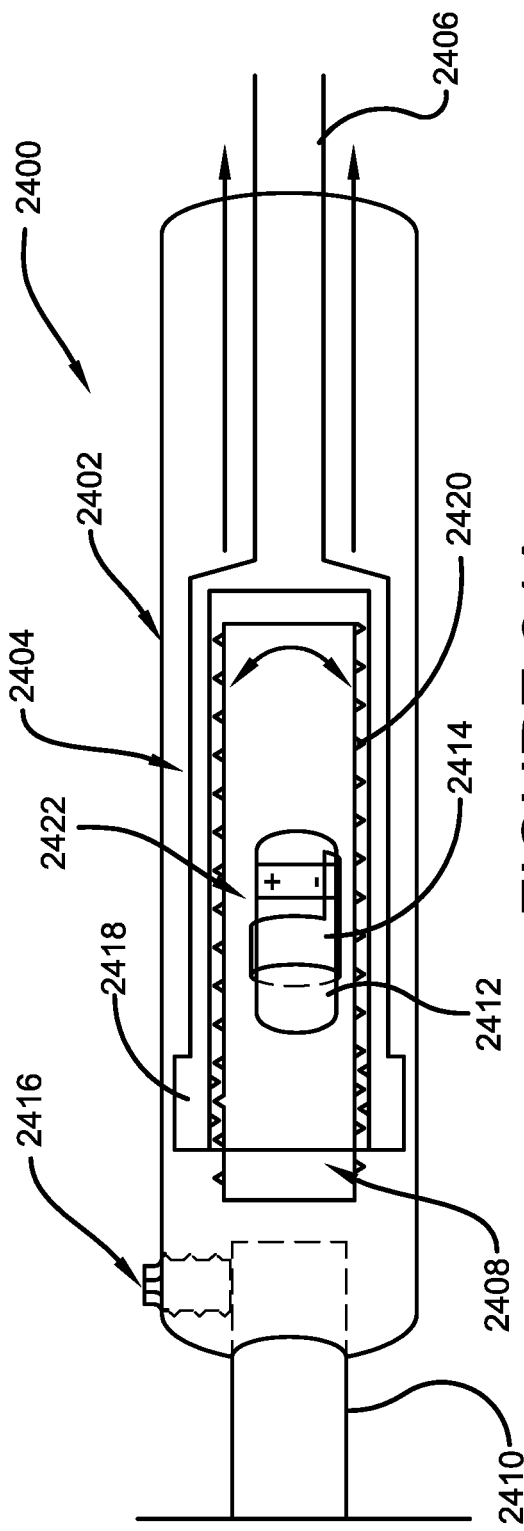
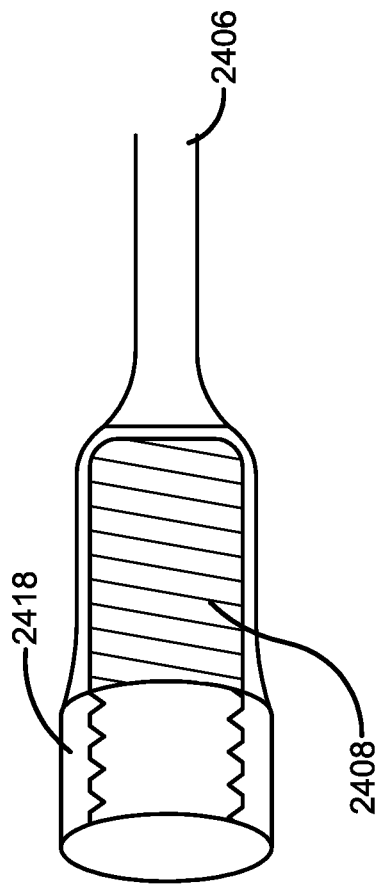
FIGURE 24A
FIGURE 24B

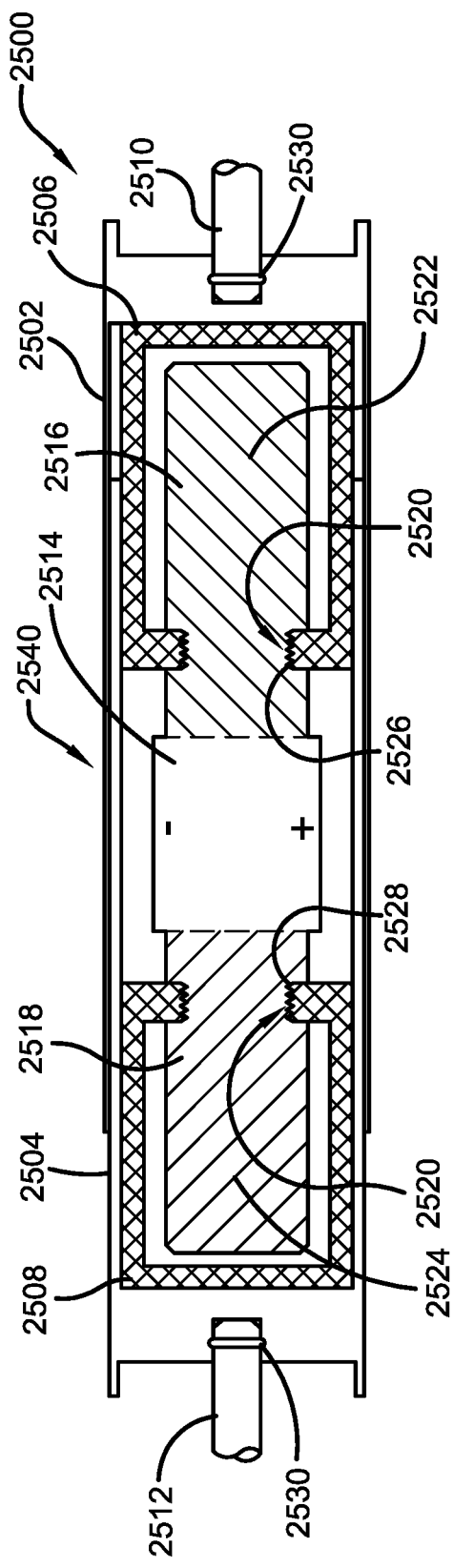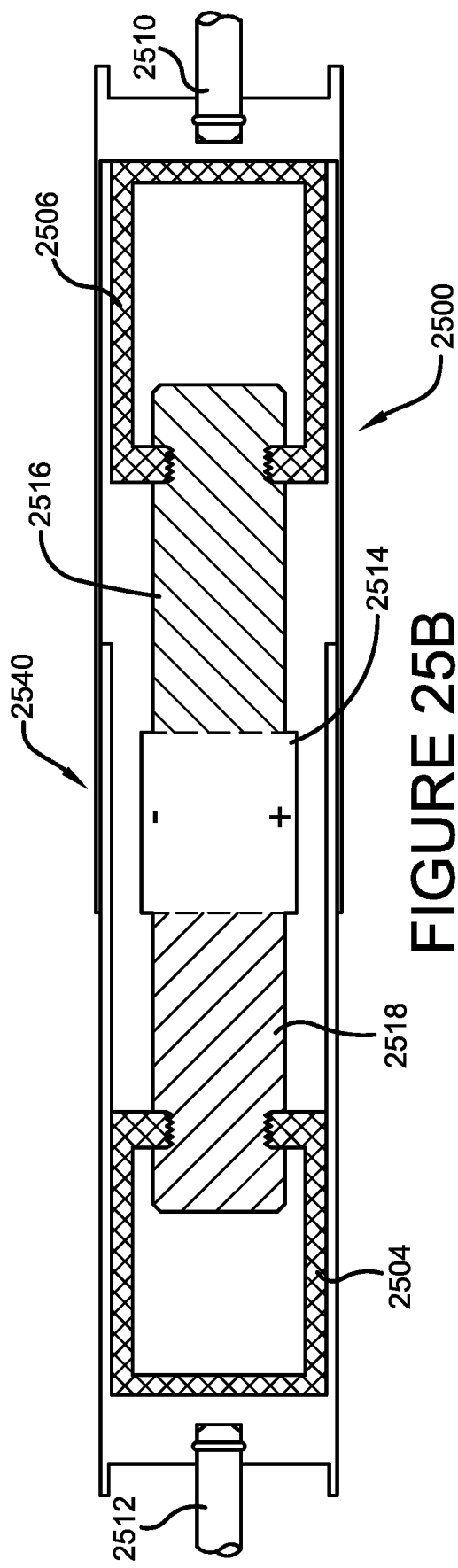
FIGURE 25A
FIGURE 25B

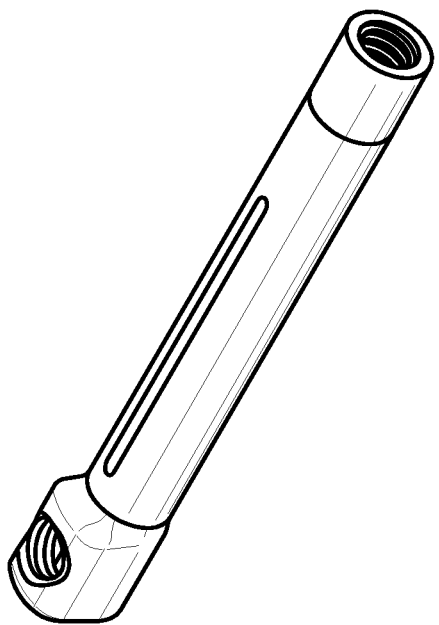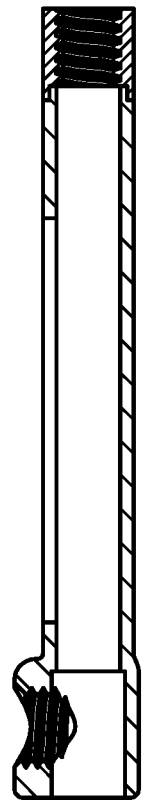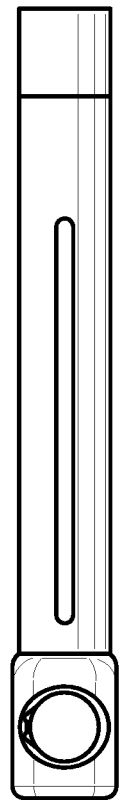
FIGURE 40

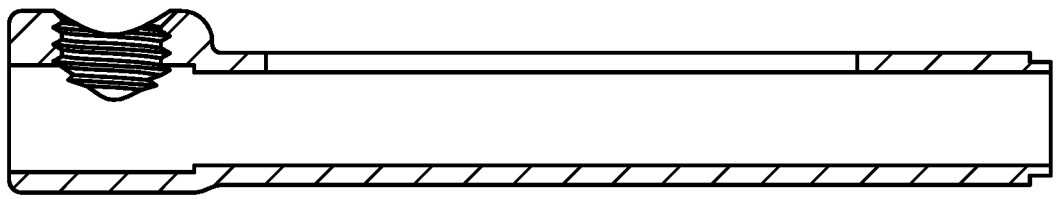
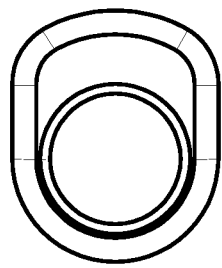
FIGURE 42

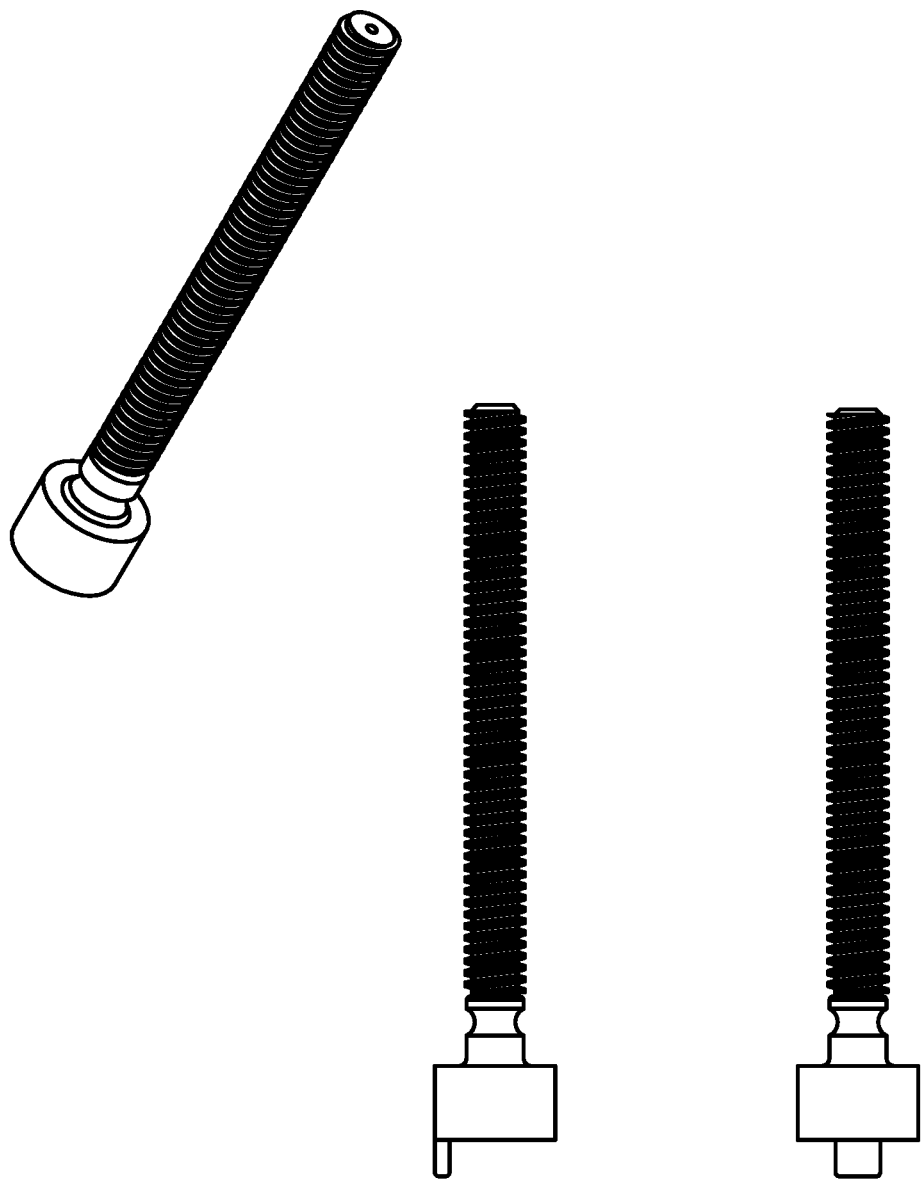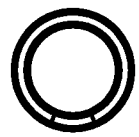
FIGURE 44

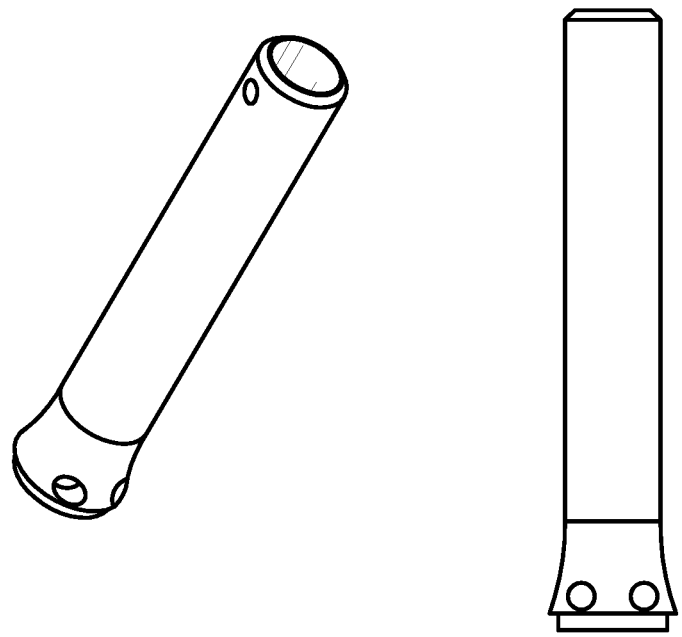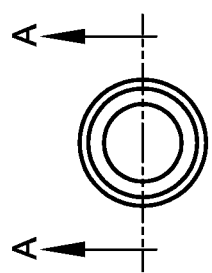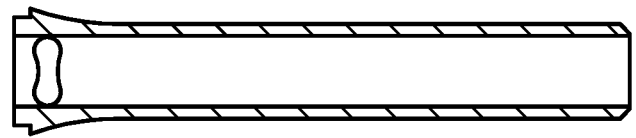
FIGURE 46

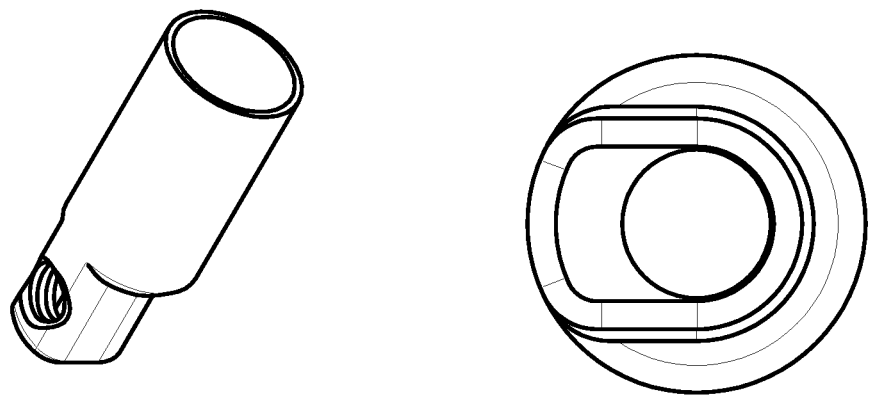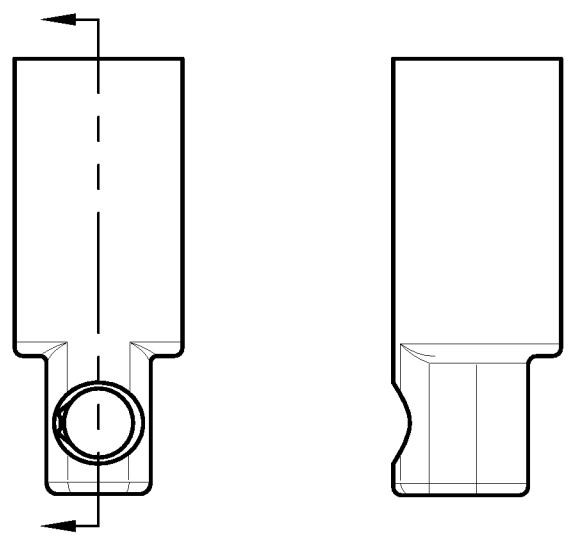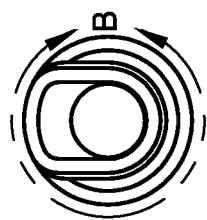
FIGURE 47

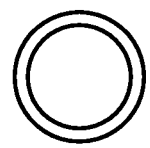
FIGURE 54

DISTRACTION OSTEOGENESIS SYSTEM

CROSS-REFERENCE TO RELATED APPLICATIONS

This application claims priority to U.S. Provisional Patent Application Ser. No. 62/419,732, entitled DISTRACTION OSTEOGENESIS ROD, filed Nov. 9, 2016, which is incorporated herein by reference. Further, this application is a continuation-in-part of, and claims benefit of, U.S. patent application Ser. No. 14/303,169 filed Jun. 12, 2014, entitled NONINVASIVE DEVICE FOR ADJUSTING FASTENER; which is a continuation-in-part of, and claims the benefit of U.S. application Ser. No. 13/712,387, filed Dec. 12, 2012; which claims the benefit of U.S. Provisional Application No. 61/569,453, filed Dec. 12, 2011, and which also claims the benefit of U.S. Provisional Application No. 61/585,450, filed Jan. 11, 2012.

BACKGROUND

Certain conditions, if left untreated, can result in damaging deformity early in life, which, in turn, can affect other aspects of a person's health. Thus, early treatment of such conditions can be vital to a person's future health and well-being. Typically, growing rods are surgically engaged with the patient's bones, and periodically adjusted (e.g., lengthened), for example, to stimulate growth of the bone to help in the treatment of a condition.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques and systems described herein can be utilized for distraction osteogenesis. That is, for example, an intramedullary distraction device may be used to provide for limb lengthening in a target patient. In one aspect, such a device may utilize a magnetically driven motor to provide for distraction. In this way, for example, distraction can be accomplished using an external magnetic field generator, which may facilitate treatment of a condition for the target patient.

In one implementation of device for bone lengthening, distraction drive can comprise a magnet rotating under application of a magnetic field, a rotational force applicator fixedly engaged with the magnet, and rotating with the magnet, and a drive component. The drive component can comprise a rotational force receiver that is fixed at a first end in direct contact with the rotational force applicator; and a linear force applicator disposed at a second end, and comprising external threads rotating upon application of a rotational force from the rotational force applicator to the rotational force receiver. Further, the example device can comprise a tail portion housing at least a portion of distraction drive in an internal chamber that facilitates the rotation of the distraction drive and mitigates linear translation of the distraction drive. Additionally, an elongated insertion portion with a nose disposed at a leading end. The nose can be shaped to facilitate insertion into a cavity of a target bone through an opening in the target bone. The insertion portion can comprising an internal cavity with an opening at an opposite end from the leading end to receive the second end of the drive component. In this implementation, a drive engagement component can be disposed proximate the opening to the internal cavity. The drive engagement component can comprise internal threads that are complementary to, and in threaded engagement with, the external threads of the linear force applicator to convert the rotation of the external threads to linear translation of the insertion portion.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein:

FIGS. 8A, 8B, 8C, and 8D are component diagrams illustrating various views of an example implementation of one or more portions of one or more systems described herein.

FIGS. 11A and 11B are component diagrams illustrating various views of an example implementation of one or more portions of one or more systems described herein.

FIGS. 16A, 16B, and 16C are component diagrams illustrating various views of an example implementation of one or more portions of one or more systems described herein.

FIGS. 22A, 22B, and 22C are component diagrams illustrating various views of an example implementation of one or more portions of one or more systems described herein.

FIGS. 24A and 24B are component diagrams illustrating various views of an example implementation of one or more portions of one or more systems described herein.

FIGS. 25A and 25B are component diagrams illustrating various views of an example implementation of one or more portions of one or more systems described herein.

FIGS. 38-54 are component diagrams illustrating one or more portions of an alternate embodiment of one or more systems described herein.

DETAILED DESCRIPTION

Figure 1:
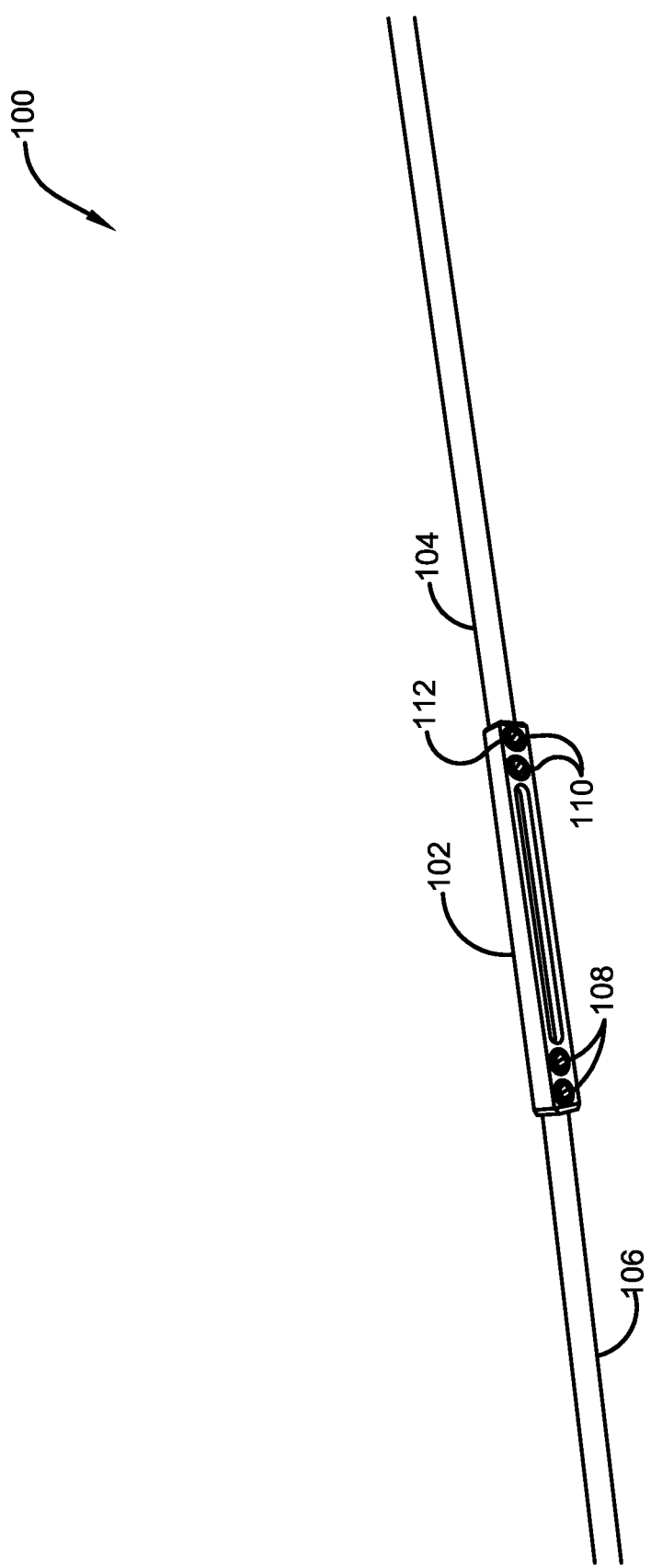
FIG. 1 illustrates a perspective view of an example growing rod apparatus.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

Typically, an initial management of scoliosis and other spinal deformities is undertaken using serial casting followed by bracing. If such treatment is not feasible, or not successful, surgical management is often warranted. Spinal fusion is a common form of surgical treatment for progressive scoliosis in adults and skeletally mature children. Spinal fusion usually involves placement of rods, hooks, pedicle screws, and/or bone grafts to correct the affected portion of the spine. However, this type of surgery can immobilize the treated sections of the spine. When a child is skeletally immature, spinal fusion treatment can limit the potential growth of the child, which may lead to other potential health problems, such as thoracic insufficiency syndrome, in which reduced or halted growth of the thorax may fail to provide sufficient volume for healthy adult respiratory function.

Some current options may allow for both scoliosis correction and future growth. Growth-sparing treatments, which may utilize dual growing rods (DGR) and/or vertical expandable prosthetic titanium rib (VEPTR), can provide for treatment of the scoliosis condition and may allow for continued thoracic growth. Conceptually, rods can be anchored to bones, including the spine, the rib, and/or the pelvis, and the rods are configured to be selectively lengthened. However, patients undergoing these treatments typically need repetitive surgical interventions to first implant, and subsequently lengthen the implants, sometimes as often as every four months.

FIG. 1 illustrates a perspective view of an example growing rod apparatus 100. As one example, some existing growth rod devices used to treat scoliosis in humans comprise a rod holder 102, one or more growth rods 104, 106, and one or more pairs of set screws 108, 110 used to secure the rod(s) 104, 106 to the rod holder 102. Typically, the set screws 108, 110 comprise a tool engagement opening 112 that is designed to receive a tool used to loosen and/or tighten the screw. For example, a hex-tool (e.g., Allen-wrench) may be inserted into the tool engagement opening 112 and rotated (e.g., clock-wise, counter clock-wise) to loosen and/or tighten the screw 108, 110.

Further, for example, in order to access the tool engagement opening 112 of the example growth rod apparatus 100, when the growth rod apparatus 100 is implanted in a patient, the patient needs to undergo invasive surgery (e.g., be cut open). In one implementation, when an adjustment of the example growth rod apparatus 100 is undertaken for young, skeletally immature patients, an open spinal surgery may be needed every six months until the age of skeletal maturity. Not only can these multiple surgeries pose a significant morbidity from the surgery alone, for example, but a severe psychosocial hurdle may be imposed, particularly for the skeletally immature and their care givers. While other complications to this type of treatment may arise, morbidity typically arises from the need for repeated surgical intervention. Infections and skin-related complications may lead to additional surgeries, long term antibiotics therapy, and psychosocial stress from chronic hospitalization on both the patient and the care-giver.

Figure 2:
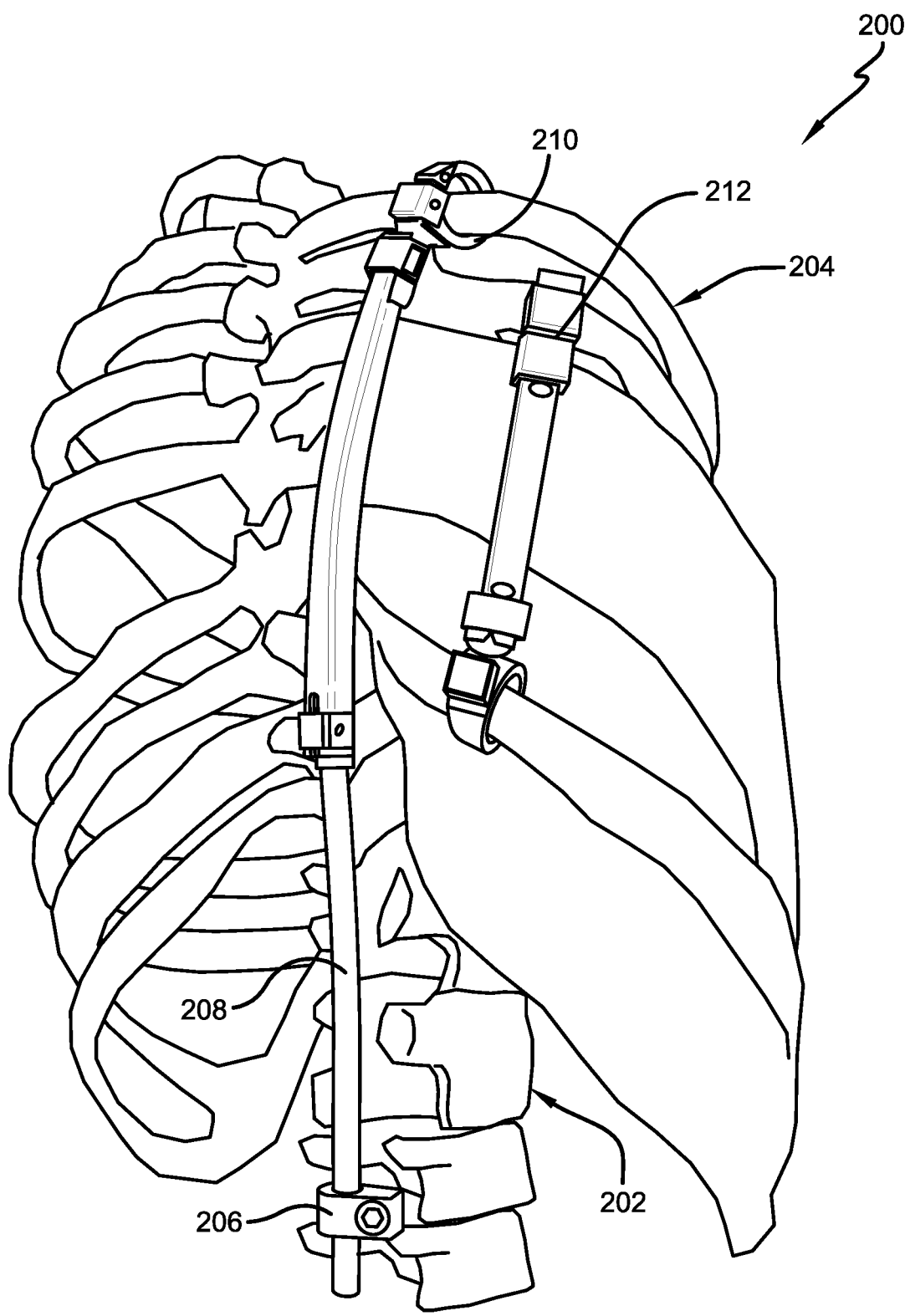
FIG. 2 illustrates a perspective view of another example growing rod apparatus.
Figure 3:
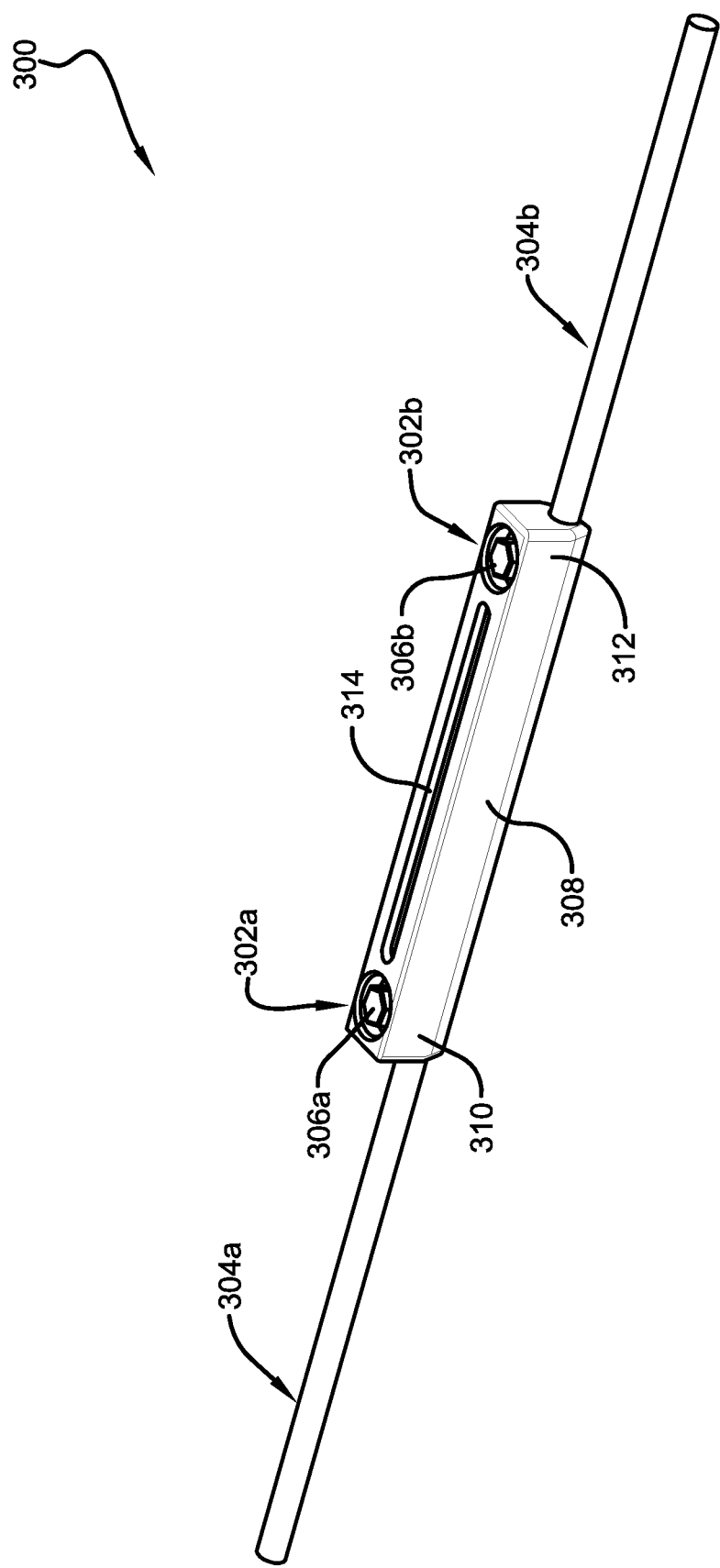
FIG. 3 a component diagram illustrating a perspective view of one or more portions an exemplary growth rod in accordance with one or more systems described herein.

FIG. 2 illustrates a perspective view of one implementation 200 of an example of a growing rod apparatus. In this example 200, a first type of growing rod system 208 may be engaged with (e.g., screwed into) a patient's spine 202 at a first end 206, and with the patients ribcage 204 at a second end 210. As one example, by securing the example, device 208 to the spine 202 and ribcage 204, a desired orientation of the patient's spine 202 may be obtained. Further, the desired orientation may be adjusted periodically, by surgically opening the patient and manually manipulating the device 208, for example, in order to adjust the spine to a desired final orientation. As another example, a second type of growth rod system 212 may be merely engaged with the patient's ribcage 204; however, manual manipulation via invasive surgery may still be needed.

Accordingly, as described herein, a non-invasive system and/or device may be devised that can provide a treatment for scoliosis, may allow for continued thoracic growth, and may mitigate repetitive surgical interventions. As one example, a system may utilize one or more rods respectively secured to a rod holder by one or more fasteners, where respective fasteners can be tightened and/or loosened by an external device (e.g., without surgical intrusion of the patient). That is, for example, a fastener can be coupled with a magnetic component that may be rotated by the external device. In this example, when the magnetic component rotates it may apply torque to the fastener, thereby tightening and/or loosening the fastener. Further, the fastener may be situated in the rod holder such that tightening the fastener can secure a corresponding rod, with respect to the rod holder. In one implementation, adjustment procedures for such a non-invasive device may be undertaken an exam room, for example, instead of an operating room.

Referring now to the drawings, which are for the purpose of illustrating implementations of a non-invasive system and/or device, and not for purposes of limiting the same, with reference to FIGS. 3-6, a system and/or device 300 for non-invasive tensioning, such as of an implanted growing rod treatment, is described. The non-invasive tensioning system 300 comprises a rod holder 308 comprising a first end 310 and a second end 312. The rod holder 308 is configured to selectively engage with a first rod 304a. Further, the non-invasive tensioning system 300 comprises a first fastener 302a disposed at the first end 310. The first fastener 302a is configured to secure the first rod 304a with respect to the rod holder 308. Additionally, the non-invasive tensioning system 300 comprises a first magnet component 602a that is operably coupled with the first fastener 302a. The first magnet component 602a is configured to apply torque to the first fastener 302a when it is subjected to a desired magnetic field.

In one implementation, the non-invasive tensioning system 300 can comprise a second fastener 302b disposed at the second end 312 of the rod holder 308. The second fastener 302b can be configured to secure a second rod 304b with respect to said rod holder 308. In one implementation, the second fastener 302b may be configured to secure the first rod 304a to the rod holder 308, for example, where the first rod 304a extends from the first end 310 to the second end 312 of the rod holder (e.g., through an entire length of the rod holder 308). Further, the non-invasive tensioning system 300 can comprise a second magnet component 602b, that is operably coupled with the second fastener 302b. The second magnet component 602b can be configured to apply torque to the second fastener 302b when it is subjected to the desired magnetic field.

As one example, using the magnet component 602 to loosen and/or tighten the fastener holding the rod in the rod holder may enables the exemplary tensioning system 300 (e.g., growing rod apparatus) to be re-tensioned without needing to gain direct, surgical access to heads 306 of the fasteners 302. In one implementation, the fasteners 302 may be rotated (e.g., loosened or tightened) by applying a desired magnetic field to the magnetic components 602. It should be understood that a magnetic field may induce a force upon certain components as described herein. As used herein the force induced by the magnetic field will be referred to as magnetic force. Further, in one implementation, the desired magnetic field can comprise a magnetic field that provides a desired amount of magnetic force in a desired orientation, for example, that cause the fastener to rotate in a desired direction (e.g., clockwise, counter-clockwise).

With continued reference to FIGS. 3-6, and further reference to FIGS. 7-13, the rod holder 308 of the exemplary system/device 300 can comprise a rod receiving shaft 506, sleeve, tube or any aperture that is entirely hollow or partially hollow. In one implementation, the rod holder 308 (e.g., as illustrated in FIGS. 8B and 8C) can comprise a first rod receiving shaft 506a with an opening at the first end 310, where the first rod receiving shaft portion 506a is configured to selectively engage the first rod 304a. Further, the rod holder 308 can comprise a second rod receiving shaft portion 506b with an opening at the second end 312, where the second rod receiving shaft portion 506b is configured to selectively engage the second rod 304b.

In one implementation, the first rod receiving shaft portion 506a and the second rod receiving shaft portion 506b may be disposed along a same shaft axis, for example, such that the first rod receiving shaft portion 506a and second rod receiving shaft portion 506b may form a continuous rod receiving shaft 506 through the rod holder 308. An elongated slot 314 can be disposed between the first end 310 and the second end 312. In one implementation, the first rod receiving shaft portion 506a and the second rod receiving shaft portion 506b may intersect the elongated slot 314, for example, such that the first rod 304a and/or the second rod 304b may be visible through an opening of the elongated slot 314 (e.g., to visibly determine a location of respective rods engaged in the shaft(s)).

In one implementation, the first rod receiving shaft portion 506a may lie along a first shaft axis and the second rod receiving shaft portion 506b may lie along a second shaft axis. As one example, the first and second shaft axes may be offset with respect to the rod holder 308. That is, for example the first rod receiving shaft portion 506a may run along the length of the rod holder 308 on a first side, while the second rod receiving shaft portion 506b may run along the length of the rod holder 308 on a second side. In this example, the first rod 304a can engage the first rod receiving shaft portion 506a, and the second rod 304b can engage the second rod receiving shaft portion 506b, and the two rods may not meet inside the rod holder, and they may extend completely through the length of the rod holder 308.

In one implementation, multiple fasteners may be disposed at respective ends 310, 312 of the rod holder 308 (e.g., as in FIG. 1). That is, for example, one or more additional fasteners can be disposed at the first end 310, along with the first fastener 302a. The one or more additional fasteners can also be configured to secure the first rod 304a with respect to the rod holder 308. Further, two or more second fasteners (e.g., the second fastener 302b and one or more additional fasteners) can be disposed at the second end 312, and can also be configured to secure the second rod 304b with respect to the rod holder 308.

Figure 4:
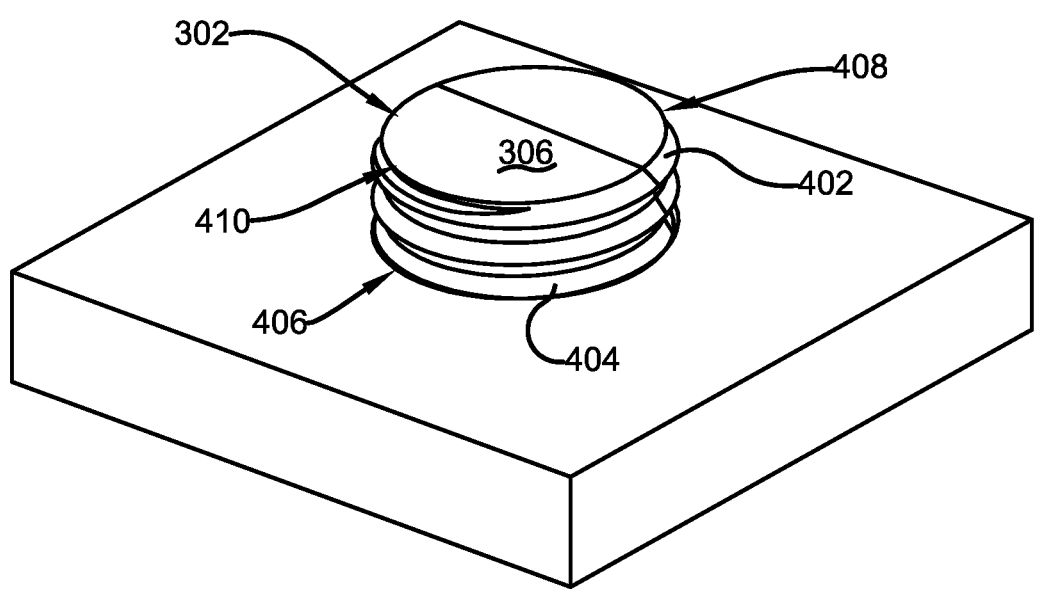
FIG. 4 is a component diagram illustrating a perspective view of an example implementation of one or more portions of one or more systems described herein.

As illustrated in FIGS. 3-13, respective fasteners 302 may comprise screw head 306, a screw shank 402, and a threaded portion 404. In one implementation, as illustrated in FIG. 4, the threaded portion 404 may be configured to be received by, and engage with, a threaded receiving portion 406, for example, disposed in the rod holder 308, such as at the first end 310 and/or the second end 312. In one implementation, the magnet component 602 may be operably coupled with the fastener 302 (e.g., such as at the screw shank 402), such that a north pole portion of the magnet component 602 resides at a first side 408 of the fastener 302, and a south pole portion of the magnet component 602 resides at a second side 410 of the fastener 302. In this way, for example, a north pole magnetic force applied to the first side 408 of the fastener 302 may cause the fastener 302 to rotate in a desired direction; and a south pole magnetic force applied to the second side 410 of the fastener 302, may cause the fastener 302 to continue to rotate in the desired direction. Further, if the application of the north pole and the south pole force is continuously alternated (e.g., rotationally), the fastener 302 may continue to rotate in the desired direction.

Figure 6:
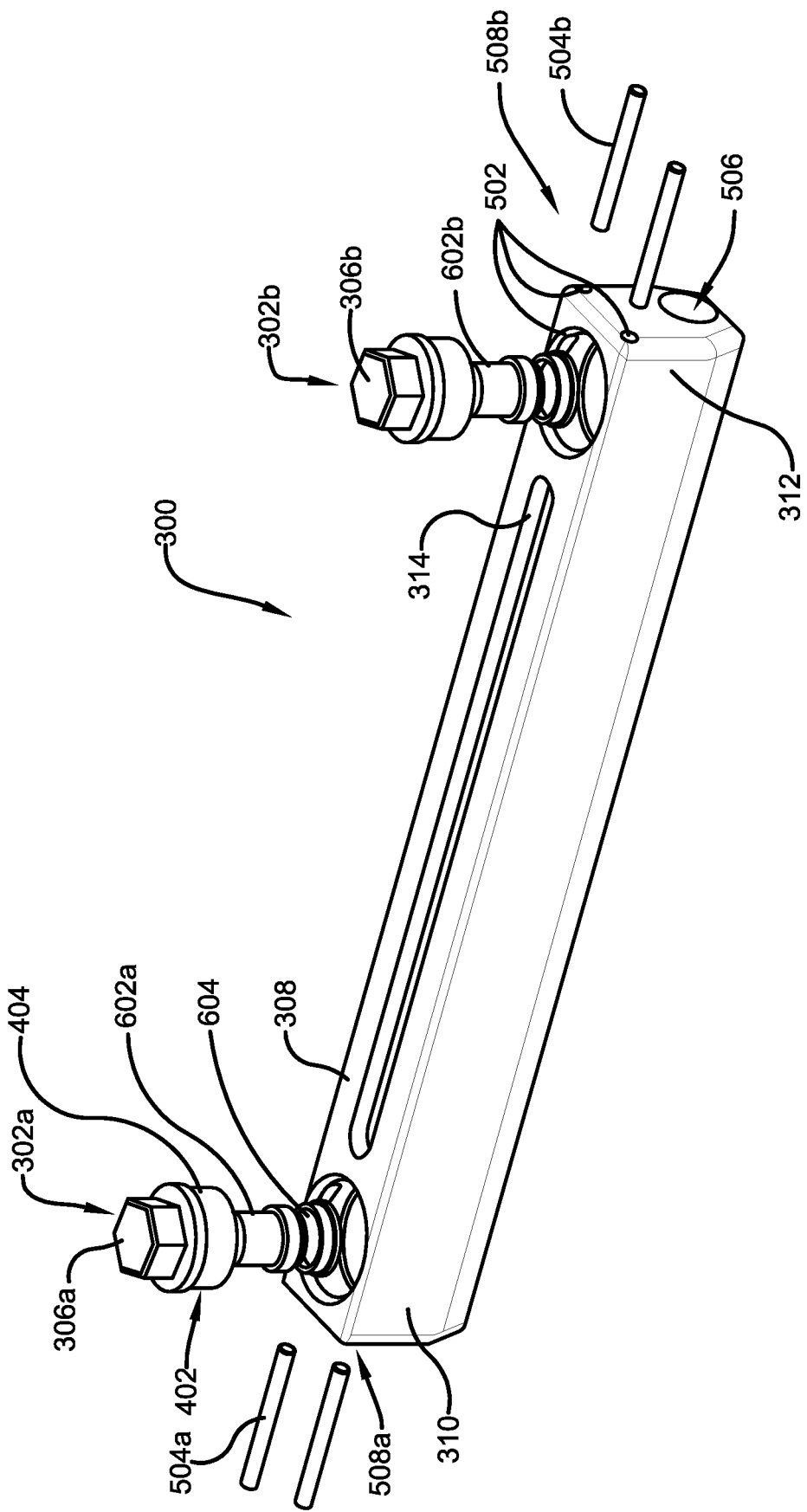
FIG. 6 is a component diagram illustrating an exploded view of an example implementation of one or more portions of one or more systems described herein.

In another implementation, the magnet component 602 may be disposed in rotational engagement with at least a portion of the fastener 302. As one example, as illustrated in FIG. 6, the first magnet component 602a may be rotationally engaged with the screw shank 402 of the first fastener 302a, and the second magnet component may be rotationally engaged with the screw shank 402 of the second fastener, 302b. As further illustrated in FIGS. 7 and 9A-D, the geometry of the fastener(s) 302 may be any form chosen with sound engineering judgment. In one implementation, the screw shank 402 may comprise a cylinder form. Further, the fastener 302 can comprise an interior portion 902, in which the magnet component 602 may be disposed, in rotational engagement with the fastener's shank 402.

In one implementation, the magnet component 602 (e.g., comprising one or more magnets) may be free floating or seated inside the interior portion 902, such that they are not fixedly engaged with any portion of the interior 902. In one example, the magnet component 602, as illustrated in FIGS. 11A and 11B, comprising opposite north 1102 and south 1104 poles, may freely rotate inside the interior portion 902 when subjected to the desired magnetic field, as described above.

With reference to FIGS. 7, 9A-D, 10A-D, and 11A-B, in one implementation, the fastener may comprise a magnet engaging component 904, such as an extension disposed in the interior portion 902 of the screw shank 402, that is engaged with the first fastener. In one implementation, the magnet engaging component 904 may be formed with the fastener 302; and in another implementation, the magnet engaging component 904 may be attached to the fastener 302. The magnet engaging component 904 can be configured to selectively engage with the magnet component 602, such that an application of torque to the first magnet component 602 that is engaged with the magnet engaging component 904 causes torque to be applied to the fastener 302.

In one implementation, the magnet component 602 may comprise a collar extension 702, which extends from a magnet collar 704 fixedly engaged with the magnet component 602. For example, the magnet collar component 704 may comprise an annular shape configured to merely fit around the magnet component 602 in fixed engagement. In one implementation, the magnet collar component 704 may be formed with the magnet component 602; in another implementation the magnet collar component 704 may be attached (e.g., press fit, adhered, glued, welded, soldered, etc.) to the magnet component 602. Further, the magnet collar component 704 can comprise the collar extension 702, which is configured to be disposed in opposing engagement with respect to the interior extension 904 disposed in the interior portion 902 of the screw shank 402.

As one example, as a magnetic force (e.g., as the desired magnetic field) is applied to the magnet component 602, the magnet component can rotate (e.g., in a direction dependent on the rotation of the desired magnetic field, as described above), and the collar extension 702 can engage the interior extension portion 904 of the fastener 302, which may cause the fastener 302 to rotate in the same direction of rotation. In one implementation, the interior portion 902 may comprise a track for the magnet component (e.g., and/or magnet collar 704) to improve engagement of the collar extension 702 with magnet engaging component 904 (e.g., interior portion extension), in order to provide the appropriate torque to the fastener 302.

In one aspect, when the magnetic force provided by the desired magnetic field causes the magnet component 602 (e.g., the collar extension 702 of the magnet collar 704) to engage the magnet engaging component 904 of the fastener 302, the magnet component 602 may rebound (e.g., bounce back from engagement), depending on an amount of rotational resistance extant for the fastener. In one implementation, upon the magnet component 602 disengaging (e.g., bouncing away from) the magnet engaging component 904, when the fastener encounters a certain amount of rotational resistance (e.g., stops rotating), the magnet component 602 can re-engage the magnet engaging component 904, when the magnet component 602 is subjected to the desired magnetic field. In this implementation, when the magnet component 602 re-engages the magnet engaging component 904, a rotational hammering force may be applied to the fastener 302.

As an example, the magnetic force provided by the desired magnetic field can be reapplied to the magnet component 602, causing it to re-contact the collar extension 702 of the magnet collar 704 within the screw shank 402 of the fastener 302. In this example, a repeated bounce-back and re-engagement action can cause a type of hammering effect between the collar extension 702 and the magnet engaging component 904 (e.g., the interior extension of the screw shank 402). It may be the hammering action, for example, that can cause the fastener 302 to rotate, particularly when subjected to rotational resistance. In this way, for example, a loose screw may be tightened more effectively, and a tight screw may be loosened more effectively.

Figure 7:
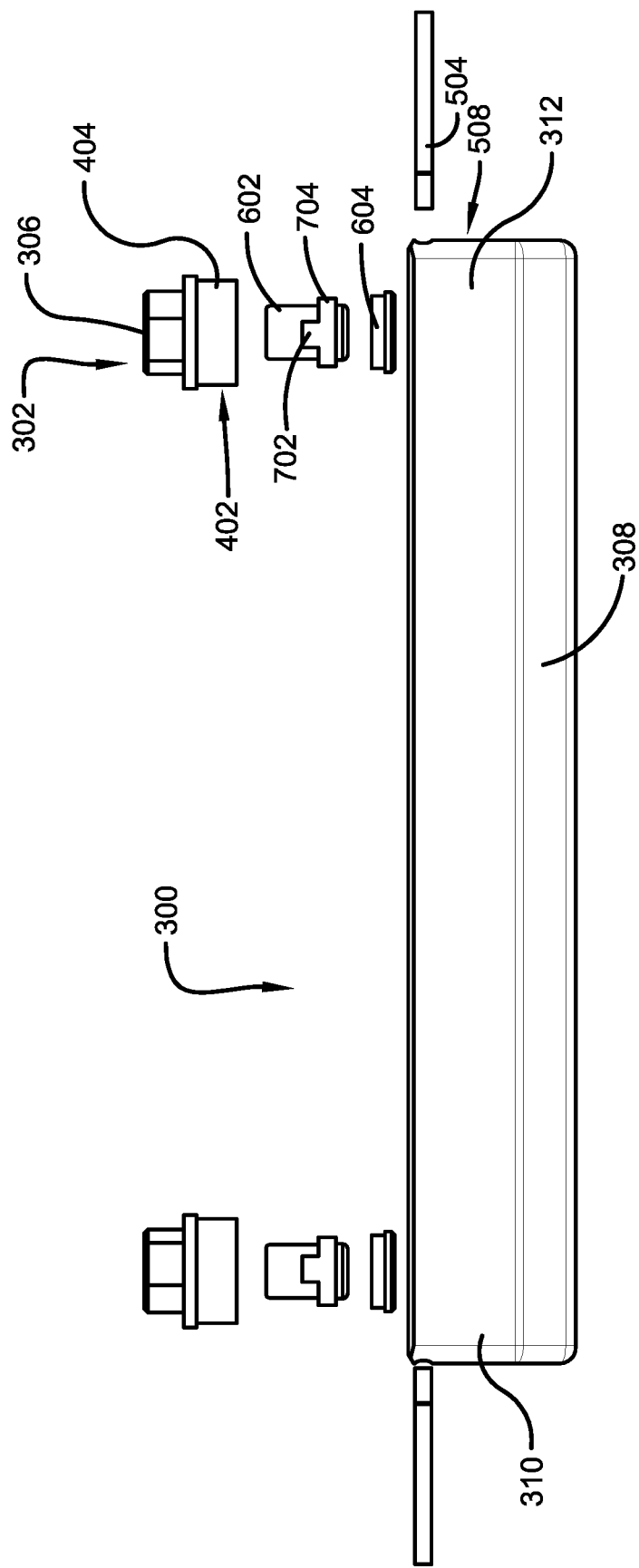
FIG. 7 is a component diagram illustrating an exploded view of an example implementation of one or more portions of one or more systems described herein.
Figure 9A:
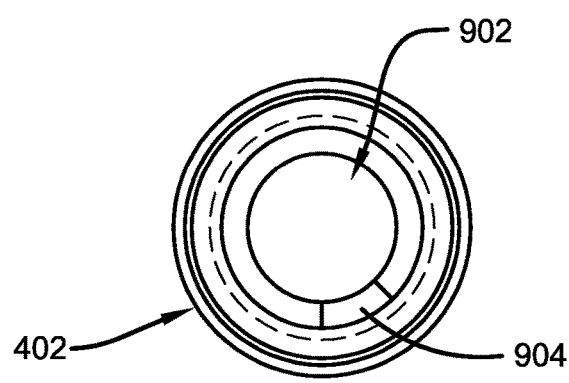
FIGS. 9A, 9B, 9C, and 9D are component diagrams illustrating various views of an example implementation of one or more portions of one or more systems described herein.
Figure 9C:
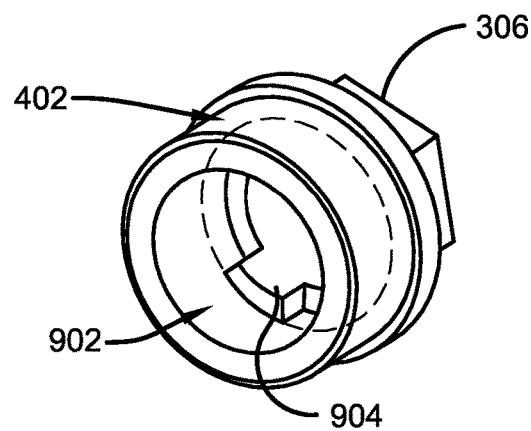
Figure 9B:
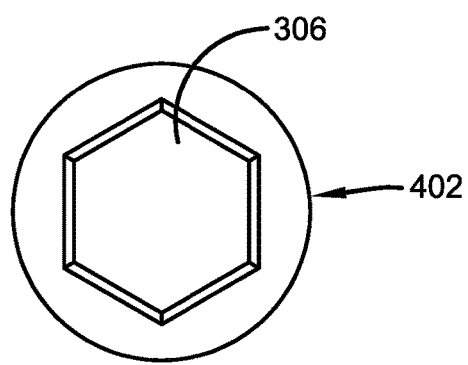
Figure 9D:
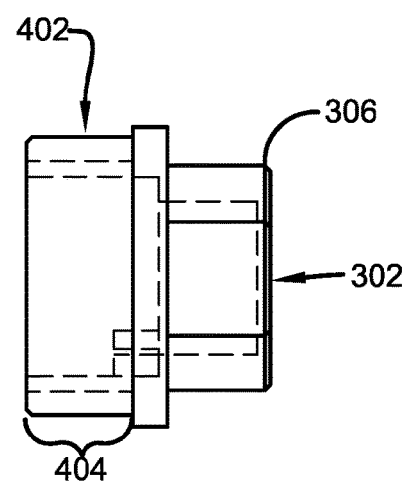
Figure 10C:
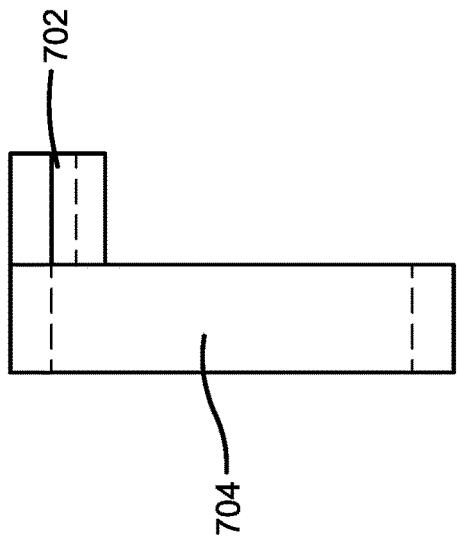
FIGS. 10A, 10B, 10C, and 10D are component diagrams illustrating various views of an example implementation of one or more portions of one or more systems described herein.
Figure 10D:
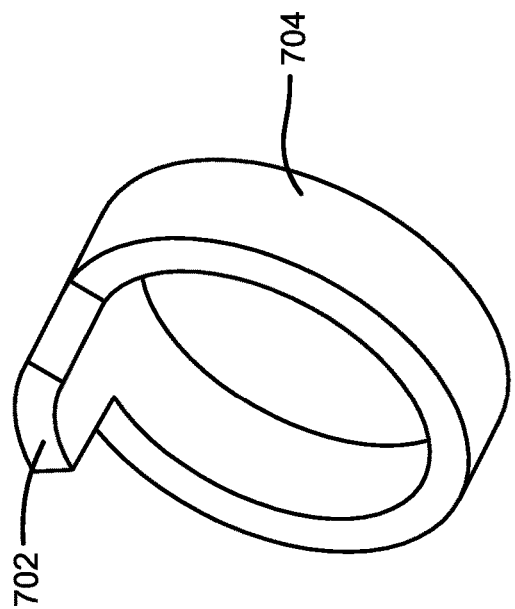
Figure 10A:
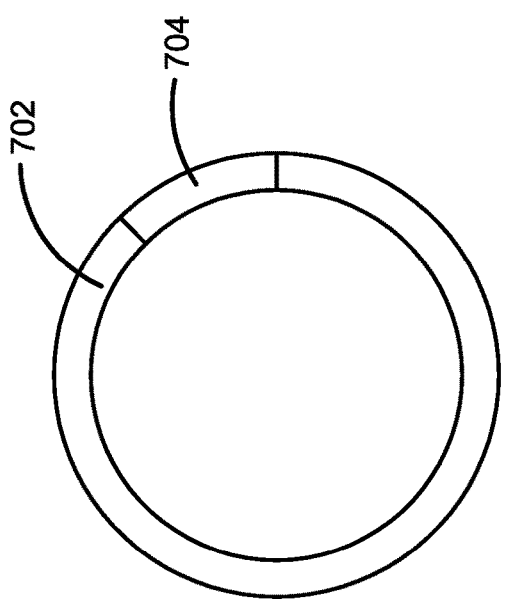
Figure 10B:
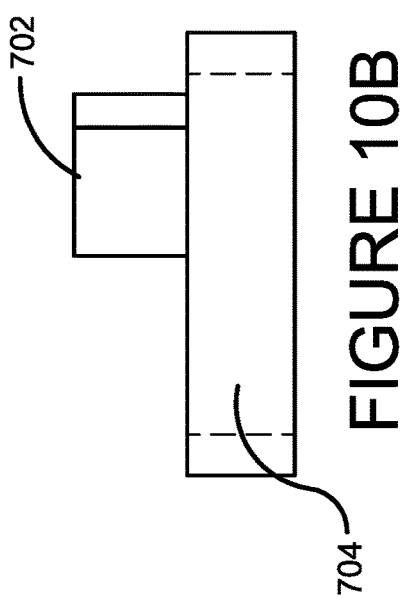
Figure 12B:
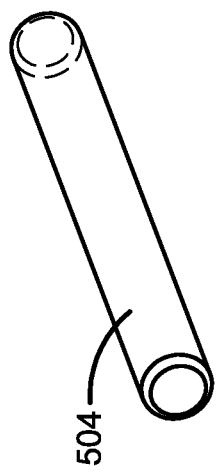
FIGS. 12A, 12B, and 12C are component diagrams illustrating various views of an example implementation of one or more portions of one or more systems described herein.
Figure 12C:
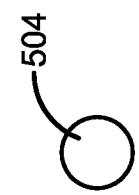
Figure 12A:
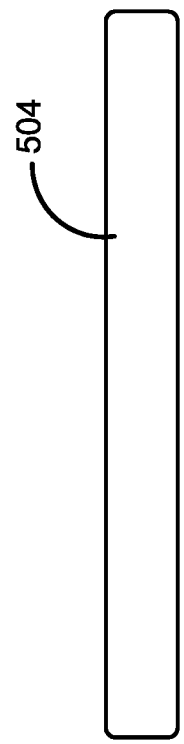
Figure 13B:
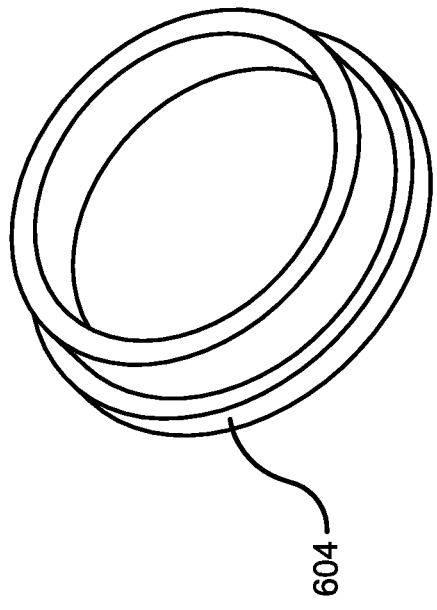
FIGS. 13A, 13B, and 13C are component diagrams illustrating various views of an example implementation of one or more portions of one or more systems described herein.
Figure 13C:
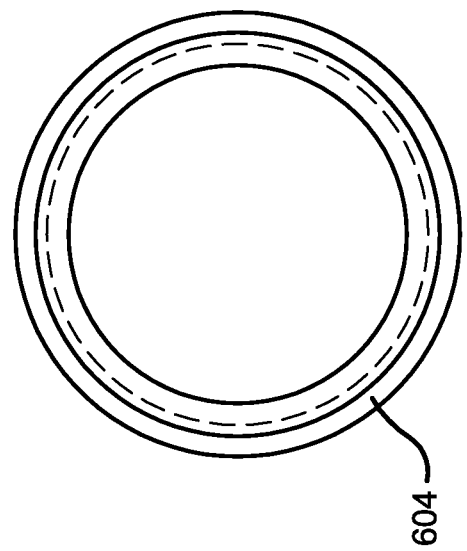
Figure 13A:
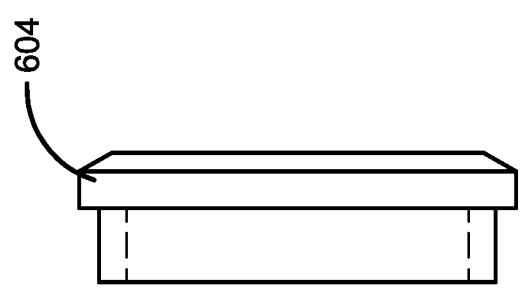

With reference to FIGS. 6-8, 12A-C, and 13A-C, and continued reference to FIGS. 3-5 and 9-11, a screw cap 604 may be operatively coupled with the fastener 302, for example, with the magnet component 602 positioned therebetween, as illustrated in FIGS. 6 and 7. In one implementation, the screw shank 402 may comprise a blunt end disposed at an end portion of the threaded portion 404. The blunt end may be engaged with the screw cap 604, such as by pressure fitting. As one example, the blunt end engaged with the screw cap 604 may be configured to apply pressure to a rod 304 inserted into the rod holder 308 (e.g., when the threaded portion is tightened down), such that the rod 304 may be secured (e.g., to a desired tensioning force) within the rod receiving shaft 506 of the rod holder 308.

Figure 5:
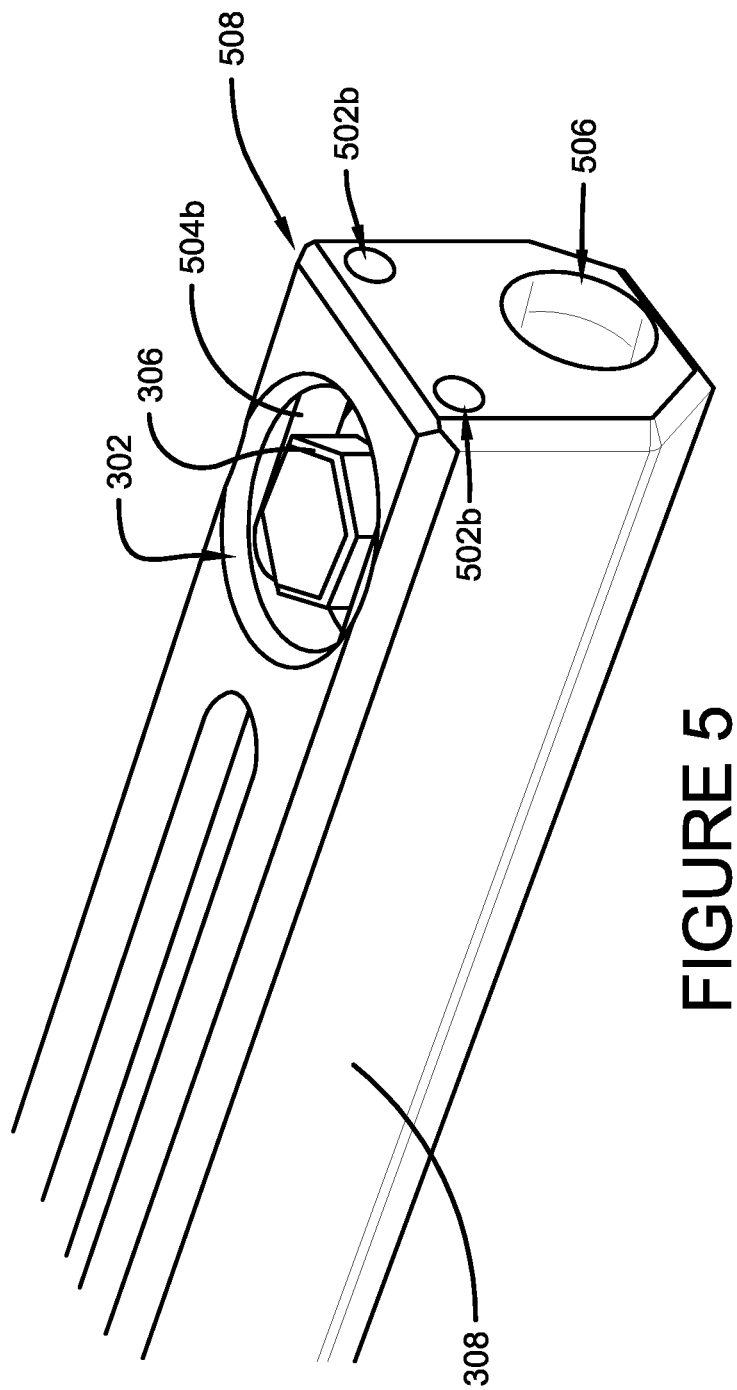
FIG. 5 is a component diagram illustrating a perspective view of an example implementation of one or more portions of one or more systems described herein.

As illustrated in FIGS. 5-7, a first screw stop component 508a may disposed in the first end 310, and/or a second screw stop component 508b may disposed in the second end 312 of the rod holder 308. The screw stop component 508 may be configured to mitigate over-rotation of the fastener 302, past a desired setting. The screw stop component 508 can comprise a stop receiver 502, comprising a tube disposed in the rod holder, and a stop pin 504, configured to be selectively engaged with the stop receiver 502. As one example, the stop pin 504 may be inserted into the stop receiver 502 after the fastener 302 is inserted into a fastener receiving hole 802 of the rod holder 308. In this way, for example, as illustrated in FIG. 5, a portion of the screw head 306 may engage the stop pin 504 when the fastener 302 is loosened (e.g., rotated out), preventing the fastener 302 from rotating past the position of the stop pin 504.

As an example, the screw stop component 508 may mitigate inadvertently unscrewing the fastener completely from the fastener receiving hole 802, thereby becoming disengaged from the rod holder 308. The screw stop component 508 may comprise any mechanical stop chosen with sound engineering judgment. As an example, the screw stop component 508 may be internal to the rod holder 308, as illustrated in FIG. 5, and/or it may be external to the rod holder 308. In an alternative design, the screw stop component 508 may be integrated with the fastener 302 itself, and/or may be fastened to the interior or exterior of the fastener 302.

Figure 14:
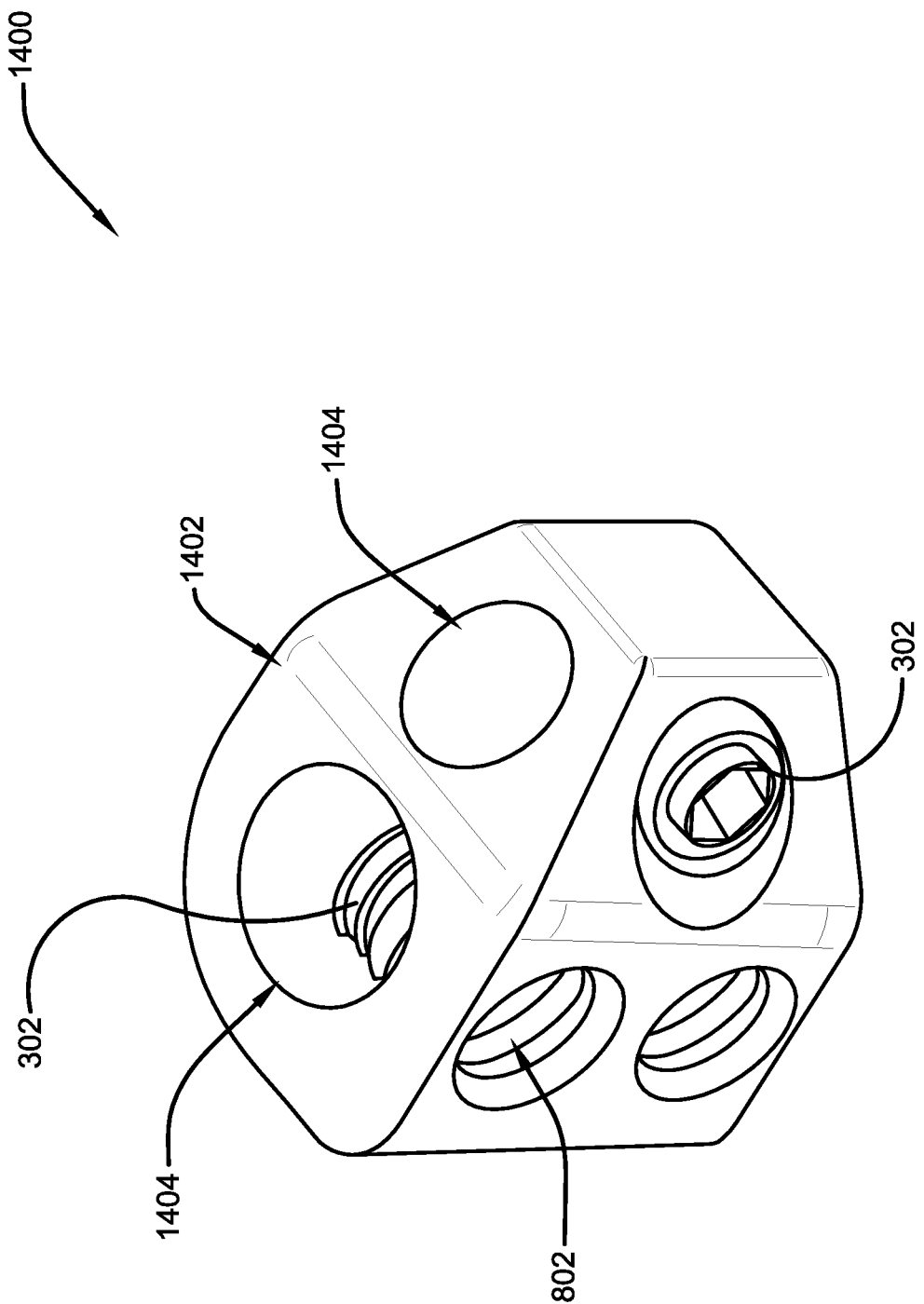
FIG. 14 is a component diagram illustrating a perspective view of an example implementation of one or more portions of one or more systems described herein.

As illustrated in FIGS. 8 and 14, the rod holder 308 may comprise a first screw receiving hole 802*a* and a second screw receiving hole 802*b*. The screw receiving hole(s) may be configured to receive a fastener 302, such as a set screw. It is anticipated that alternate configurations of the rod holder/fastener configuration may be designed by those skilled in the art. As an example, in one implementation, a rod holder may comprise a type of rod clamp 1402, where a set screw-type fastener 302 may be utilized to secure one or more rods in respective rod holding shafts 1404.

In one implementation, one or more portions of the fastener 302 and/or fastener receiving hole 802 may be encapsulated with a suitable (e.g., medically inert) material. In one implementation, the magnet component 602 can be encapsulated within fastener 302, for example, to mitigate corrosion of the magnet component 602. As one example, the screw cap 604 may seal the magnet component 602 inside the interior portion 902 of the screw shank 402. In one implementation, encapsulation of the entire non-invasive tensioning device 300 may mitigate formation of undesirable materials on working parts of the device 300, for example, which may interfere with the ability of the threaded portion 404 to effectively engage with the screw receiving hole 802 of the rod holder 308.

With continued reference to FIGS. 3-14, a first fastener 302*a* may be inserted in a first screw receiving hole 802*a*, and a second fastener 302*b* may be inserted into a second screw receiving hole 802*b*. In one implementation, the first and/or second fasteners 302 may comprise set screws, for example, where a set screw may comprise a flat or relatively blunt end, configured to engage a rod 304, to secure the rod 304 against the rod holder 308 using pressure. In one implementation, the set screw may comprise a pointed or relatively pointed end, configured to engage an indentation, hole, valley, notch, or other set screw receiving cut-out, of the rod 304.

As one example, the rod 304 may comprise a plurality of rod positioning elements (e.g., indentations, holes, valleys, notches, etc.) respectively configured to facilitate securing of the rod with respect to said rod holder at a desired position. For example, the rod positioning elements may be disposed at locations along the rod suitable for adjusting the rod with respect to the desired scoliosis treatment. As another example, the respective one or more rods (e.g., 304*a*, 304*b*) may comprise a plurality of indentations respectively disposed at a desired interval, and/or a plurality of rises respectively disposed at a desired interval, where the indentations and/or valleys between the rises may selectively engage the set screw, and help secure the rod 304 in the rod holder 308.

In another implementation, of the present invention, the rod 304 may comprise one or more teeth that are configured to engage corresponding teeth disposed in the rod holder 308. As one example, the teeth on the rod 304 may engage the teeth in the rod holder 308 to provide a type of ratcheting adjustment system, where the rod may be selectively adjusted according to desired ratcheting positions of the teeth.

With continued reference to FIGS. 3-14, in one implementation, after the respective one or more fasteners are engaged with the rod holder 308 (e.g., screwed into the rod holder), a first stop pin 504*a* may be engaged with (e.g., inserted into) a first stop receiver 502*a*, and/or a second stop pin 504*b* may be engaged with a second stop receiver 502*b*. In this way, as described above, the fastener(s) may not be inadvertently disengaged from the rod holder 308.

A first growing rod 304*a* may be inserted into the first rod receiving shaft 506*a* of the rod holder 308, and a second growing rod 304*b* may be inserted into the second rod receiving shaft 506*b* of the rod holder 308. In one implementation, as described above, the first and/or second growing rods 304 may be selectively fastened to bone, such as a portion of the spine and/or ribcage. Further, in one implementation, the rod holder 308 may be selectively fastened to bone (e.g., in a human), for example, such as using the rod clamp of FIG. 14. As an example, after fastening the non-invasive tensioning device 300 to the bones, the patient may be surgically closed.

With reference to FIGS. 15 and 16A-C, and continued reference to FIGS. 3-14, in order to make an adjustment to the non-invasive tensioning device 300, which may have been surgically implanted in the patient, the rod holding fasteners 302 may need to be loosened. In order to turn the fasteners 302 without invasive surgery, a magnetic field generation component 1502 may be utilized. The magnetic field generation component 1502 can comprise one or more actuation magnets 1604, and an axle 1602 operably coupled with the one or more actuation magnets 1604. The axle 1602 may be configured to cause the actuation magnet(s) 1604 to rotate around an axis of magnet rotation to generate the desired magnetic field. As one example, the rotating magnets can provide the magnetic force needed to rotate the fastener, when brought in close proximity to the magnet component 602 disposed in the fastener 302.

As one example, a first actuation magnet 1604*a* may comprise a north pole disposed at its outward facing end, a second actuation magnet 1604*b* may comprise a south pole disposed at its outward facing end, a third actuation magnet 1604*c* may comprise a north pole disposed at its outward facing end, and a fourth actuation magnet 1604*d* may comprise a south pole disposed at its outward facing end. In this example, when the axle 1602 is rotated, an alternating north-south magnetic force may be provided at a face of the magnetic field generation component 1502. For example, the magnetic field generation component 1502 can comprise a housing 1606, a face of which may be placed proximate to a location of a fastener 302 in the non-invasive tensioning device 300 disposed in the patient. When activated (e.g., rotated in a desired direction), the alternating north-south magnetic force can be provided at the housing face, which may cause the fastener 302 to rotate (e.g., non-invasively), as described above.

Further, in one implementation, the one or more magnets 1604 of the magnetic field generation component 1502 can be rotated in a first direction (e.g., clockwise), for example, causing rotational torque to be applied to a fastener 302 in the first direction. In this implementation, the one or more magnets 1604 of the magnetic field generation component 1502 can be rotated in a second direction (e.g., counter-clockwise), for example, causing rotational torque to be applied to the fastener 302 in the second direction.

Additionally, an orientation of the magnetic field generation component 1502 with respect to a rotating magnetic component, disposed adjacent, (e.g., a fastener) may determine whether the adjacent rotating magnetic component is affected by the resulting magnetic field. For example, where two rotating magnetic components are disposed relatively perpendicular to each other (e.g., disposed on a growing rod apparatus in a patient), placing the magnetic field generation component 1502 in a first orientation, with respect to the rotating magnetic components, may cause rotational torque to be applied to merely a first one of the rotating magnetic components. In this example, placing the magnetic field generation component 1502 in a second orientation, with respect to the rotating magnetic components, may cause rotational torque to be applied to merely a second one or the rotating magnetic components, and not to the first. In this way, for example, if a physician wishes to loosen (e.g., or tighten) only one fastener at a time, an appropriate orientation of the magnetic field generation component 1502 may be used such that the desired fastener is affected by the resulting magnetic field, and not non-desired fasteners.

In one aspect, the action of the magnetic force from the magnetic field generation component 1502 can produce a hammering force, as described above. In one implementation, the magnet component 602 may rotate in a one to one revolution relative to the screw shank 402 and threaded portion 404 until rotational resistance is encountered, such as from a tightening against the growing rod 304, or against the screw stop component 508. In this implementation, for example, when rotational resistance is encountered, the magnet component 602 may not rotate at the same speed as the screw shank 402 and threaded portion 404. That is, for example, the magnets component 602 may have a greater velocity than the screw shank 402. In this example, respective turns of the magnet component 602 may attempt to rotate the screw shank 402 one revolution. However, if rotational resistance is encountered, the fastener 302 may not turn an entire revolution.

As an illustrative example, if a doctor determines that the tension of the growing rods needs to be adjusted, the magnetic field generation component 1502 may be used to loosen the fastener(s) securing the one or more tensioning rods 304. In this example, the magnetic field generation component 1502 can be placed in close proximity to the patient, and rotated (e.g., manually or by a powered rotation source, such as a powered screwdriver, drill, etc.). Further, the rotation can be applied in a direction that causes the magnet component 602 to rotate (e.g., in a clockwise direction) within the fastener 302, in a fashion that produces torque, for example, as described above, the torque can cause the fastener 302 to rotate (e.g., loosen).

Additionally, in this example, after adjusting the patient into a desired position (e.g., moving the tensioning rod(s) 304 into and/or out of the rod holder 308), the respective fasteners may be re-tightened. As an example, the rotation of the magnetic field generation component 1502 can be reversed, thereby cause the fasteners to rotate in an opposite direction (e.g., counter-clockwise). In this example, the fastener 302 may rotate into the screw receiving hole 802 of the rod holder 308, at least until it contacts the growing rod 304. As described above, the hammering force provided by the magnet component 602 may cause the fastener to securely hold the rod 304 in the rod holder 308. In one implementation, non-invasive tensioning device may comprise a fastener locking component configured to mitigate loosening of the fastener 302 from secure engagement with the rod 304.

In one aspect, when the growing rods (e.g., 304) are adjusted, means may be used to measure the change in position of the rods. In one implementation, in order to measure the distraction, any means chosen with sound engineering judgment may be applied. As one example, the use of beads (not shown) on the growing rods may be used, which can be detected using a non-invasive scan, such as CT scan, fluoroscopy, or other noninvasive means. In one implementation, electromagnetic means may be used to determine a distance of distraction, such as during adjustment. As one example, a sensing means (e.g., sensor device) may be implemented to determine a polarity change of a rotating magnetic component, such magnetic drive screw. In this implementation, for example, a polarity change of the rotating magnetic component may indicate particular amount of rotation (e.g., one rotation) of the rotating magnetic component. This may further indicate a distance traveled by combining the amount of rotation with a thread distance to determine how far the component travels per rotation, for example.

In one implementation, a control device may be used to limit an amount of rotation (e.g., and distance traveled) of the rotating magnetic component (e.g., fastener and/or drive screw), for example, by mitigating the effects of the magnetic force applied to the rotating magnetic component when a predetermined amount of rotation (e.g., and/or distance traveled) has been met. As one example, a physician may indicate that the magnetic drive screw can be adjusted by five millimeters. In this example, the control device may shut off the magnetic force generation component (e.g., or shield the magnetic drive screw from the magnetic force) upon the sensing means identifying that the magnetic drive screw has traveled the desired five millimeters. In this way, for example, the desired distraction may be applied, while mitigating a chance that the growing rods may be over or under distracted.

In another implementation of the present invention, the device 300 may be removed from the pediatric patient upon reaching orthopedic maturity such that a different implant system could be utilized to fuse the spine as needed. In such a case, for example, the device 300 may be adaptable such that the rotating magnet (e.g., 602) may not need to be needed to loosen the fastener (e.g., 302). For example, the one or more fasteners of the device may be loosened with an appropriate tool (e.g., wrench or set screw driver) and external surgical instruments to remove the device, and provides increased flexibility and adaptation to benefit the patient. One significant difference from the prior art is the absence of a drive mechanism inside the shaft (e.g., 308). In one implementation, the exemplary device 300 may not comprise complicated gearing, springs, batteries, or other components to operate the device 300.

The present devices and systems, described herein, while described in detail for application with treatment of scoliosis can be applied to a variety of orthopedic and other medical treatment applications, including but not limited to, any application where set screws are utilized. Non-limiting examples may include the set screws being utilized in conjunction with bone plates, bone rods, or other screws. It can be used to treat a variety of conditions including without limitation, fractures or any bone deformity.

In another aspect, a magnet-based drive may be used to translate a member (e.g., rod) with respect to a member coupling component (e.g., rod holder). For example, the magnet-based drive mechanism described above (e.g., FIGS. 6-11), and used to rotationally translate a fastener in a rod holder, may also be used to linearly translate a member, with respect to the member coupler, that is engaged with the magnet-based drive.

Figure 19:
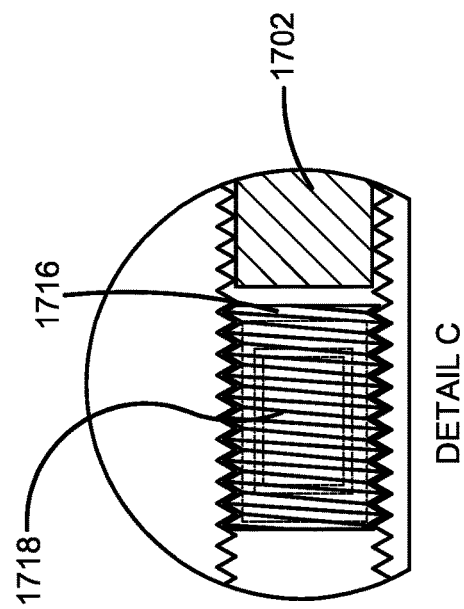
FIG. 19 is an enlarged view of a portion of FIG. 18.
Figure 18:
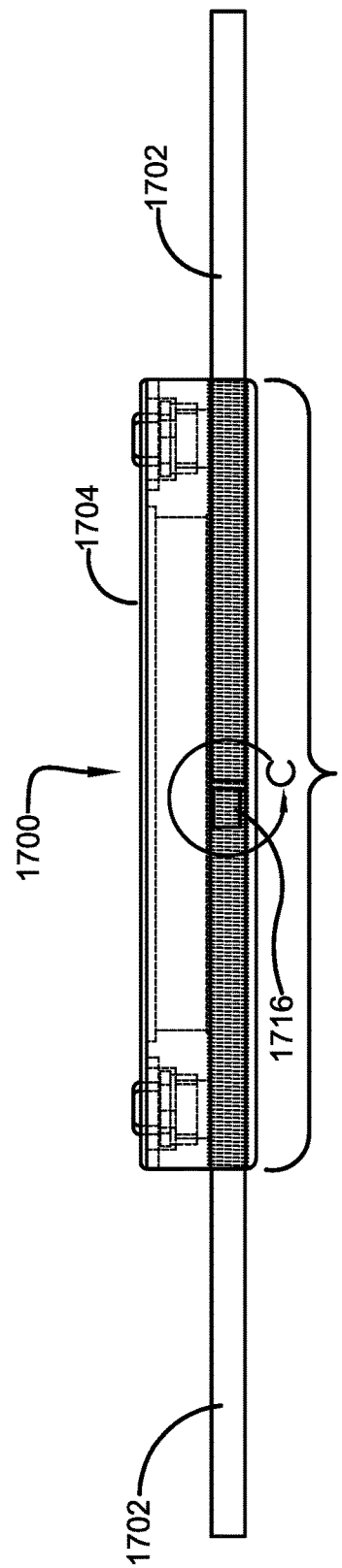
FIG. 18 is a cross sectional view of FIG. 17.
Figure 20:
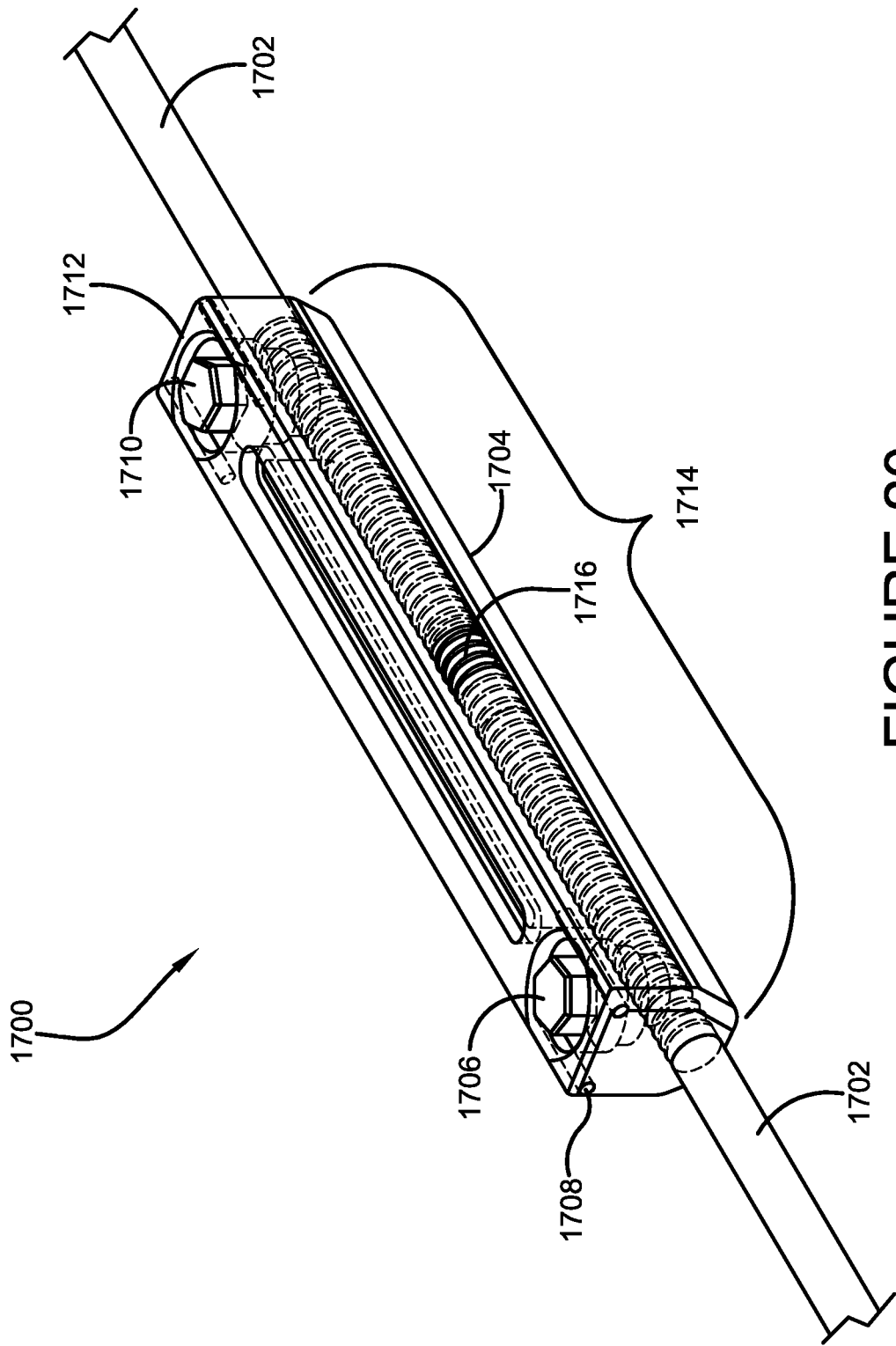
FIG. 20 is an example implementation of one or more portions of one or more systems described herein.
Figure 21:
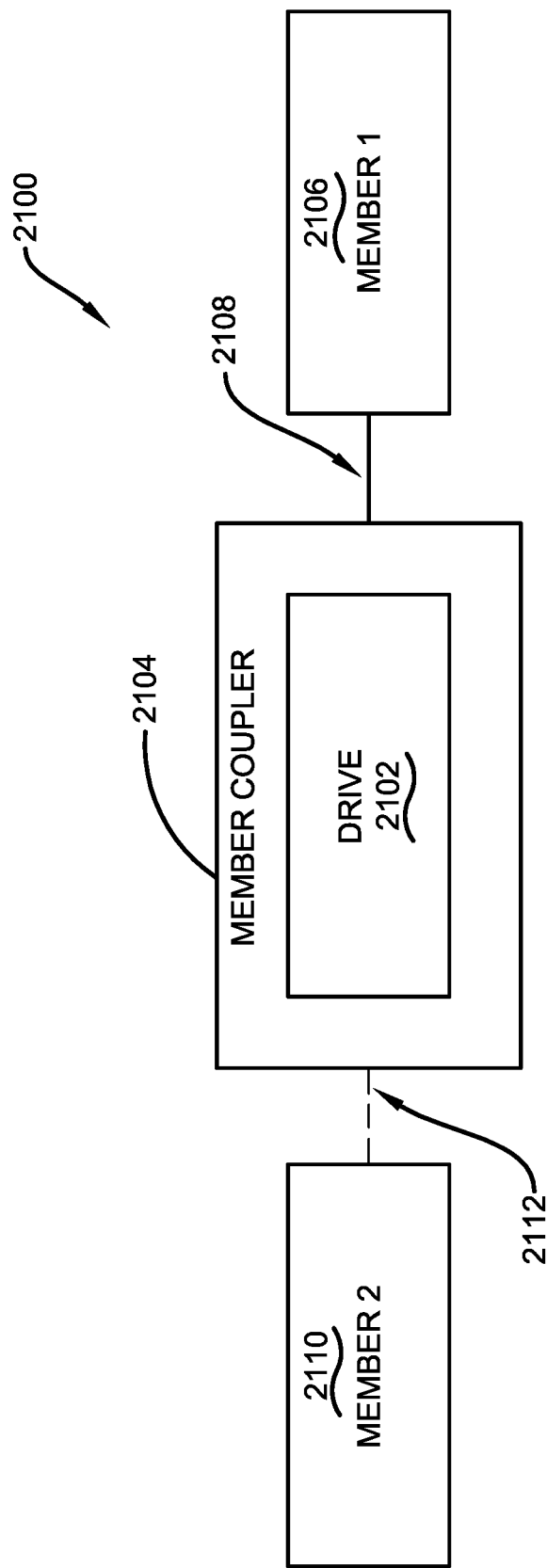
FIG. 21 is an example implementation of one or more portions of one or more systems described herein.

FIG. 21 is a component diagram illustrating an exemplary implementation 2100 of a system for translating a member with respect to a member coupler. In one implementation, (e.g., as described in more detail below in FIG. 17-20), a magnet-based drive 2102 (e.g., 1716 of FIG. 19, below) can comprise a magnet (e.g., 602 of FIGS. 6-11, 1718 of FIG. 19) engaged (e.g., fixedly) with a magnet collar (e.g., 704 of FIGS. 7-10) that engages an magnet engagement component (e.g., 904 of FIGS. 9A, 9C) of an inner surface (e.g., 902 of FIGURED 9A, 9C) of the magnet-based drive 2102. For example, as described above, the rotation of the magnet can result in the collar engaging the inner surface of the magnet-based drive 2102, thereby resulting in rotational translation of the magnet-based drive in the direction of rotation of the magnet.

In one implementation, in this aspect, the magnet-based drive 2102 may comprise or be operably coupled with a first screw thread, which, when rotated, can convert the resulting rotational translation to linear translation when threadedly engaged with a complementary second screw thread, such as disposed in a member coupler 2104. Further, in this implementation, for example, the linear translation of the magnet-based drive screw 2102 can result in linear translation of a member 2106, 2110 engaged with the magnet-based drive screw 2102.

In one implementation, a first member 2106 can be operably coupled 2108 with the member coupler 2104. For example, a means (e.g., 2108) for operably coupling the first member 2106 with the member coupler 2104 can comprise a threaded engagement. That is, for example, the first member 2106 may comprise male screw thread, disposed around its outer perimeter, and the member coupler 2104 may comprise complementary female screw thread disposed around its interior perimeter; and the first member 2106 and member coupler 2104 may be threadedly engaged to provide the operable coupling 2108. As another example, the first member 2106 may be slidably engaged with the member coupler 2104, where the outer dimensions of the first member 2106 are so dimensioned to appropriately fit in slidable engagement with the interior dimensions of the member coupler 2104.

In one implementation, the rotational translation of the drive 2102 can be converted into linear translation by way of the threaded engagement of the drive 2102 with the interior of the member coupler 2104. Further, in this implementation, the drive 2102 may be engaged with (e.g., abutted to, coupled with, etc.) the first member 2106, which is coupled with the member coupler 2104, such that linear translation of the drive 2102 results in proportional linear translation of the first member 2106. Additionally, in one implementation, a second member 2110 may be operably coupled 2112 (e.g., in a similar or different manner as the first member 2106) with the member coupler 2104, and can be configured to translate with the respect to the member coupler 2104 as a result of linear translation of the drive 2102.

One implementation, in this aspect, an exemplary growth rod apparatus 1700 is shown in FIGS. 17-20. In this implementation, one or more growing rods 1702 (e.g., members, such as 2106 and/or 2108 of FIG. 21) may be adjusted by a device method similar to that described above, such as a magnetic field generation component (e.g., 1502 in FIG. 15). In this implementation 1700, a rod holder 1704 may be provided (e.g., such as 308 of FIG. 3), which may be configured to hold the one or more growing rods 1702. Further, in this implementation 1700, a first magnet-based set screw 1706, such as described above (e.g., 302 of FIG. 3), may be rotationally engaged with a first end 1708 of the rod holder 1704, and configured to selectively engage the growing rod 1702, for example, when rotated down into the rod holder 1704. Additionally, a second magnet-based set screw 1710 (e.g., or a traditional set screw) may be rotationally engaged with a second end 1712 of the rod holder 1704, and configured to selectively engage the growing rod 1702, for example, when rotated down into the rod holder 1704.

In one implementation, a shaft portion 1714 of the rod holder 1704, which may be engaged with one or more of the growing rods 1702, can comprise internal threading (e.g., female threading). Further, a magnetic drive screw 1716 may be disposed in the shaft portion 1714. In one implementation, the magnetic drive screw 1716 may comprise a drive magnet 1718 (e.g., similar to 602 of FIG. 6) disposed therein. In one implementation, the drive magnet 1718 can be configured to be driven (e.g., rotated) using an external drive device, such as the magnetic field generation component described above (e.g., 1502 in FIG. 15), in a manner similar to that described above in FIGS. 2-16. That is, for example, a magnet collar (e.g., 702 of FIG. 7) may be fixedly attached to the drive magnet 1718, and the magnetic drive screw 1716 may comprise an internal magnet engaging component (e.g., 904 of FIG. 9A) disposed in opposing rotational engagement with the magnet collar of the drive magnet 1718. In this way, as described above, when an appropriate rotational magnetic force is applied to the magnetic drive screw 1716, the magnet collar of the drive magnet 1718 may apply rotational force to the magnet engaging component inside the magnetic drive screw 1716, for example, thereby causing the magnetic drive screw 1716 to rotate in accordance with the applied rotational magnetic force.

In one implementation, the magnetic drive screw 1716 may comprise external threading (e.g., male threading) that is configured to threadedly engage the internal threading of the shaft portion 1714 of the rod holder 1704. In this implementation, for example, magnetically rotating the magnetic drive screw 1716 may cause the magnetic drive screw 1716 to travel along the shaft portion 1714 of the rod holder 1704, with the direction of travel dependent upon a direction of rotation of the magnetic drive screw 1716 (e.g., and therefore the rotation and/or orientation of the magnetic force generation component 1502).

In one implementation, one or more of the growing rods 1702 may be engaged with the shaft portion 1714, for example, and secured in the rod holder 1704 by means of the first and/or second fasteners 1706, 1710. Further, in this implementation, when the growing rod 1702 is not secured to the rod holder 1704 (e.g., the fastener 1706 is loosened), the magnetic drive screw 1716 may be used to extend the growing rod 1702. For example, the magnetic drive screw 1716 can be magnetically rotated to cause the magnetic drive screw 1716 to engage an end of the growing rod 1702 disposed in the shaft portion 1714, such that the magnetic drive screw 1716 pushes at least a portion of the growing rod 1702 out of the shaft portion 1714. In this example, the fastener 1706 may then be tightened (e.g., magnetically) to secure the growing rod 1702 in the rod holder 1704 at a desired position.

As another example, when the magnetic drive screw 1716 is actuated, it is contemplated that the growing rod 1702 may translate in the rod holder 1704 between about 5 mm and about 20 mm per adjustment. For example, the one or more magnetic set screws 1706, 1710 can be loosened with the magnetic field generation component (e.g., 1502 in FIG. 15, in an appropriate orientation), which may cause the growing rod 1702 to loosen with respect to the rod holder 1704. Further, in this example, the magnetic field generation component can actuate the magnetic drive screw 1716, rotating the magnetic drive screw 1716 within the shaft portion 1714 of the rod holder 1704. The magnetic drive screw 1716 can apply force to the growing rod 1702, for example, thereby causing the growing rod 1702 to advance a desired distance in the rod holder 1704. In this example, once the desired adjustment is made, the one or more magnetic set screws 1706, 1710 may be tightened with the magnetic field generation component, securing the growing rod(s) 1702 in the rod holder 1704. Additionally, any devices and methodology chosen with sound engineering judgment may be utilized to obtain the desired distance of travel of the growing rod within the rod holder as long as the magnetic drive screw 1716 is directly or indirectly engaged with the growing rod 1702, and the drive magnet 1718 is actuated by the magnetic field generation component 1502.

FIGS. 22A, 22B and 22C are component diagrams illustrating an example of another implementation 2200 of an adjustable rod system, for example, that may be utilized in treating scoliosis (e.g., or some other skeletal and/or musculoskeletal-related disorder, disease, and/or injury). In this example implementation 2200, a first rod 2202 is selectively, slidably engaged with a rod holder 2204. That is, for example, the first rod 2202 may be slid into and out of the rod holder 2204, as desired, by a user (e.g., treating clinician). Further, in this implementation, a second rod 2210 may be engaged with the rod holder 2204. In one implementation, the second rod 2210 may be fixedly engaged with (e.g., welded, soldered, adhered to, formed with, fastened to) the rod holder 2204.

In another implementation, the second rod 2210 may be non-fixedly engaged with the rod holder 2204. In this implementation, a fastener 2212, such as a screw (e.g., a pedicle screw, or other appropriate fastener), may be used to selectively secure the non-fixed engagement of the second rod 2210 to the rod holder 2204. In one implementation, the fastener 2212 may comprise a magnetically controlled fastener device, such as 302 in FIGS. 3-7, described above. That is, for example, the example fastener 2212 may be tightened and or loosened by use of an external magnetic field, such as 1502 in FIGS. 15 and 16, described above.

The example implementation 2200 of the distracting rod system may comprise a drive mechanism 2206, configured to be driven back and forth along a central axis of the rod holder 2204 when subjected to an appropriate magnetic field. Further, the drive mechanism 2206 can be operationally engaged with the first rod 2202 at a first portion 2222, disposed at a first end (e.g., proximal end) of the first rod 2202. In this implementation, the first portion 2222 of the first rod 2202 may be configured to receive the drive mechanism 2206 in rotational engagement. Further, a second portion 2224 of the first rod 2202 may be configured to maintain the engagement of the drive mechanism 2206 with the first portion 2222 of the rod holder 2204. In one implementation, the second portion 2224 of the first rod 2202 may be formed with the first rod (e.g., formed together with). In another implementation, the second portion 2224 of the first rod 2202 may be fastened to (e.g., screwed into, adhered to, welded or soldered to, press fit to, etc.) the first rod 2202. As an example, the drive mechanism 2206 may first be coupled with (e.g., slid onto) the first portion 2222 of the first rod 2202, and the second portion 2224 of the first rod 2202 may subsequently be fastened to first rod 2202, such as to retain the drive mechanism 2206 on the first rod 2202.

As illustrated in FIGS. 22A and 22C, the drive mechanism 2206 can comprise a drive threaded portion 2220, which can be configured to threadedly engage with a holder threaded portion 2214 of the rod holder 2204. In one implementation, the drive threaded portion 2220 may comprise male-type threads configured to threadedly engage with female-type threads of the holder threaded portion 2214 of the rod holder 2204. In this way, for example, a rotation of the drive mechanism 2206 may result in translation (e.g., forward and/or backward) of the drive mechanism 2206 linearly within the rod holder 2204. Further, in this implementation, translation of the drive mechanism 2206 may also result in translation (e.g., in a same direction as the drive mechanism 2206) of the first rod 2202, which is operationally engaged with the drive mechanism 2206, relative to the rod holder 2204. As an example, rotation of the drive mechanism 2206 in a first rotational direction may result in the drive mechanism 2206, as well as the first rod 2202, being translated in a first linear direction in the rod holder 2204 (e.g., forward toward the rod holder 2204 opening). As another example, rotation of the drive mechanism 2206 in a second rotational direction may result in the drive mechanism 2206, as well as the first rod 2202, being translated in a second linear direction in the rod holder 2204 (e.g., rearward). In one implementation, the drive threaded portion 2220 (e.g., a threaded element) is thus operably disposed between the rod holder 2204 (e.g., a first member) and the first rod 2202 (e.g., a second member).

In one implementation, the drive threaded portion 2220 and/or the holder threaded portion 2214 may be configured to mitigate translation of the drive mechanism 2206 in one of the first linear direction or the second linear direction within the rod holder 2204. That is, for example, the configuration of the drive threaded portion 2220 and/or the holder threaded portion 2214 may appropriately allow translation of the drive mechanism 2206 in the first linear direction (e.g., forward), but may mitigate translation of the drive mechanism 2206 in the second linear direction (e.g., rearward). As an illustrative example, the threaded engagement of the drive threaded portion 2220 and/or the holder threaded portion 2214 may comprise an arrangement of thread teeth and/or thread valleys that readily allow the threads to rotate in the first rotational direction, resulting in translation in the first linear direction; but can mitigate the threads rotating in the second rotational direction (e.g., the thread's design allows the screw to move forward but not backward, without an extraordinary application of work or force).

In one implementation, the drive mechanism 2206 may comprise a magnet-based rotor 2208. Further, the rotor 2208 can comprise a magnet 2230 that is engaged with a magnet collar 2226 (e.g., 702 of FIG. 7). Additionally, the drive mechanism 2206 can comprise an inner surface 2232, a portion of which can be configured to selectively engage with the magnet collar 2226 of the rotor 2208.

As an example, as described in FIGS. 9A-D, 10A-D, and 11A-B, above, and with continued reference to FIGS. 22A, B, and C, the inner surface 2232 can comprise a magnet engaging component (e.g., 904 of FIG. 9C), such as an extension disposed in the inner surface 2232 of the drive mechanism 2206. In one implementation, the magnet engaging component of the inner surface 2232 may be formed with (e.g., formed together with) the drive mechanism 2206; and in another implementation, the magnet engaging component of the inner surface 2232 may be attached to the inner surface of the drive mechanism 2206. The magnet engaging component of the inner surface 2232 can be configured to selectively engage with the magnet collar 2226, such that an application of torque to the magnet 2230 that is engaged with the drive engaging component 2226 causes torque to be applied to the fastener drive mechanism 2206.

In one implementation, the drive engaging component 2226 may comprise a collar extension (e.g., 702 of FIG. 7), which extends from the drive engaging component 2226 (e.g., as a collar fixedly engaged with the magnet 2230). For example, the drive engaging component 2226 may comprise an annular shape configured to merely fit around the magnet 2230 in fixed engagement. In one implementation, the drive engaging component 2226 may be formed with (e.g., formed together with) the magnet 2230; in another implementation the drive engaging component 2226 may be attached (e.g., press fit, adhered, glued, welded, soldered, etc.) to the magnet 2230. Further, the drive engaging component 2226 can comprise the collar extension, which is configured to be disposed in opposing engagement with respect to the magnet engaging component of the inner surface 2232 of the drive mechanism 2206.

As one example, as a magnetic force (e.g., as the desired magnetic field) is applied to the magnet 2230, the magnet 2230 can translate in a rotational direction (e.g., in a first or second direction dependent on the rotation of the desired magnetic field, as described above), and the collar extension of the drive engaging component 2226 can engage the magnet engaging component of the inner surface 2232, which may cause the drive mechanism 2206 to translate in the same direction of rotation. In one implementation, the inner surface 2232 may comprise a track for the drive engaging component 2226 to improve engagement of the collar extension of the drive engaging component 2226 with magnet engaging component of the inner surface 2232, in order to provide the appropriate torque to the drive mechanism 2206.

In one aspect, when the magnetic force provided by the desired magnetic field causes the drive engaging component 2226 (e.g., the collar extension of the drive engaging component 2226) to engage the magnet engaging component of the inner surface 2232, the drive engaging component 2226 may rebound (e.g., bounce back from engagement), depending on an amount of rotational resistance extant for the drive mechanism 2206. In one implementation, upon the drive engaging component 2226 disengaging (e.g., bouncing away from) the magnet engaging component of the inner surface 2232, when the drive mechanism 2206 encounters a certain amount of rotational resistance (e.g., stops rotating), the drive engaging component 2226 can re-engage the magnet engaging component of the inner surface 2232, when the magnet 2230 is subjected to the desired magnetic field. In this implementation, when the drive engaging component 2226 re-engages the magnet engaging component of the inner surface 2232, a rotational hammering force may be applied to the drive mechanism 2206.

As an example, the magnetic force provided by the desired magnetic field can be reapplied to the drive engaging component 2226, causing it to re-contact the collar extension of the drive engaging component 2226 within the drive mechanism 2206. In this example, a repeated bounce-back and re-engagement action can cause a type of hammering effect between the collar extension and the magnet engaging component of the inner surface 2232. In this example, the hammering action may cause the drive mechanism 2206 to rotate, particularly when subjected to rotational resistance. In this way, for example, the drive mechanism may be translated linearly along the rod holder 2204 more effectively, particularly when subjected to an opposing linear force.

In one aspect, the rotational speed of the desired magnetic field may correlate to the amount of torque that can be generated by the rotational hammering force. In one implementation, increasing the rotational speed of the desired magnetic field (e.g., resulting from an increase in the rotation of the magnets 1604 in the magnetic field generation component 1502 of FIG. 16) may result in a proportional increase in the amount of torque applied to the drive mechanism 2206. As an example, increasing the torque may result in an increase in the amount of an opposing, axial linear force (e.g., to the first rod) that can be overcome by the drive mechanism 2206.

As an illustrative example, the first rod 2202 can be engaged with a first bone or bone portion, and the second rod 2210 can be engaged with a second bone or bone portion. In this example, translating the first rod 2202 linearly away from the second rod 2210, using the drive mechanism 2206, may result in an increase of the opposing, axial linear force to the first rod 2202 (e.g., pushing the first rod back toward the second rod). In this example, in this implementation, increasing the rotational speed of the desired magnetic field may increase the ability of the drive mechanism 2206 to overcome that increased opposing, axial linear force to the first rod 2202. This may allow the first rod 2202 to be translated further away from the second rod 2210 than without the increase to the rotational speed of the desired magnetic field.

In one implementation, in this aspect, empirical data may be used to determine the desired rotational speed of the magnetic field, for a particular treatment. As an example, empirical data may be gathered for spinal distraction forces associated with myriad patient age groups, comprising different body styles (e.g., dimensions, weights, musculature, skeletal arrangement, etc.). Further, in this example, empirical data of torque, and associated opposing, axial linear force that the torque can overcome, can be gathered for respective rotational speeds of the magnetic field. In this implementation, using the empirical data, recommended rotational speeds may be generated for respective patient age groups and/or patient body styles. As an example, a clinician may identify the age group and/or body style of a target patient, and may utilize a recommended magnetic field rotational speed to treat the target patient, by distracting the first rod a desired distance to satisfy the treatment.

Figure 23:
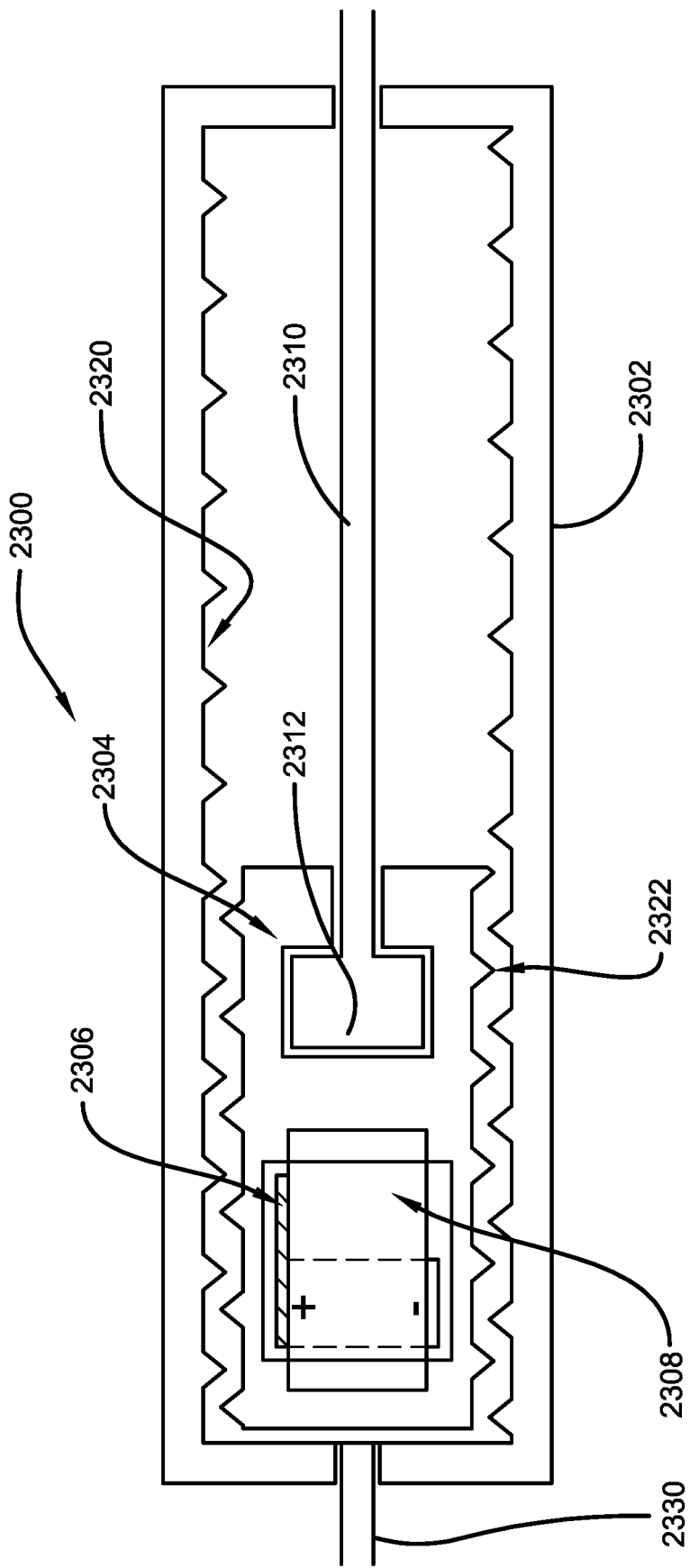
FIG. 23 is an example implementation of one or more portions of one or more systems described herein.

FIG. 23 is a component diagram illustrating an example of an implementation 2300 of a distracting rod system. The example implementation 2300 can comprise a rod holder 2302, a first rod 2310, and a second rod 2330. Further, the example implementation 2300 can comprise a drive mechanism 2304 operably engaged with the first rod 2310. In this implementation, as described in FIGS. 22A-C, the second rod 2330 may be fixedly engaged with the rod holder 2302, or the second rod 2330 may be non-fixedly engaged with the rod holder 2302.

Further, as described above in FIGS. 22A-C, the drive mechanism 2304 may be threadedly engaged with the rod holder 2302. In this implementation 2300, the drive mechanism 2304 can comprise first threads 2322 (e.g., male threads) and the rod holder may comprise complementary second threads 2320 (e.g., female threads). In one implementation, the threaded engagement may allow the drive mechanism 2304 to translate in a first linear direction (e.g., forward) and a second linear direction (e.g., rearward) in the rod holder 2302. As an example, such translation of the drive mechanism 2304 can result in corresponding translation of the first rod 2310. In one implementation, the drive threaded mechanism 2304 (e.g., a threaded element) is thus operably disposed between the rod holder 2302 (e.g., a first member) and the first rod 2310 (e.g., a second member).

Additionally, in one implementation, as described above, the first threads 2322 and second threads 2320 may be configured to allow rotational translation of the drive mechanism in a first direction, and may mitigate rotational translation of the drive mechanism in a second direction, for example, thereby allowing the drive mechanism 2304 to translate linearly in the first direction, but mitigating linear translation of the drive mechanism 2304 in the second direction.

In this implementation 2300, the first rod 2310 may comprise a rod hub 2312 that is configured to couple with the drive mechanism 2304 in rotational engagement. That is, for example, the drive mechanism 2304 may comprise a configuration that can effectively receive the rod hub 2312, and retain the rod hub 2312 in rotational engagement, such as during rotation and translation of the drive mechanism 2304 inside the rod holder 2302. In one implementation, the rod hub 2312 (e.g., and/or the drive mechanism) may comprise a bearing that is configured to facilitate the rotational engagement between the rod hub 2312 and the drive mechanism. For example, bearings are typically used to mitigate friction between two components disposed in rotational engagement. It will be appreciated that the example implementation 2300 is not limited to merely the example rotational engagement described herein. It is anticipated that those skilled in the art may devise alternate rotational engagement means that can mitigate friction, for example, such as an application of a friction resistance polymer coating on the rod hub 2312 and/or the engagement portion of the drive mechanism 2304.

In this implementation 2300, the drive mechanism 2304 may comprise a magnet-based rotor 2306 (e.g., 2208 as described above in FIGS. 22A-C). In a similar arrangement as described above in FIGS. 22A-C (e.g., and FIGS. 9A-D, 10A-D, and 11A-B), the rotor 2306 can comprise a magnet 2308 that is engaged with a magnet collar (not shown, for example, but similar to 2226 in FIG. 22C; and similar to 702 of FIG. 7). Additionally, the drive mechanism 2304 can comprise an inner surface (not shown, for example, but similar to 2232 of FIG. 22C), a portion of which can be configured to selectively engage with the magnet collar of the rotor 2306, as described above. In this implementation, the drive mechanism can be translated in a first direction and second direction, in a similar manner as described above in FIGS. 22A-C.

FIGS. 24A and 24B are component diagrams illustrating an example of one implementation 2400 of one or more portions of one or more systems described herein. In this example implementation 2400, a first rod 2406 may be selectively engaged with a rod holder 2402. Further, the first rod 2406 can be operably engaged with a drive engagement component 2404, at a first end of the first rod 2406. The drive engagement component 2404 can comprise a first engagement threaded portion 2418 that can be configured to threadedly engage with drive threads 2420 disposed on an outer surface of a magnetic drive component 2408. While FIG. 24A illustrates one example of a first engagement threaded portion 2418 of the drive engagement component 2404, it will be appreciated that the threaded portion may comprise myriad portions of the drive engagement component 2404, and is not limited to the example implementation. For example, it is anticipated that the threaded portion could comprise substantially the entire length of the drive engagement component 2404, merely sufficient length of the drive engagement component 2404 to effectively threadedly engage the magnetic drive component 2408, or some amount between these two examples. It is anticipated that those skilled in the art may devise alternate dimensions of the first engagement threaded portion 2418.

For example, the drive engagement component 2404 can comprise an open sided sleeve, having open, longitudinally extending slots (e.g., or a closed-sided sleeve, having no slots) that is sized to receive substantially the length and diameter of the magnetic drive component 2408. In this example, the proximal end of the drive engagement component 2404 can comprise the first engagement threaded portion 2418, which can threadedly engage with the distal end of the magnetic drive component 2408 when substantially all of the magnetic drive component 2408 is disposed in the drive engagement component 2404 (e.g., as in FIG. 24A). In this way, in this example, when torque is applied to the magnetic drive component 2408, thereby resulting in rotational translation, the drive engagement component 2404 may be linearly translated from the distal end of the magnetic drive component 2408 toward the proximal end of the magnetic drive component 2408 by way of the threaded engagement. Additionally, in this example, the linear translation of the drive engagement component 2404 can result in the linear translation of the first rod 2406 that is coupled with the drive engagement component 2404. In one implementation, the threaded magnetic drive component 2408 (e.g., a threaded element) is thus operably disposed between the rod holder 2402 (e.g., a first member) and the first rod 2406 (e.g., a second member).

In one implementation, as described above, the torque may be applied to the magnetic drive component 2408 by way of a magnet-based rotor 2422 (e.g., 2208 in FIGS. 22A-C, and 2306 in FIG. 23). In this implementation 2400, the magnet-based rotor 2422 disposed in the magnetic drive component 2408 (e.g., as described in FIGS. 22A-C and 23, and FIGS. 9A-D, 10A-D, and 11A-B) can comprise a magnet 2412 that is coupled with (e.g., fixedly) a magnet collar 2414. Additionally, the magnetic drive component 2408 can comprise an inner surface (not shown, for example, but similar to 2232 of FIG. 22C), a portion of which can be configured to selectively engage with the magnet collar of the rotor 2306, as described above. In this implementation, the magnetic drive component 2408 can be rotationally translated in a first direction and/or second direction, in a similar manner as described above in FIGS. 22A-C.

Further, in this implementation, for example, the rotational translation of the threaded magnetic drive component 2408 can result in a corresponding linear translation of the first engagement threaded portion 2418 of the drive engagement component 2404, based on a configuration of the mated threads. In one implementation, the threaded engagement between the drive threads 2420 and the threads of the first engagement threaded portion 2418 may allow the magnetic drive component 2408 to translate the drive engagement component 2404 in a first linear direction (e.g., forward) and a second linear direction (e.g., rearward) in the rod holder 2402. Additionally, in one implementation, as described above, the threaded engagement between the drive threads 2420 and the threads of the first engagement threaded portion 2418 may be configured to merely allow rotational translation of the magnetic drive component 2408 in a first direction, and may mitigate rotational translation of the magnetic drive component 2408 in a second direction, for example, thereby allowing the drive engagement component 2404 to translate linearly in the first direction, but mitigating linear translation of the drive engagement component 2404 in the second direction.

In this example implementation 2400, a second rod 2410 may be engaged with the rod holder 2402. In one implementation, the second rod 2410 may be fixedly engaged with (e.g., welded, soldered, adhered to, formed with, fastened to) the rod holder 2402. In another implementation, the second rod 2410 may be non-fixedly engaged with the rod holder 2402. In one implementation, a fastener 2416, such as a screw (e.g., a pedicle screw, or other appropriate fastener), may be used to selectively secure the non-fixed engagement of the second rod 2410 to the rod holder 2402. In one implementation, the fastener 2416 may comprise a magnetically controlled fastener device, such as 302 in FIGS. 3-7, described above. That is, for example, the example fastener 2416 may be tightened and or loosened by use of an external magnetic field, such as 1502 in FIGS. 15 and 16, described above.

FIGS. 25A and 25B are component diagrams illustrating an example of one implementation 2500 of one or more portions of one or more systems described herein. In this implementation 2500, a rod holder 2540 can comprise a first sleeve 2502 at a first end of the rod holder 2540; and a second sleeve 2504 at a second end of the rod holder 2540. Further, in this implementation 2500, a first rod 2510 can be operably coupled with the first sleeve 2502, at the first end, and a second rod 2512 can be operably coupled with the second sleeve 2504 at the second end. Additionally, in this implementation 2500, the first sleeve 2502 can be slidably engaged with the second sleeve 2504.

As an illustrative example (e.g., as demonstrated by the FIGS. 25A and B), the first sleeve 2502 and second sleeve 2504 may slide together to form the rod holder 2540; and, linearly sliding the first and second sleeves 2502, 2504 toward each other can shorten the rod holder 2540, while linearly sliding the first and second sleeves 2502, 2504 away from each other may lengthen the rod holder 2540. Further, in this example, sliding the first sleeve 2502 linearly away from the second sleeve 2504 may result in an increase in distance between the first rod 2510 and the second rod 2512. Conversely, in this example, sliding the first sleeve 2502 linearly toward the second sleeve 2504 may result in a decrease in distance between the first rod 2510 and the second rod 2512. That is, for example, an increase in overall length (e.g., from a distal end of the first rod 2510 to a distal end of the second rod 2512) of the example implementation 2500 of a distraction device may be achieved by sliding the first sleeve 2502 away from the second sleeve 2504.

In the example implementation 2500, first sleeve 2502 is operably coupled with (e.g., or comprises) a first drive engagement component 2506, and the second sleeve 2504 is operably coupled with (e.g., or comprises) a second drive engagement component 2508. Further, in this implementation, the respective drive engagement components 2506, 2508 comprise a second engagement threaded portion 2520. In one implementation, the second engagement threaded portion 2520 of the first drive engagement component 2506 can comprise a second screw thread configuration 2526, which can be different than a fourth screw thread configuration 2528 of the second engagement threaded portion 2520 of the second drive engagement component 2508. That is, for example, the second screw thread 2526 of the second engagement threaded portion 2520 of the first drive engagement component 2506 may comprise a right-handed screw thread, and the fourth screw thread 2528 of the second engagement threaded portion 2520 of the second drive engagement component 2508 may comprise a left-handed screw thread.

In the example implementation 2500, a magnetic drive component 2514 can comprise a first drive end 2516 and a second drive end 2518. In this implementation, the first drive end 2516 may comprise a first screw thread 2522 (e.g., comprising a right-handed configuration) disposed on the outer surface, and the second drive end 2518 may comprise a third screw thread 2524 (e.g., comprising a left-handed configuration) disposed on the outer surface. In one implementation, the first screw thread 2522 can be configured to threadedly engage with the second screw thread 2526 disposed on the first drive engagement component 2506. Further, in one implementation, the third screw thread 2524 can be configured to threadedly engage with the fourth screw thread 2528 disposed on the second drive engagement component 2508. In this way, for example, when the magnetic drive component 2514 is rotationally translated, the rotational translation can be converted into linear translation of the respective drive engagement components 2506, 2508, where the first and second drive engagement components can be translated in opposite directions.

In one implementation, as described above (e.g., in FIGS. 22-24), the magnetic drive component 2514 of FIGS. 25A and 25B can comprise a magnet-based rotor (not shown), which can be configured to apply torque to the magnetic drive component 2408 by way of a drive magnet coupled with a magnet collar 2414. Further, as described above, the applied torque can result in rotational translation of the magnetic drive component 2514, which can be converted to linear translation of the respective first and second drive engagement components 2506, 2508, by way of their threaded engagements with the respective first and second drive ends 2516, 2518. In this implementation, the linear translation of the respective first and second drive engagement components 2506, 2508 can result in linear translation of the respective first and second rods 2510, 2512 is opposite directions, for example, thereby resulting in distraction or retraction of the example device 2500.

Figure 26:
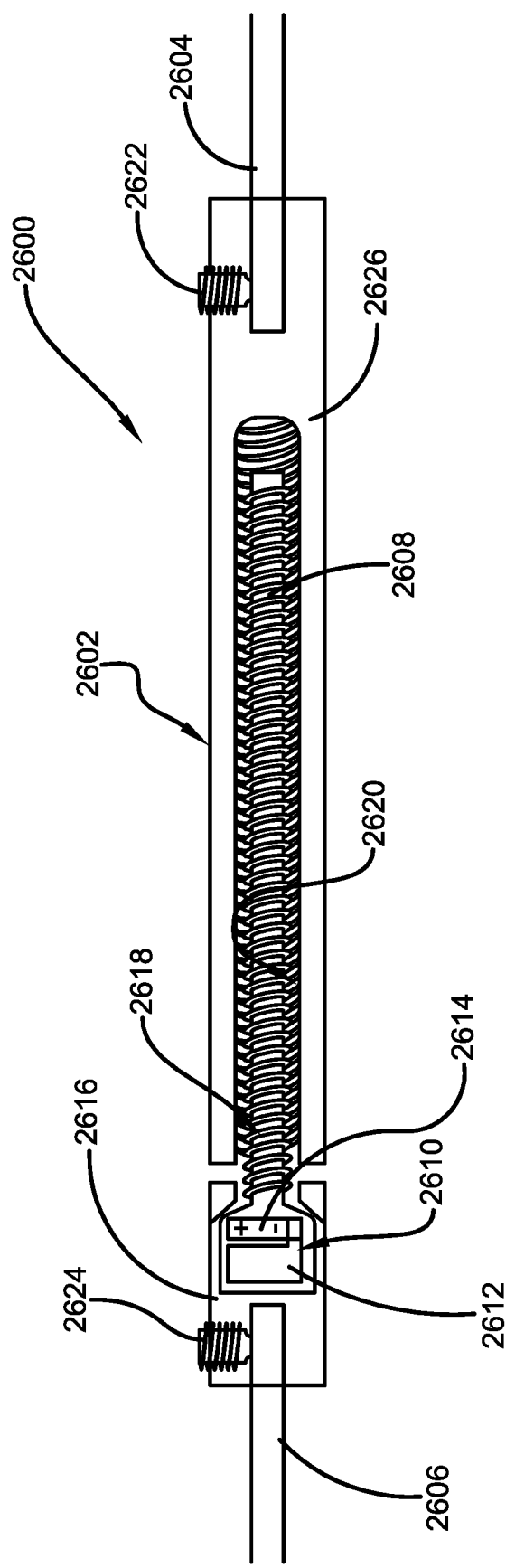
FIG. 26 is an example implementation of one or more portions of one or more systems described herein.

FIG. 26 is a component diagram illustrating an example implementation 2600 of one or more portions of one or more systems described herein. In this implementation 2600, a second portion 2626 of a rod coupler 2602 is operably engaged with a second rod 2604. In this implementation 2600, the second rod 2604 may be selectively, fixedly engaged with the second portion 2626 of the rod coupler 2602 using a second fastener 2622 that is configured to selectively, fixedly couple the second rod 2604 with the second portion 2626 of the rod coupler 2602. As an example, the second fastener 2622 can comprise a screw thread fastener that can be threaded into a complementary threaded opening in the second portion 2626 of the rod coupler 2602 to engage the second rod 2604. In this example, the second fastener 2622 may fixedly hold the second rod 2604 in a pressure and friction-based engagement against an interior wall of a shaft of the second portion 2626 of a rod coupler 2602 that is configured to receive the second rod 2604.

In the exemplary implementation 2600, a first rod 2606 is operably engaged with a first portion 2616 of the rod coupler 2602. In this implementation 2600, the first rod 2606 may be selectively, fixedly engaged with the first portion 2616 of the rod coupler 2602 using a first fastener 2624 that is configured to selectively, fixedly couple the first rod 2606 with the first portion 2616 of the rod coupler 2602. As an example, as described above for the second fastener 2622, the first fastener 2624 can comprise a screw thread fastener that can be threaded into a complementary threaded opening in the first portion 2616 of the rod coupler 2602 to engage the first rod 2606 with the first portion 2616 of the rod coupler 2602. In another implementation, the first rod 2606 may be non-selectively, fixedly engaged with the first portion 2616 of the rod coupler 2602. For example, the first rod 2606 may be formed with (e.g., cast, milled, shaped, pressed, etc.) the first portion 2616 of the rod coupler 2602. As another example, the first rod 2606 may be fixedly coupled to (e.g., soldered, welded, brazed, adhered, etc.) the first portion 2616 of the rod coupler 2602.

The exemplary device 2600 further comprises a dimensioning rod 2608 that can be configured to alter the dimensions of the device 2600. In one implementation, the dimensioning rod 2608 may be used to increase a length of the device 2600, and/or to decrease the length of the device 2600. For example, the dimensioning rod 2608 may be used to increase a distance between the second portion 2626 of the rod coupler 2602 and the first portion 2616 of the rod coupler 2602, thereby increasing the distance between the second rod 2604 and first rod 2606, resulting in an increase in the length of the device as measured from the distal ends of the respective first and second rods 2604, 2606. As another example, the dimensioning rod 2608 may be used to decrease a distance between the second portion 2626 of the rod coupler 2602 and the first portion 2616 of the rod coupler 2602, thereby decreasing the distance between the second rod 2604 and first rod 2606, resulting in an decrease in the length of the device as measured from the distal ends of the respective first and second rods 2604, 2606.

In one implementation, at least a portion of the dimensioning rod 2608 can comprise rod screw thread 2618 (e.g., male-type thread), disposed on the outer surface of the dimensioning rod 2608, and that is configured to threadedly engage with complementary coupler screw thread 2620 (e.g., female-type thread) disposed on an interior wall of the second portion 2626 of the rod coupler 2602. In one implementation, the second portion 2626 of the rod coupler 2602 may be configured with a shaft dimensioned to receive the dimensioning rod 2608, such as in threaded engagement. As an example, the threaded engagement of the dimensioning rod 2608 with the second portion 2626 of the rod coupler 2602 may be configured to convert a rotational translation of the dimensioning rod 2608 into a linear translation of the dimensioning rod 2608 longitudinally within the shaft of the second portion 2626 of the rod coupler 2602 (e.g., linearly left and right in the FIG. 26). In one implementation, the threaded dimensioning rod 2608 (e.g., a threaded element) can be thus operably disposed between the second portion 2626 of the rod coupler 2602 (e.g., a first member) and the first portion 2616 of the rod coupler 2602 (e.g., a second member).

In one implementation, the threaded engagement of the dimensioning rod 2608 with the second portion 2626 of the rod coupler 2602 may be configured to allow unhindered linear translation of the dimensioning rod 2608 in a first direction, with respect to the second portion of the rod coupler 2602, but also configured to mitigate linear translation of the dimensioning rod 2608 in a second direction, with respect to the second portion 2626 of the rod coupler 2602. That is, for example, the threaded configuration may provide normal linear translation of the dimensioning rod 2608 in a direction that increases the length of the exemplary device 2600, but limits or restricts linear translation of the dimensioning rod 2608 in a direction that decreases the length of the exemplary device 2600.

In the exemplary implementation 2600, the dimensioning rod is fixedly engaged with a magnetic drive component 2610. In this implementation, the magnetic drive component 2610 comprises a drive magnet 2614 and a magnet collar 2612. As described above (in FIGS. 9-11 and 17-25), the magnetic drive component 2610 can further comprise a magnet engagement component (e.g., 904 of FIGS. 9A, 9C), such as disposed on an inner surface (e.g., 902 of FIGS. 9A, 9C) of the magnetic drive component 2610. As described above, for example, the rotation of the drive magnet 2614 (e.g., when exposed to the desired magnetic field) results in the magnet collar 2612 engaging with the magnet engagement component disposed on an inner surface of the magnetic drive component 2610. In this example, the rotation of the magnet can result in the rotational translation of the magnetic drive component 2610, which may be converted to the linear translation of the dimensioning rod 2608, as described above.

In one aspect, one or more portions of the devices and systems described herein (e.g., in FIGS. 21-26) may be attached to a bone, for example, in an effort to provide treatment for a condition affecting the patient. In one implementation, the distal end (e.g., or another portion) of the first member (e.g., 2106, 2202, 2310, 2406, 2510, 2604) may be attached to a first bone (e.g., a portion of the spine, ribcage, or other target bone), using conventional or newly developed bone attachment techniques, devices, and systems (e.g., pedicle screws, clamps, etc., as illustrated in FIG. 2). Further, in one implementation, the distal end (e.g., or another portion) of the second member (e.g., 2110, 2210, 2340, 2410, 2512, 2506) may be attached to a second bone, using similar conventional or newly developed bone attachment techniques, devices, and systems. Additionally, in one implementation, at least a portion of the member holder (e.g., 2104, 2204, 2302, 2402, 2540, 2602) may be attached to the second bone (e.g., or a third bone), using similar conventional or newly developed bone attachment techniques, devices, and systems.

Figure 27:
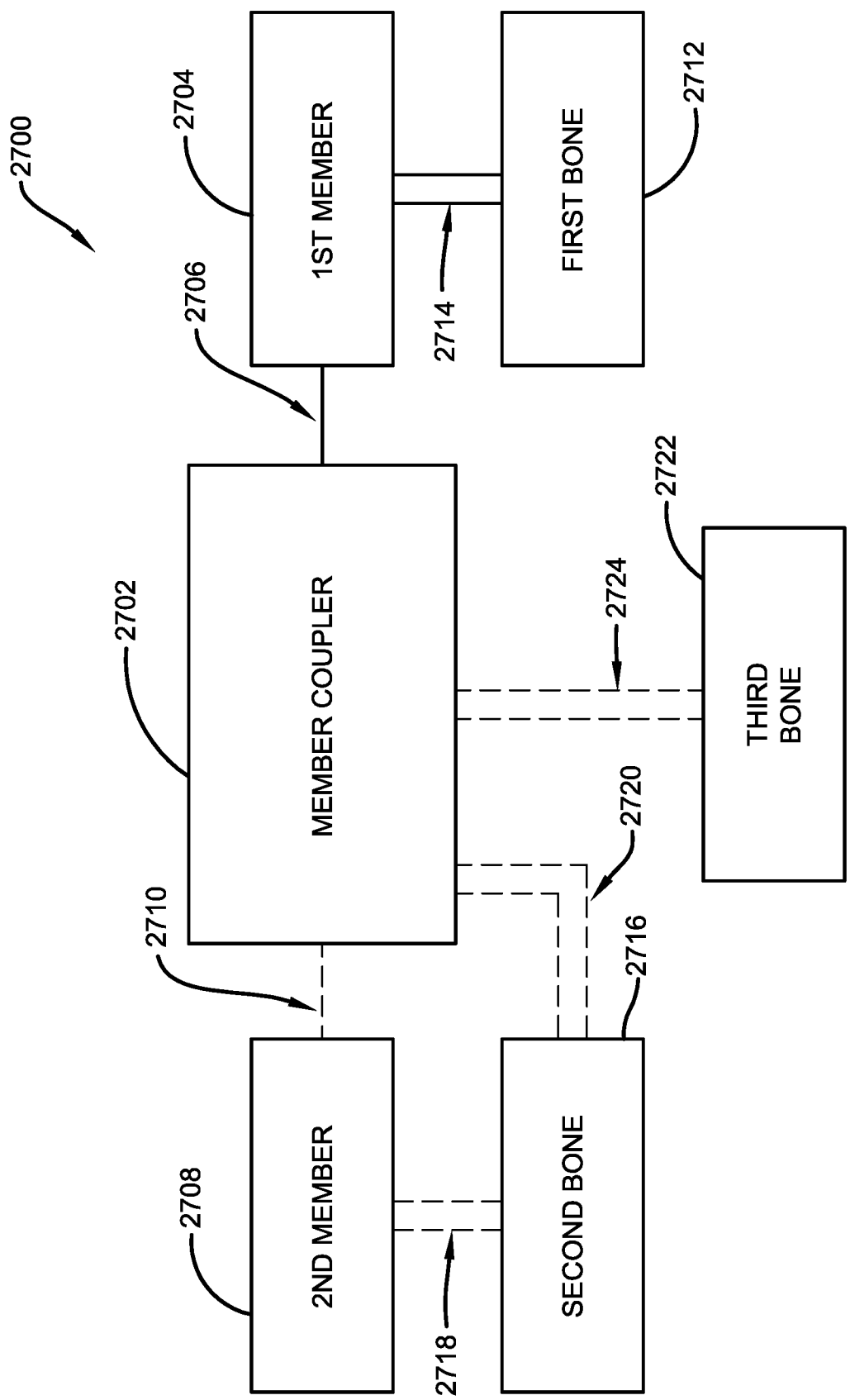
FIG. 27 is an example implementation of one or more portions of one or more systems described herein.

As an illustrative example, FIG. 27 is a component diagram illustrating an exemplary implementation 2700 of one or more portions of the systems and devices described herein. In this implementation 2700, a first member 2704 (e.g., rod, plate, bone engagement component, etc.) can be operably coupled 2706 (e.g., 2108 of FIG. 21) with a member coupler 2702 (e.g., comprising a magnet-based drive, such as 2102 of FIG. 21). Further, in this implementation, the first member 2704 can be fixedly engaged 2714 (e.g., selectively) with a first bone 2712 (e.g., or bone portion). As an example, as described above (e.g., in FIGS. 1, 2, 14 and 21) the first member may be fixed to the first bone 2712 by way of a fastener system, such as using pedicle screws, bone screw, clamp and/or another orthopedic attachment device.

In one implementation, a second member 2708 (e.g., rod, plate, bone engagement component, etc.) can be operably coupled 2710 (e.g., 2112 of FIG. 21) with the member coupler 2702. Further, in this implementation, the second member 2708 can be engaged with 2718 a second bone 2716 (e.g., or bone portion), using similar conventional or newly developed bone attachment techniques, devices, and systems as described above. Additionally, in one implementation, at least a portion of the member coupler 2702 may be engaged with 2720 the second bone (e.g., or engaged with 2724 a third bone 2722 or bone portion), using similar conventional or newly developed bone attachment techniques, devices, and systems.

Figure 15:
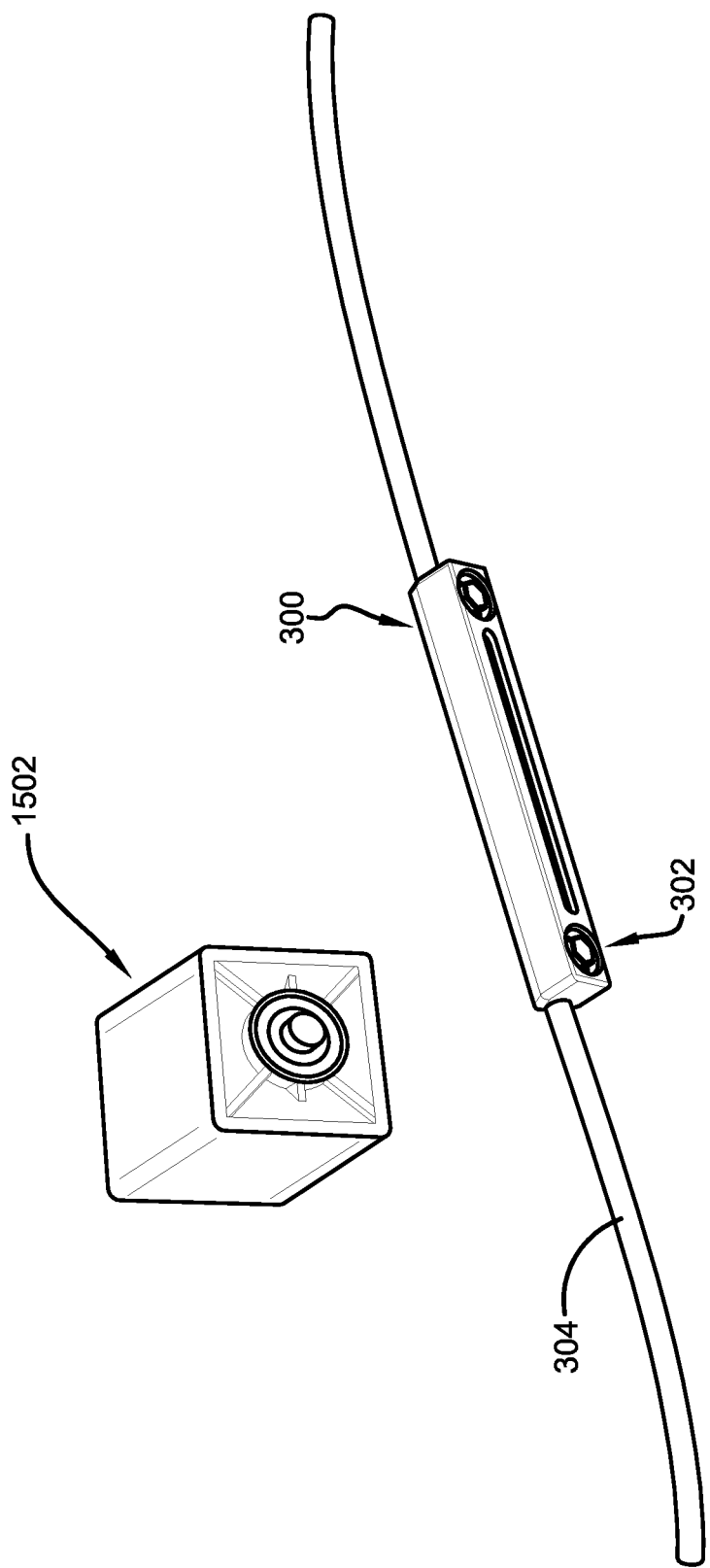
FIG. 15 is a component diagram illustrating a perspective view of an example implementation of one or more portions of one or more systems described herein.
Figure 17:
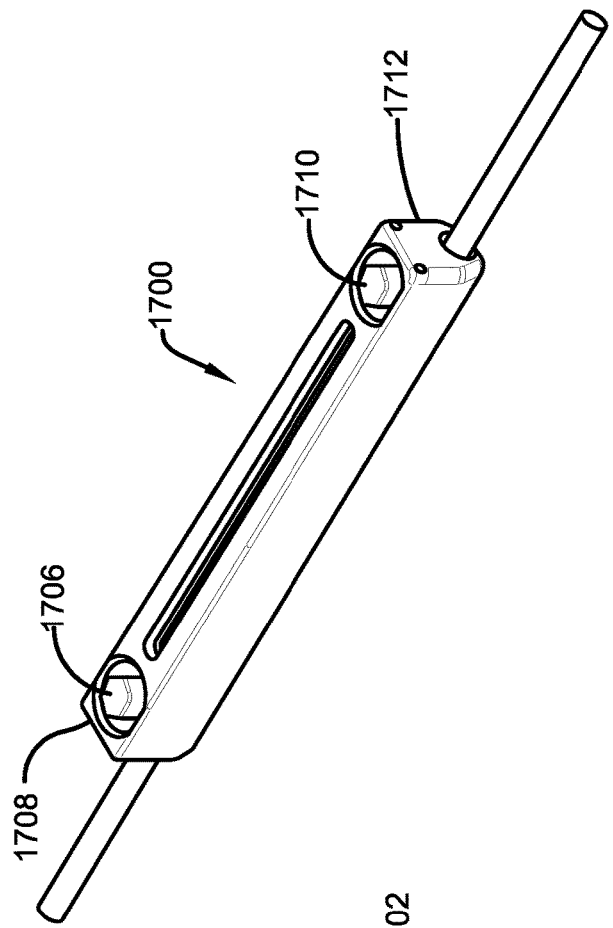
FIG. 17 is an example implementation of one or more portions of one or more systems described herein.
Figure 28:
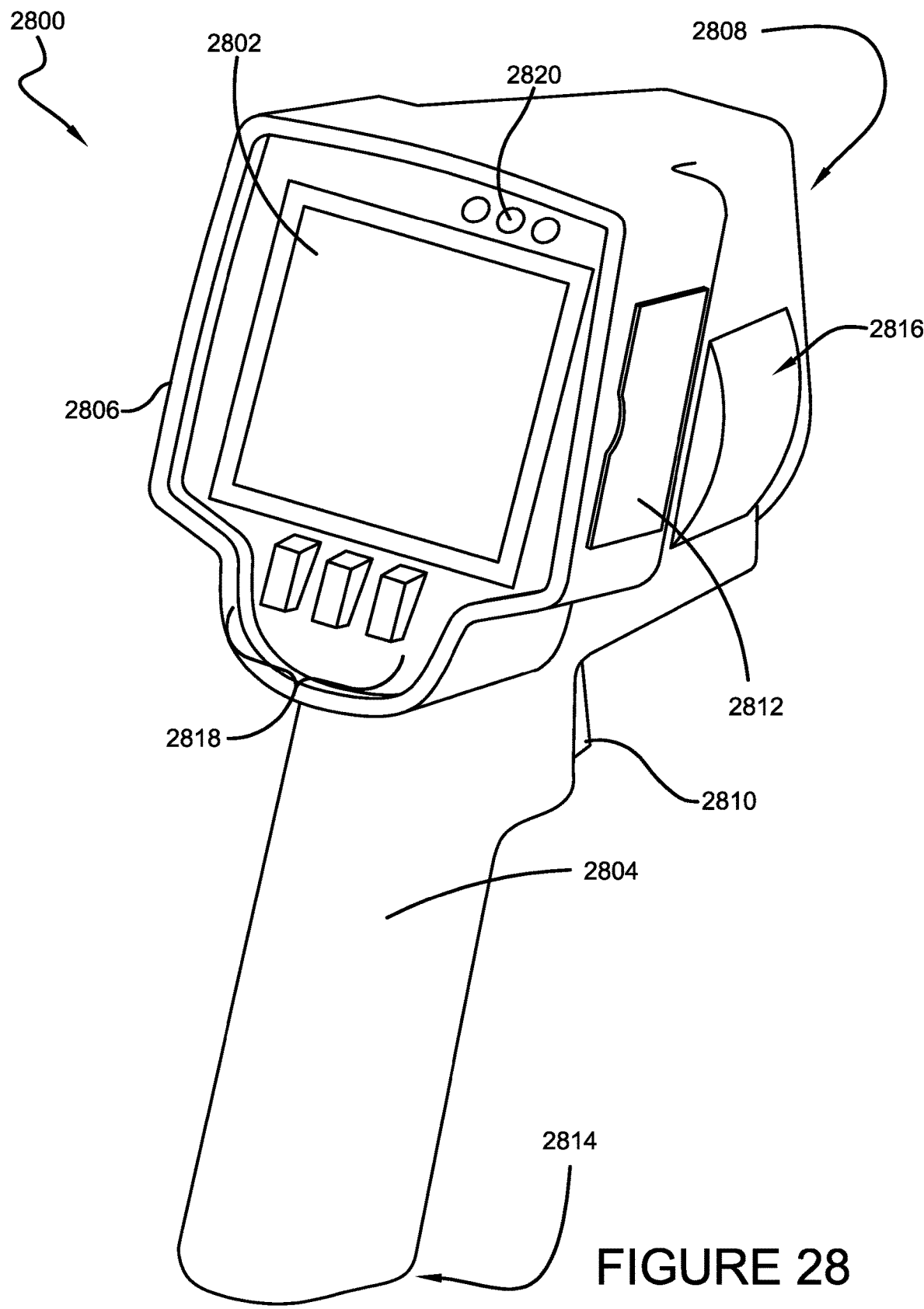
FIG. 28 is an example implementation of one or more portions of one or more systems described herein.
Figure 29:
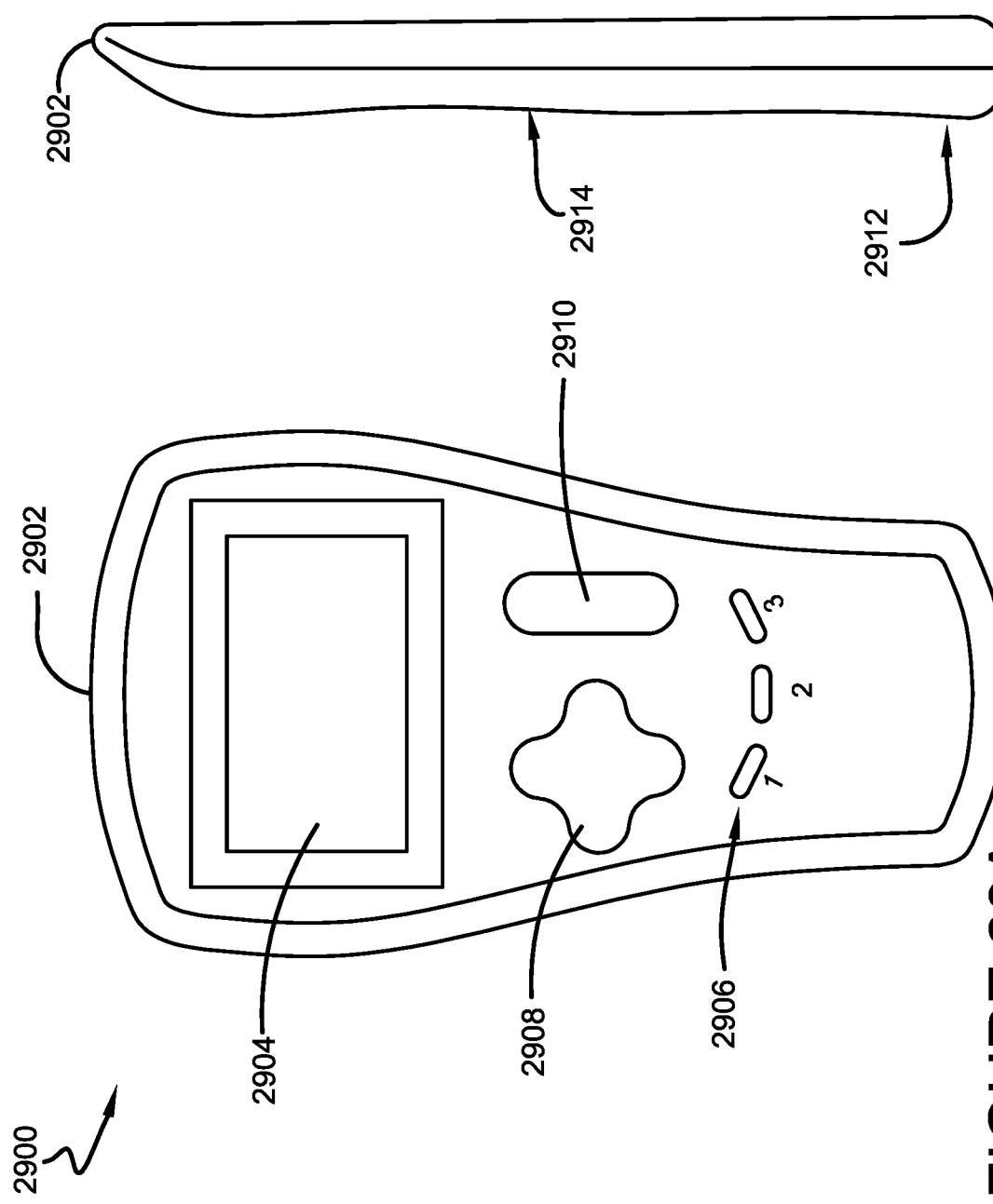
FIGS. 29A and 29B are component diagrams illustrating various views of an example implementation of one or more portions of one or more systems described herein.
Figure 30:
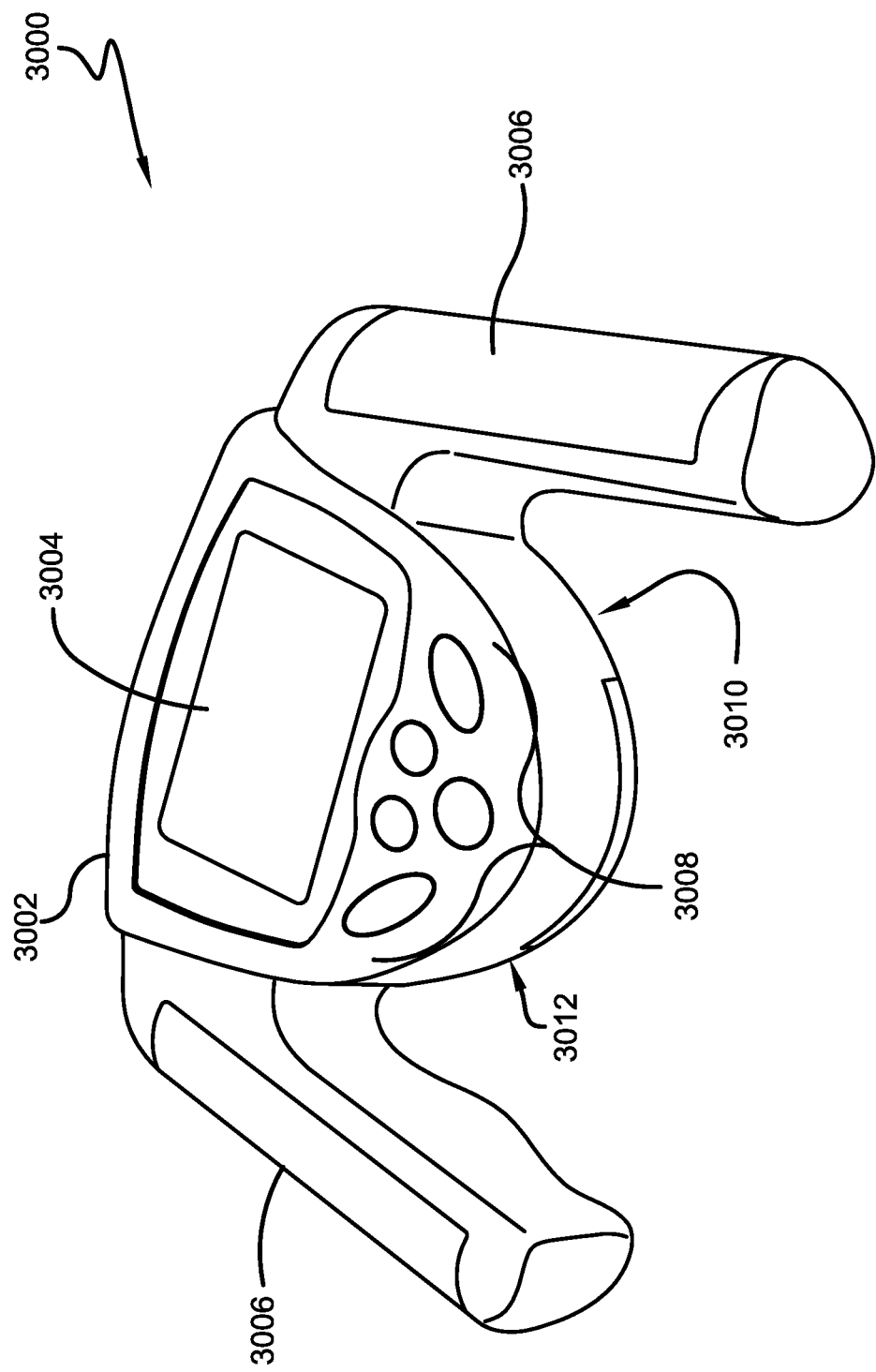
FIG. 30 is an example implementation of one or more portions of one or more systems described herein.

In one aspect, a desired magnetic field may be generated by a magnetic field generation component (e.g., 1502 of FIG. 15). As an example, the magnetic field generation component may generate the desired magnetic field, which, when placed in proximity to a drive magnet (e.g., 602, 1718, 2230, 2308, 2412, 2514, 2614) can result in rotation of the drive magnet in a desired rotational direction (e.g., based at least upon a configuration of the desired magnetic field). FIGS. 28-30 are component diagrams illustrating example implementations 2800, 2900, 3000 of devices that may be used to generate the desired magnetic field.

In FIG. 28, the example device 2800 comprises a housing 2806 that can be configured to appropriately house components of the device 2800. Further, the example device can comprise a display 2802, such as a liquid crystal display (LCD) monitor, or the like, on which may be displayed operational parameters, operational feedback, and/or operational alerts, for example. In this way, for example, an operator of the device 2800 may be provided with visual information as necessary. Further, the example, device 2800 may comprise an operator engagement component 2804, such as a handle or grip, which can be used by the operator to manipulate the device 2800.

In one implementation, the operator engagement component 2804 may be configured with a first internal compartment 2814 (e.g., accessed by a hatch from the outside) that can be used to house a power source (e.g., batteries), for example, for use of the device in a portable setting (e.g., without connecting to an external power source, such as an electrical outlet). In another implementation, the example device 2800 may comprise a second internal compartment 2812 (e.g., accessed by a hatch from the outside) that can be configured to house the power source. In another implementation, the second internal compartment 2812 may (also) be configured to receive external components, such as external memory (e.g., memory card), external inputs (e.g., connections to external devices, such as universal serial bus connections), and more.

The example device 2800 may comprise one or more inputs 2818, which are configured to provide input for the device 2800, such as a power switch/button, a manual safety switch/button, and/or a data input component. As an example, the example device 2800 may comprise a power switch that can be used to power on and off the device; may comprise a manual safety switch that can be activated in order to operate the device; and may comprise one or more data input components (e.g., buttons or keys) that can be used to input appropriate data for device operation. Further, the exemplary device 2800 may comprise one or more alert indicators 2820, such as photon emitters (e.g., light emitting diodes), that may be used to provide particular alerts associated with the respective indicators (e.g., faults, operational conditions, etc.). As an example, a yellow light may indicate to the operator that the device is approaching a set force application, and/or a set distraction/retraction distance threshold. As another example, a red light may indicate to the operator that the device has reached a set force application, and/or a set distraction/retraction distance threshold. Additionally, as an example, a green light may indicate to the operator that the device is ready for normal operation.

The exemplary device 2800 may comprise a magnetic field activator 2810 (e.g., trigger), which may comprise a manual switch configured to be activated by an operator. In one implementation, the magnetic field activator 2810 can comprise a type of dead-man's switch, which is configured to operate merely when the operator applies pressure to the activator. In one implementation, operation of the example device 2800 may necessitate substantially concurrent activation of the magnetic field activator 2810 and a manual safety switch/button 2818.

The exemplary device 2800 may also comprise a magnetic field generation component 2808. The magnetic field generation component 2808 can be disposed within the device housing 2806 at a location that may be placed proximate to a target drive magnet, for example, disposed inside a device used in adjustable rod system (e.g., FIGS. 3-3-15 and 18-27), which may be implanted in a patient. As an example, a distraction osteogenesis device used to treat a skeletal disorder may be attached to one or more bones of a patient, under the patient's dermal layer. In this example, the portion of the example device 2800 comprising the magnetic field generation component 2808 may be placed proximate to (e.g., adjacent to, against, within a desired distance of) the patient's outer skin layer and operated in order to activate the magnetic driver component disposed in the distraction osteogenesis device (e.g., for distraction and/or retraction of members fixed to the patient's bone(s)).

In one implementation, the example device 2800 may comprise a data output component 2816. In this implementation, for example, the data output component 2816 may comprise a printer configured to print a label (e.g. for attaching to a patient file) that indicates the treatment parameters and/or event data, including, but not limited to, patient name, time stamp, force applied, distance of distraction/retraction, etc. In another implementation, the data output component 2816 can comprise another data output apparatus configured to provide output of the event data.

FIGS. 29A and 29B are component diagrams illustrating another example implementation of a device 2900 that may be used to generate the desired magnetic field. In this example, the device 2900 can comprise a housing 2902 configured to house the components of the device 2900 and to be held by an operator, a display 2904, and one or more input components 2906, 2908, 2910, which may be similar to those described above. Further, the example device 2900 may comprise one or more internal compartments 2912, which may be used to house a power supply (e.g., and/or power supply connection), and/or may comprise data connections, and memory connections, similar to those described above, which can be used for data input, storage, and/or data output.

Additionally, the exemplary device 2900 can comprise a magnetic field generation component 2914. As described above, in one implementation, the magnetic field generation component 2914 can be disposed within the device housing 2902 at a location that may be placed proximate to the target drive magnet, which may be implanted in a patient.

FIG. 30 is a component diagram illustrating yet another example implementation of a device 3000 that may be used to generate the desired magnetic field. In this example implementation, the device 3000 can comprise a housing 3002 configured to house the components of the device 2900, a display 3004, and one or more input components 3008, which may be similar to those described above. Further, the example device 3000 can comprise one or more operator engagement components 3006 (e.g., handles), which may be used by the operator to manipulate the device 3000.

Additionally, the example device 3000 may comprise one or more internal compartments 3012, which may be used to house a power supply, and/or may comprise data connections, and memory connections, similar to those described above, which can be used for data input, storage, and/or data output. The exemplary device 3000 can also comprise a magnetic field generation component 3010, which can be disposed within the device housing 3002 at a location that may be placed proximate to the target drive magnet, which may be implanted in a patient.

In one aspect, a magnetic field generation component (e.g., 1502 of FIG. 15, 2800 of FIG. 29, 2900 of FIG. 29, and 3000 of FIG. 30) may be configured to control (e.g., automatically, programmatically, and/or manually) relevant parameters for appropriate magnetic field generation (e.g., to achieve a desired treatment result of a target magnet-based distraction/retraction device). In one implementation, translation force, translation displacement, and/or translation rate may be controlled by the magnetic field generation component, amongst other parameters. Viewed alternately, generation of the magnetic field may be controlled by the magnetic field generation component in accordance with, based on or in response to calculated, measured or observed values of translation force, translation displacement, and/or translation rate such that translation force, translation displacement, and/or translation rate are maintained within desired ranges to achieve an intended treatment outcome.

In one implementation, translation force may comprise a force that is applied to provide appropriate treatment of a target condition (e.g., orthopedic clinical conditions and/or craniofacial clinical conditions, which may utilize distraction osteogenesis). As an example, a first target range of translation force may be desirable when treating early onset scoliosis in juvenile patients (e.g., sufficient force to elongate the spine); and a second target range of translation force may be desirable when treating craniosynostosis in an infant patient (e.g., sufficient force to accommodate cranial growth patterns). Further, the range of translation force utilized for a target treatment may comprise necessary force adjustments resulting from treatment outcomes. That is, for example, a translation force needed to facilitate elongation of the spine may increase after subsequent extensions of the distraction growth rod device utilized.

In one implementation, the translation force can be a function of a screw torque (e.g., for a magnetic drive screw), which is derived from the rotational speed of the drive magnet disposed in the magnetic drive component. Further, the rotational speed of the drive magnet is directly related to the rotational speed of the desired magnetic field (e.g., generated by the magnetic field generator). As an example, as the rotational speed of the desired magnetic field increases, the rotational speed of the drive magnet will increase. In this example, as the rotational speed of the drive magnet increases, the screw torque will increase, which, in-turn, can increase the translation force (e.g., and vice versa). In one implementation, the magnetic field generation component can be configured to control (e.g., automatically, programmatically, and/or manually) the translation force, for example, such that a pre-set translation force may not be exceeded during a treatment procedure.

As one example, the magnetic field generation component may substantially, continuously (e.g., or periodically) monitor and/or measure the rotational speed of the desired magnetic field. In this example, the measured values of rotational speed, which are functionally related to translation force as set out above, may be used by the magnetic field generation component to calculate or determine the desired or appropriate translation force. In another implementation, some form of a force transducer may be used for monitoring and/or measuring the translation force (e.g., interposed between the drive mechanism 2206 and the first rod 2202 in FIGS. 22A-C). In this implementation, for example, the measured values of translation force from such a measurement device external to the magnetic field generation component may be transmitted wirelessly or via a connecting cable or other link to the magnetic field generation component, and/or may be manually entered into or otherwise input into the magnetic field generation component.

As an illustrative example, translation force may be controlled by allowing the operator to slowly increase the force level. In this example, after respective levels, distraction of the treatment area can be measured and input into an associated control system. For example, typical force levels may comprise a range from one to ten, with one comprising a low level of force, expected to have minimal effect on distraction, and ten comprising a highest level of force expected to be required for expansion at that stage. In this example, the force levels can change based on a number of times the patient has been adjusted. Further, as an example, levels between one and five can be shown as within a "safe" range (e.g., green indicator) on an output (e.g., screen, LED). In this example, levels between six and ten may be disposed in an "alert" range (e.g., yellow indicator); and levels above 10 can be indicated as a "danger" range (e.g., red indicator). In one implementation, levels above ten can be limited to a fraction above the typical maximum, for example, and can require additional input by the operator to ensure they are aware of the potentially dangerous translation force levels.

In one implementation, translation displacement may comprise a distance a device's first member (e.g., 304a, 1702, 2106, 2202, 2310, 2406, 2510, 2604) is translated from one of: the device's second member (e.g., 304b, 2110, 2210, 2340, 2410, 2512, 2506), or the device's member holder (e.g., 308, 1704, 2104, 2204, 2302, 2402, 2540, 2602). That is, for example, the translation displacement may comprise a distance between two attachment locations of the treatment device, from the first bone to the second bone (e.g., comprising a distraction or retraction distance).

In one implementation, a typical translation distance range may comprise two to ten millimeters for an early onset scoliosis treatment (e.g., at a three month adjustment interval). In one implementation, translation displacement is a function of translation force. That is, for example, as translation force increases, translation displacement increases (e.g., and vice versa). Therefore, for example, greater levels of force may lead to greater translation (e.g., distraction/retraction). In one implementation, translation distance may be monitored and/or measured using fluoroscopy (e.g., measuring a distance between rods or markers on the rods, such as using an x-ray device), and/or by using some form of a displacement transducer.

In one implementation, the magnetic field generation component can be configured to control (e.g., automatically, programmatically, and/or manually) the translation displacement, for example, such that a pre-set translation displacement may not be exceeded during a treatment procedure. As an illustrative example, translation displacement can be controlled by increasing the extension force (e.g., slowly)

and intermittently (e.g., or continuously) monitoring and/or measuring the resulting displacement. In this example, displacements for respective levels of force can be input to the control system (e.g., program controlling the device parameters). In this example, the control system may limit certain (e.g., high) levels of force, at least until displacement measurements are input.

In one implementation, the translation distance or displacement measurements may be provided by a measurement device, such as a device using fluoroscopy and/or some form of a displacement transducer, external to the magnetic field generation component. In this implementation, the resulting data can be transmitted wirelessly or via a connecting cable or other link to the magnetic field generation component, or the data may be manually entered into or otherwise input into the magnetic field generation component. Furthermore, for example, indications of force and displacement, detected by the control system, that are outside desired threshold or parameters can trigger alerts, and may prevent use of the device. As an example, a displacement reading of less than three millimeters may result in a "safe" indicator; greater than three but less than ten millimeters may result in a "warning" indicator; and values exceeding ten millimeters may result in a "danger" indication.

In one implementation, translation rate can comprise the rate (e.g., or speed) at which the target treatment area (e.g., skeletal structure) is translated (e.g., distracted or retracted). The translation rate may be a function of the translation force and a resistive force to the translation, for example, resulting from the tissue structure of the target patient. As an example, high rates of translation (e.g., higher than desired) may not be desired during a treatment procedure, as a higher rate may result in less precision in control of the translation force, and/or translation displacement. Further, for example, a faster rate of translation may not allow for tissue creep (e.g., the patient tissue structure translating at substantially a same rate as the device).

As an illustrative example, the translation rate can be controlled by allowing the operator to make small adjustments at respective treatment levels. Further, in this example, a treatment interval may be employed, which can comprise the amount of time corresponding to the associated tissue creep for the treatment. As an example, the treatment interval may be programmatically controlled by the control systems of the device, and may be incorporated into the other parameters controlled during treatment.

As an illustrative example, an operator of an exemplary device for generating a desired magnetic field may input information into the control system manually (e.g., using data input components on the device or by an input connection from a secondary computing device having input components, such as a keyboard or the like). The input data may comprise a patient identifier, a treatment procedure identifier, patient age, height and other patient related health information. Further, the operator can place the magnetic field generation device proximate to the treatment site (e.g., in proximity to the drive magnet). The system may be initially activated a first level. In this example, a translation a displacement (e.g., distance) may be computed based on translation force, screw torque, rotational speed of a drive magnet, or rotational speed of the desired magnetic field. Translation force, for example, may be measured by a measurement device, such as a force transducer, external to the device for generating the desired magnetic field and transmitted wirelessly to or via a connecting cable or other link to the magnetic field generating device or manually entered into or otherwise input into the magnetic field generating device. Alternatively, in one implementation, the translation displacement may be measured directly by a measurement device, for example, such as using a device implementing fluoroscopy and/or some form of a displacement transducer, external to the magnetic field generating device. In this example, the resulting data can be transmitted wirelessly to or via a connecting cable or other link to the magnetic field generating device, or the data can be manually entered into or otherwise input into the magnetic field generating device.

Further, as an example, the translation displacement or translation distance (e.g., and/or translation force) can be reviewed and/or recorded. If the operator desires additional displacement, the operator can proceed to a second level and repeat the procedure. The treatment may be terminated upon completion of a desired distraction, or if a pre-set safety limit is reached. The results of the treatment, and data generated during the treatment (e.g., force used, distraction distance, etc.) can be indicated in the patient's medical records (e.g., electronically, in memory, on paper, etc.).

Figure 31:
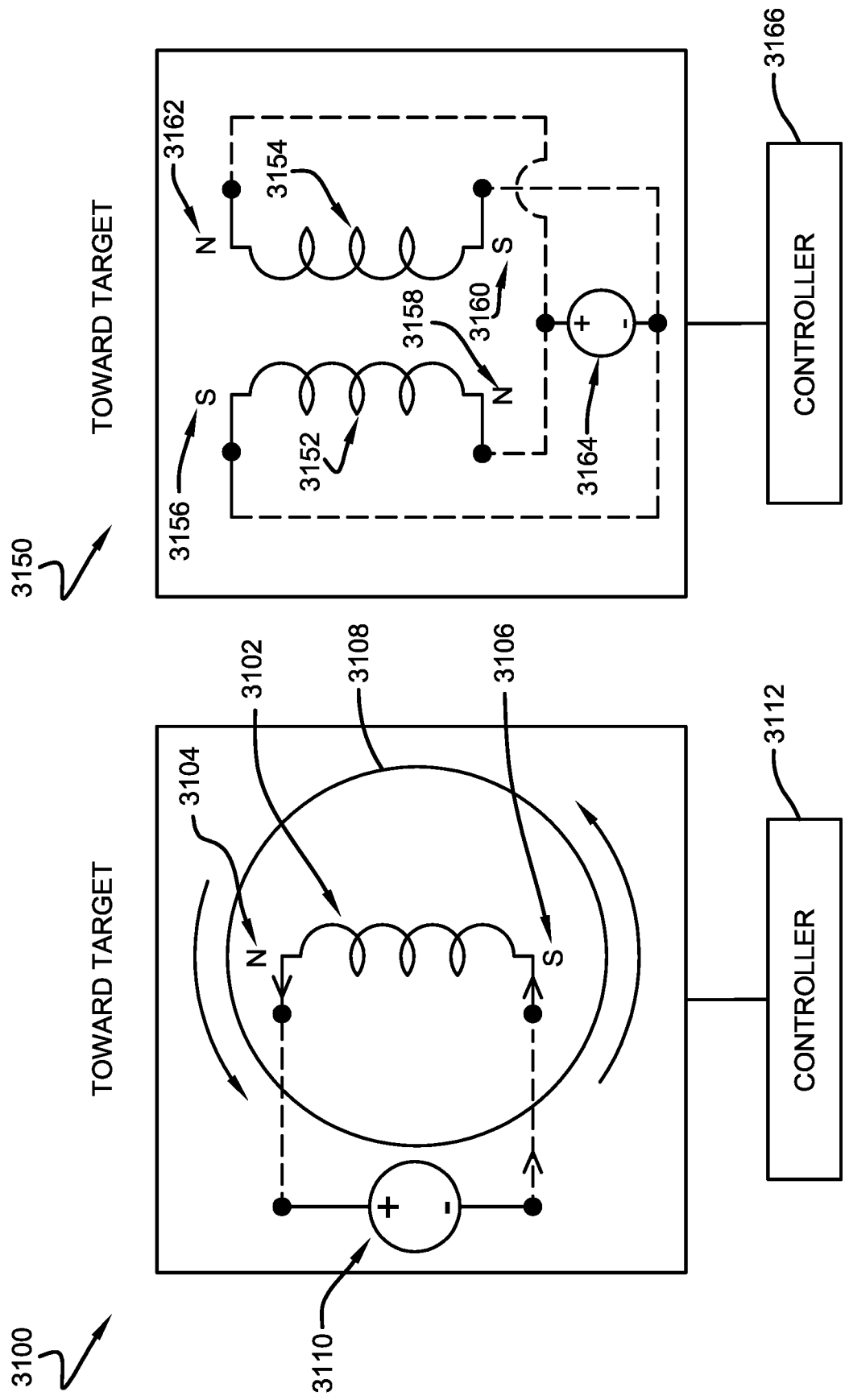
FIGS. 31A and 31B are component diagrams illustrating various views of an example implementation of one or more portions of one or more systems described herein.

FIGS. 31A and 31B are component diagrams illustrating example implementations 3100, 3150 of magnetic field generation components, which may be employed by one or more portions of one or more systems described herein. In the example implementation 3100, an electromagnet 3102 may comprise a north pole 3104 and a south pole 3106 when powered by a power source 3110. Further, in this implementation, the electromagnet 3102 may be disposed on a field rotation component 3108, whose rate of rotation may be controlled by a system controller 3112. Further, in one implementation, the controller may be configured to control (e.g., based on programmatic or manual input) the level of power provided by the power source 3110 to the electromagnet 3102. In this way, for example, the controller may be able to control an amount of magnetic force generated by the electromagnet 3102, by increasing power for more magnetic force, and decreasing power for less magnetic force.

In one implementation, the controller 3112 may control the rotation direction of the field rotation component 3108, and the rotation speed of the field rotation component 3108. In this implementation, the controller 3112 may be configured to generate the desired magnetic field for a magnetic field generation device (e.g., 1502 of FIG. 15, 2800 of FIG. 29, 2900 of FIG. 29, and 3000 of FIG. 30). In this implementation, the direction of rotation, rate of rotation, and the amount of magnetic force may be controlled by the controller 3112.

Further, the direction of rotation may affect a direction of rotation of a target drive magnet. For example, a first direction of rotation (e.g., clockwise) of the field rotation component 3108 may result in a first direction of rotation of the target drive magnet, and a second direction of rotation (e.g., counter-clockwise) of the field rotation component 3108 may result in a second direction of rotation of the target drive magnet. Additionally, as described above, the rate of rotation and the amount of magnetic force may affect an amount of translation force applied by the target magnetic drive component.

In the example implementation 3150, a magnetic field generation component can comprise a first electromagnet 3152 and a second electromagnet 3154. In this implementation 3150, the first electromagnet 3152 may comprise a south pole 3156 disposed toward a target area, as well as a north pole 3158. Further, the second electromagnet 3154 may comprise a north pole 3162 disposed toward a target area, as well as a south pole 3160. The respective electromagnets 3152, 3154 may be powered by a power source 3164. Further, the amount of power provided to the electromagnets 3152, 3154 can be controlled by a controller 3166 (e.g., programmatically). For example, the controller 3166 may limit power to the first electromagnet 3152 and provide suitable power to the second electromagnet 3154, thereby creating a north pole field at the target area. In this example, the controller 3166 may limit power to the second electromagnet 3154 and provide suitable power to the first electromagnet 3152, thereby creating a south pole field at the target area. In this way, for example, an alternating (e.g., pulsed) north and south pole magnetic field may be generated at the target area. In this example, the alternating north and south pole magnetic field may result in a desired rotational magnetic field, which can be used to rotate a target drive magnet.

In another aspect, one or more portions of the devices and systems, described herein, may be used to treat skeletal and/or musculoskeletal disorders, for example, where device distraction and/or retraction may be implemented. In one implementation, as described above, one or more portions of the devices and systems, described herein, may be used to treat scoliosis in patients, for example, where a device can be used to provide spinal distraction during scoliosis treatment. In another implementation, one or more portions of the devices and systems, described herein, may be used in distraction osteogenesis, such as to treat bone growth disorders, injuries, trauma, disease, other disorders where distraction (e.g., or retraction) may be incorporated into the treatment. For example, the one or more portions of the devices and systems, described herein, may be used in orthopedic clinical applications for treating: short stature; asymmetric limbs; cubitus varus; post-traumatic defects; and/or hand surgery. As another example, one or more portions of the devices and systems, described herein, may be used in craniofacial clinical applications for treating: craniosynostosis; cleft palate; Treacher-Collins syndrome; hemifacial microsomia; Pierre-Robin syndrome; Larsen syndrome; Freeman-Sheldon syndrome; cranial bone defects; facial bone defects; obstructive sleep apnea; and/or arrhinia.

In this aspect, in one implementation, components of the exemplary systems and devices, described herein, can be configured as rods and rod holders, for example, for treatment of scoliosis, and the component may be configured as plates and plate holders, or other structures for treatment of other disorders, injuries, trauma, or disease. For example, two bone plates may be positioned and then coupled together (e.g., in partially overlapping relationship) by one or more magnet-based screws, such as described above (e.g., 302 of FIG. 3 and 1706 of FIGS. 17-20). As another example, the one or more members, engaged with a member holder, may be configured for use in a particular treatment, such that the member can affectively engage with a bone (e.g., be shaped and sized to appropriately engage with the bone) to produce an effective treatment.

Figure 32:
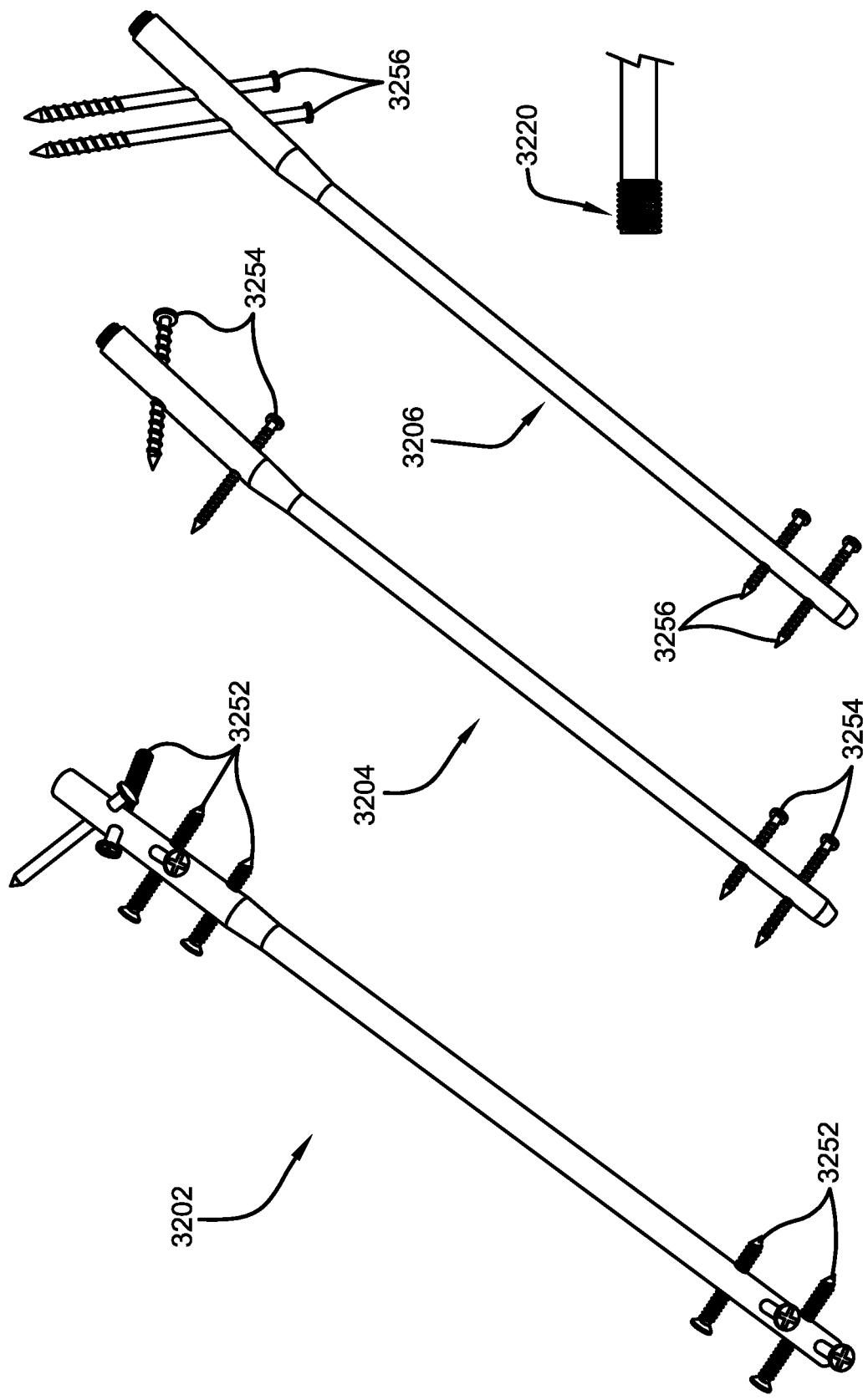
FIG. 32 is a component diagram illustrating example embodiments of a distraction osteogenesis system or device.

As illustrated in FIG. 32, an intramedullary rod or nail 3202, 3204, 3206 is a device that can be inserted into the medullary cavity of a bone, such as a long bone. Typically, these devices are used to stabilize a bone that has undergone some sort of trauma, such as a fracture, during the healing process. Intramedullary rods can come in a variety of designs configured to be complementary to the target bone. That is, an intramedullary rod may comprise a variety of diameters (widths) (e.g., seven to eleven millimeters, in half millimeter increments), and a variety of lengths (e.g., 18 to 26 millimeters in 2 millimeter increments), and can be configured to fit the target bone (e.g., immature or mature bones of varying sized patients). An intramedullary rod can also comprise a tool attachment portion 3210, 3212 that may allow an insertion/removal tool 3220 to be attached to the rod 3204, 3206. As an example, the tool may be selectably coupled to the rod and used during insertion and removal/adjustment of the rod to/from the target bone.

Additionally, fasteners 3252, 3254, 3256 (e.g., locking fasteners, such as screws) can be used to selectably, fixedly secure the rod in place in the bone, at a desired location for treatment. That is, for example, after insertion of the rod into the cavity of the bone, and appropriate placement, one or more locking screws (e.g., or other types of fasteners such as nails, bolts and nuts, etc.) may be inserted through complementary holes at each end, and the screws can be fastened to the bone at the respective locations. In this way, for example, the rod may remain at the desired location during treatment, and rotation or displacement of the rod can be mitigated.

One or more systems and/or devices may be devised for use by a clinician in a distraction osteogenesis procedure. For example, such a device or system may be utilized in long bones, such as the femur, tibia, and humerus, along with others. In one aspect, a rod-like or elongated structure can be configured for installation in the medullary cavity of a long bone. In one implementation, in this aspect, the elongated structure can comprise a distraction system that allows the elongated structure to be extended while installed in the bone. The distraction system in the elongated structure can be operated using an external signaling device, for example, using an external magnetic field that results in rotation of an internal magnetized drive mechanism (e.g., magnetically driven motor). In this way, as an example, an osteotomy can be performed at a desired location, and the distraction device or system can distract the separate parts of the target bone an appropriate distance, at an appropriate rate. In this example, new bone can form at the gap created by the distraction, ultimately forming a union at the gap between the two parts of the target bone, and a longer bone.

Figure 33:
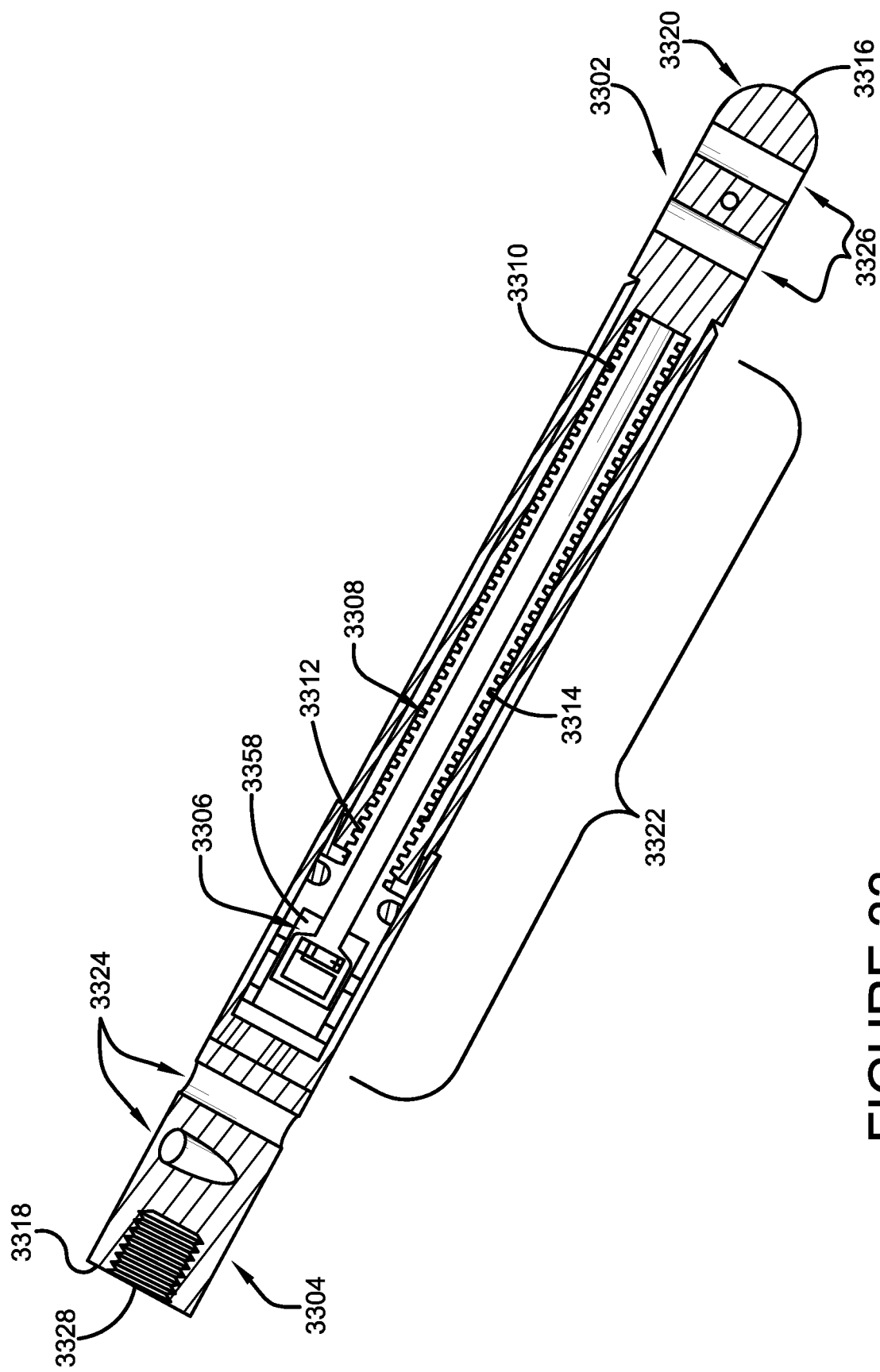
FIG. 33 is a component diagram illustrating an example implementation of one or more portions of one or more components of a bone lengthening distraction device.

FIGS. 33-36 illustrate several embodiments of a distraction osteogenesis device 3300, 3400, 3600 that may be used for a limb lengthening procedure, for example. In one implementation, as illustrated in FIG. 33, a distraction device 3300 can comprise a first portion 3304 and a second portion 3302. In this implementation, the first portion can comprise a tail portion that is configured to receive an insertion/removal tool (e.g., 3220 of FIG. 32) to facilitate inserting and/or removing the example device 3300 from a target bone. Further the second portion 3302 can comprise an insertion portion that is configured to be inserted into the medullary cavity of a bone. Further, between the first portion 3304 and second portion 3302, the elongated (e.g., rod-like) structure can comprise a distraction portion 3322 that is configured to expand and/or contract the overall length of the device 3300. For example, an external magnetic field can be applied to the device 3300 (e.g., from outside a limb comprising the target bone), resulting in a magnetic motor component 3306 rotating and driving a drive component 3308, comprising a threaded portion 3314 (e.g., external threads). In this example, the rotation of the threaded portion 3314 can result in linear translation (e.g., extension or retraction) of a complementary drive engagement component 3312 comprising internal threads. Additionally, for example, when the magnetic motor component 3306 is rotated in a first direction the distraction portion 3322 can extend; and when the magnetic motor component 3306 is rotated in a second (e.g., opposite) direction the distraction portion 3322 can retract.

Additionally, in this implementation, the example device 3300 can comprise a nose 3316 disposed at a leading end of the insertion portion 3302. The nose 3316 can be shaped to facilitate insertion of the device 3300 into a cavity of a target bone. For example, the nose 3316 can comprise a rounded, conical, tapered, or other shape that helps insert the device 330 through a hole in the bone, and into a medullary cavity for placement. In this implementation, the example device 330 can comprise a tool receiver component 3328 at a tail end 3318 of the tail portion 3304 that is configured to receive a tool. For example, the tool can be fixedly coupled with the tool receiver component 3328 and used to help insert and/or remove the device 3300 from the target bone.

In this example implementation, the device 300 can comprise an internal cavity 3310 disposed in the insertion portion 3302. As an example, the internal cavity 3310 may be sixed to receive the threaded portion 3314 of the drive component 3308, as illustrated. The example device 3300 may also comprise a internal chamber 3358 deposed in the tail portion 3304. The internal chamber 3358 can be configured to house the magnet motor component 3306, and at least a portion of the drive component 3308. Further, the internal chamber 3358 can be configured to mitigate linear translation of the drive component 3308, and/or the magnet motor component 3306, while allowing for rotation of the magnet motor component 3306 in the internal chamber 3358. In this way, for example, the magnet motor component 3306 and drive component 3308 may freely rotate, allowing the insertion portion 3302 to linearly translate.

Additionally, the first portion 3304 and second portion 3302 may comprise one or more vias, openings, or fastener receivers 3324, 3326. The respective fastener receivers 3324, 3326 can be configured to receive a bone fastening component (e.g., locking screw, bolt and nuts et, nail, etc.). In one implementation, the fastener receivers 3324, 3326 may be spaced apart, and may also be disposed at various axes to a central axis of the device 3300. For example, respective fastener receivers 3324, 3326 may account for an X, Y and/or Z axis for the device 3300. In this way, for example, a clinician may have more options for fastening the device to target bone, depending on clinical circumstances.

Figure 34:
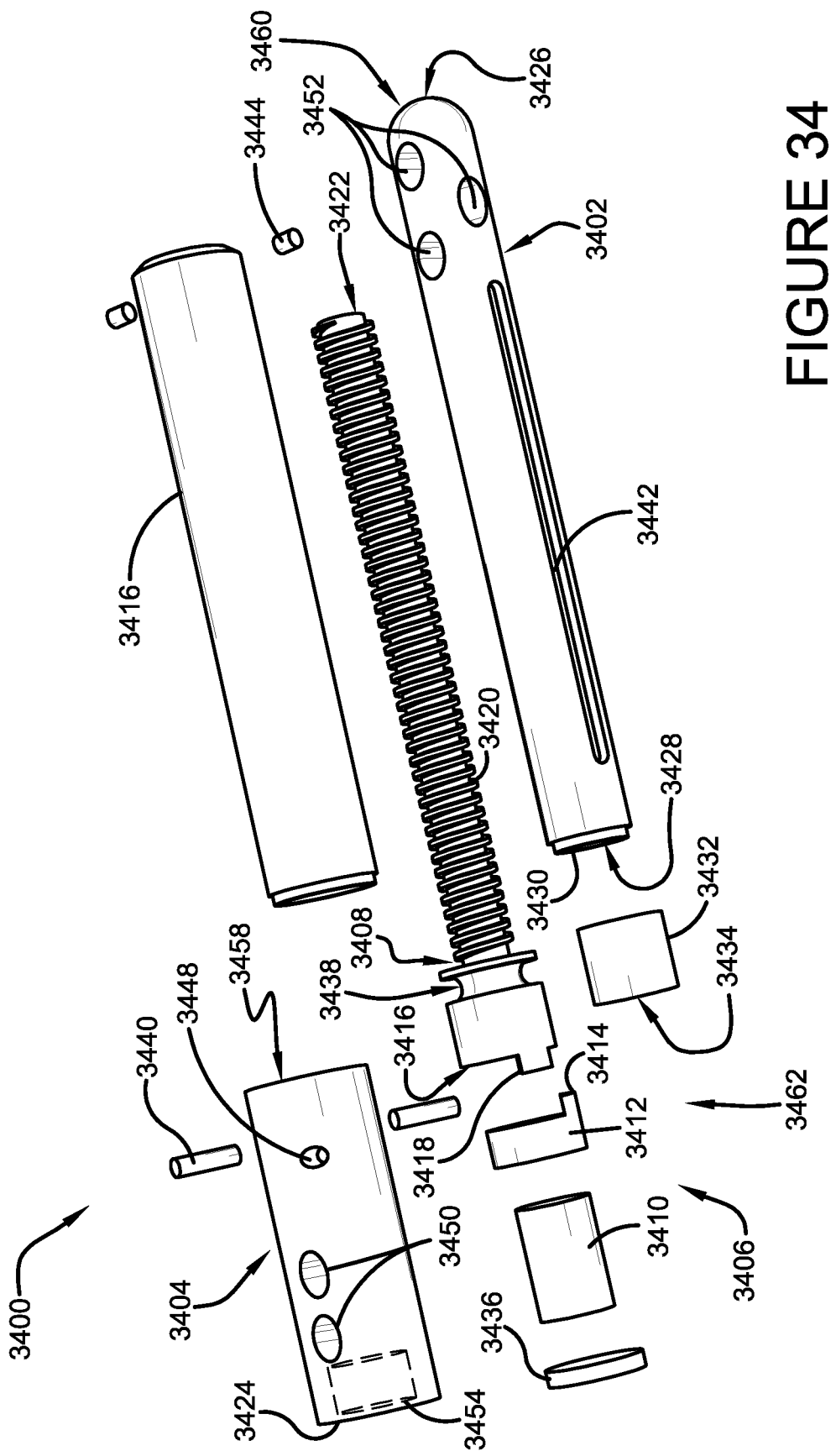
FIG. 34 is a component diagram illustrating an example implementation of one or more portions of one or more components of one or more systems described herein.
Figure 35:
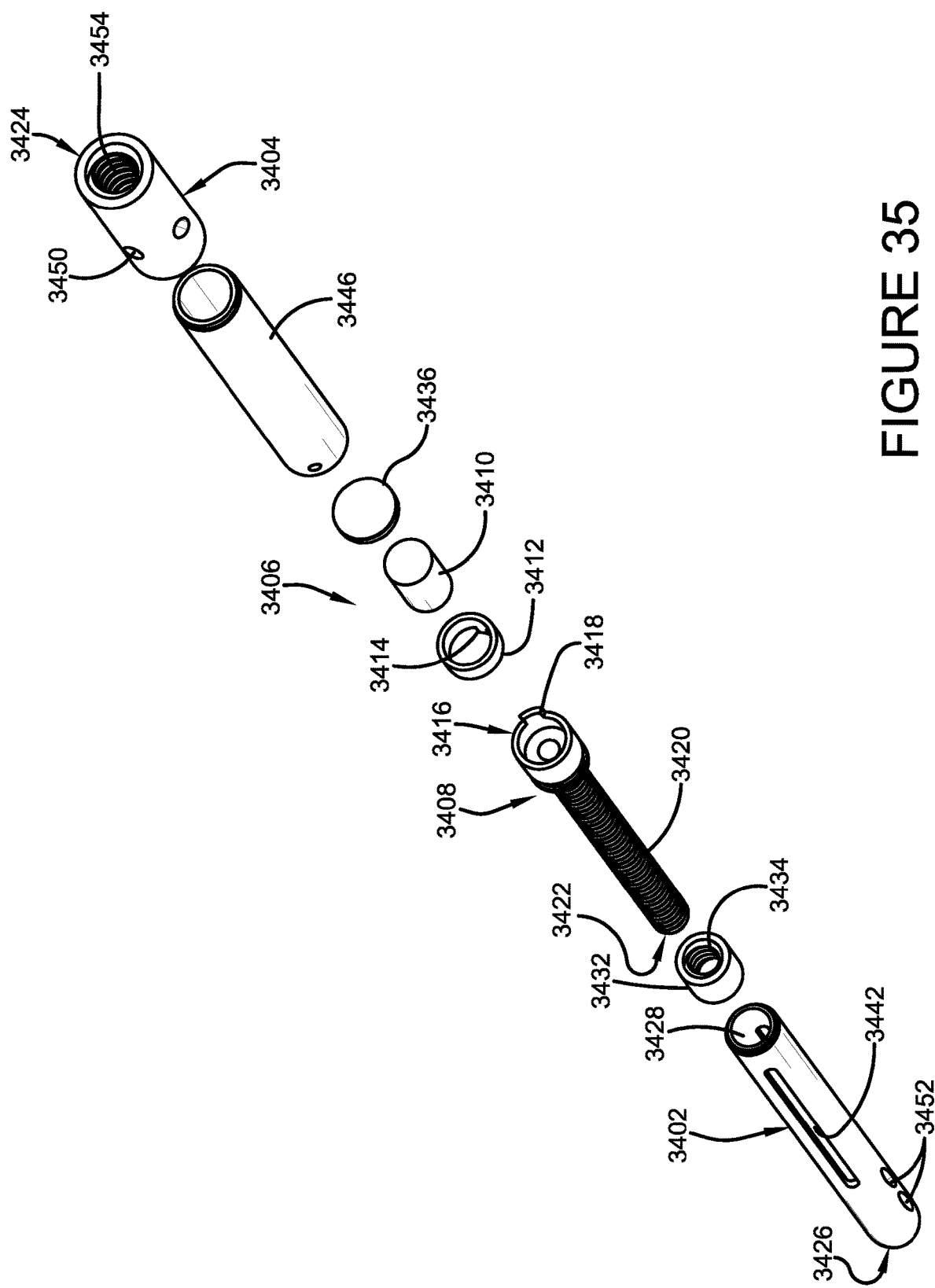
FIG. 35 is a component diagram illustrating an example implementation of one or more portions of one or more components of one or more systems described herein.

FIGS. 34 and 35 illustrate another embodiment of an example device 3400, or portion of a system, that may be used for distraction osteogenesis. This example embodiment 3400 can comprise a tail or first portion (piece) 3404 and an insertion or second portion (piece) 3402. The second portion 3402 can be elongated and configured as the insertion end of a distraction osteogenesis device (e.g., like an intramedullary rod or nail), for example, formed to be insertable through an opening in a target bones exterior into the medullary cavity of the target bone. In this implementation, the second/insertion portion 3402 can comprise a nose 3426 disposed at its leading end 3460. The nose 3426 can be shaped to facilitate insertion into a cavity of a target bone through an opening in the target bone. The second/insertion portion 3402 can comprise an internal cavity 3428 with an opening 3430 at an opposite end of the second/insertion portion 3402 from the leading end 3460. The internal cavity 3428 can be configured to receive a second end 3422 of a drive component 3408. That is, for example, the internal cavity 3428 can be sized and shaped to, at least partially, enclose the second end 3422 of a drive component 3408.

The tail or first portion (piece) 3404 can be elongate, and comprise an internal chamber 3458 that houses at least a portion of a distraction drive 3462. The internal chamber 3458 can be configured to facilitate rotation of the distraction drive 3462, and also mitigate linear translation of the distraction drive 3462. That is, for example, the internal chamber may allow the distraction drive 3462 to freely rotate around a linear axis, but may prevent the distraction drive from moving linearly along that linear axis.

Further, in the example embodiment 3440, the distraction drive 3462 can comprise a magnet 3410 that rotates (e.g., in the internal chamber 3458) under application of a magnetic field. That is, for example, an externally applied magnetic field results in the magnet 3410 rotating around a linear axis of the device, in the internal chamber 3458. The distraction drive 3462 can also comprise a rotational force applicator 3414 that is fixedly engaged with the magnet, and rotates with the magnet 3410. In one implementation, the distraction drive 3462 can comprise a collar 3412 that is fixedly engaged with the magnet 3410, and comprises a first protrusion 3414 that acts as the rotational force applicator 3414. That is, for example, the rotational force applicator 3414 (e.g., first protrusion) can be used to apply the rotational force generated by the rotation of the magnet under a magnetic field. In one implementation, the combination of the magnet 3410, collar 3412, and first protrusion 3414 may comprise a magnetic motor component 3406.

In this example embodiment 3400, the distraction drive 3462 can comprise the drive component 3408. The drive component 3408 can comprise a rotational force receiver 3418 fixedly disposed at a first end 3416 of the drive component 3408. The rotational force receiver 3418 can be disposed in direct contact with the rotational force applicator 3414. In one implementation, the rotational force receiver 3418 can comprise a second protrusion that is configured to receive the rotational force provided by the first protrusion 3414, as provided by the rotation of the magnet 3410 under a magnetic field.

In one implementation, the first protrusion 3414 applies a direct impact force of a magnitude relative to the distance between the axis of rotation and the first protrusion 3414. This amount of force generated by the magnetic motor 3406 may not, at least initially, be enough to overcome the static force of the drive component 3408 at rest. In this example, the first protrusion 3414 may comprise a tooth-like hammer that bounces backward (and the magnet may rotate backward) from the tooth-like anvil of the second protrusion 3418 upon impact. In this implementation, the direct impact force may be reapplied to the second protrusion 3418. In this example, this bounce-back hammering effect may be used to overcome the static force of the drive component 3408 at rest, and apply additional torque to the drive component 3408 than merely directly driving the drive component 3408 from the magnetic motor 3406. In this way, for example, additional gearing, transmissions and clutch assemblies may not be needed to appropriately rotate the drive component 3408.

In the example embodiment of FIGS. 34 and 35, the drive component 3408 of the distraction drive 3462 can comprise a linear force applicator 3420 at a second end 3422. The linear force applicator 3420 can comprise external threads that rotate upon application of a rotational force from the rotational force applicator 3414 to the rotational force receiver 3418. That is, for example, the rotation of the magnet 3410 under a magnetic force provides the rotational force application to the first end 3416 of the drive component 3408, which, in turn, rotates the external threads of the linear force applicator 3420 at a second end 3422.

Further, the example device 3400 comprises a drive engagement component 3432 that is disposed proximate the opening 3430 to the internal cavity 3428 of the insertion portion 3402. The drive engagement component 3432 can comprise internal threads 3434 that are complementary to, and in threaded engagement with, the external threads of the linear force applicator 3420. This engagement can be used to convert the rotation of the external threads of the linear force applicator 3420 to a linear translation of the insertion portion 3402. That is, for example, the rotation of the external threads will cause the drive engagement component 3432 to translate linearly along the second end of the drive component 3422. The drive engagement component 3432 can be coupled with (e.g., fixedly or selectably) the insertion portion 3402 resulting in the insertion portion 3402 translating linearly when the drive engagement component 3432 is translated.

In one implementation, the tail portion 3404 can comprise a spacer 3436 that is disposed between a tail end 3424 of the internal chamber 3458 and the magnet 3410. In this implementation, the spacer 3436 can provide for improved rotation of the magnet. For example, the spacer 3436 can be made of a material that reduces friction, such as a type of polymer, graphite, or other similar material. Further, the example embodiment may comprise an outer sleeve 3446 that is operably disposed in telescopic engagement with the outside of the insertion portion 3402. That is, for example, the outer sleeve 3446 may house the insertion portion 3402 when the example device 3400 is disposed in a retracted position (e.g., FIG. 33). In this example, as the insertion portion 3402 is distracted from the tail portion 3404, the outer sleeve 3446 can remain in-place, engaged with the tail portion 3404, allowing the insertion portion 3402 to telescope out of the outer sleeve 3446 when distracted.

In one implementation, the example device 3400 can comprise a groove 3442 and a rotation stop 3444 disposed in the groove. The groove can be disposed linearly along the insertion portion 3402, and the rotation stop can be engaged with the outer sleeve 3446 to mitigate rotation of the insertion portion 3402 in the bone cavity. For example, the outer sleeve 3446 can be fixedly engaged (e.g., or selectably fixedly engaged) with the tail portion, and the rotation stop 3444 can couple the outer sleeve 3446 with the groove 3442 in the insertion portion 3402. In this example, this relationship may merely allow the insertion portion to translate linearly, and not rotate with the rotation of the drive component 3408.

In one implementation, the insertion portion 3402 can comprise one or more fastener receivers 3452 that are disposed proximate the leading end 3460. The respectively one or more fastener receivers 3452 can be configured for receiving a fastener to fasten the insertion portion to a first part of the target bone. Further, the tail portion 3404 can comprise one or more fastener receivers 3450 that are disposed proximate the tail end 3424, for respectively receiving a fastener to fasten the tail portion 3404 to a second part of the target bone. In one implementation, the tail portion 3404 can comprise a tool engagement component 3454 that fixedly engages with a tool (e.g., 3220 of FIG. 32) to facilitate insertion and extraction of the device 3400 from the target bone.

In one implementation, in example device 3400, the tail portion 3404 can comprise a tail pin 3440 that is selectably engagable with the tail portion 3404. Further, the tail pin 3440 is selectably engagable with a drive collar 3438 that is disposed proximate the first end 3416 of the drive component 3408. The arrangement of the tail pin 3440 secured through the tail portion 3404 and engaging the drive collar 3438 can mitigate the linear translation of the drive component 3408 in the tail portion 3404. That is, for example, with the tail portion 3404 remaining stationary during distraction, the distraction drive components can freely rotate in the tail portion 3404, while the tail pin 3440 holds the drive component 3408 in place, linearly.

Figure 38:
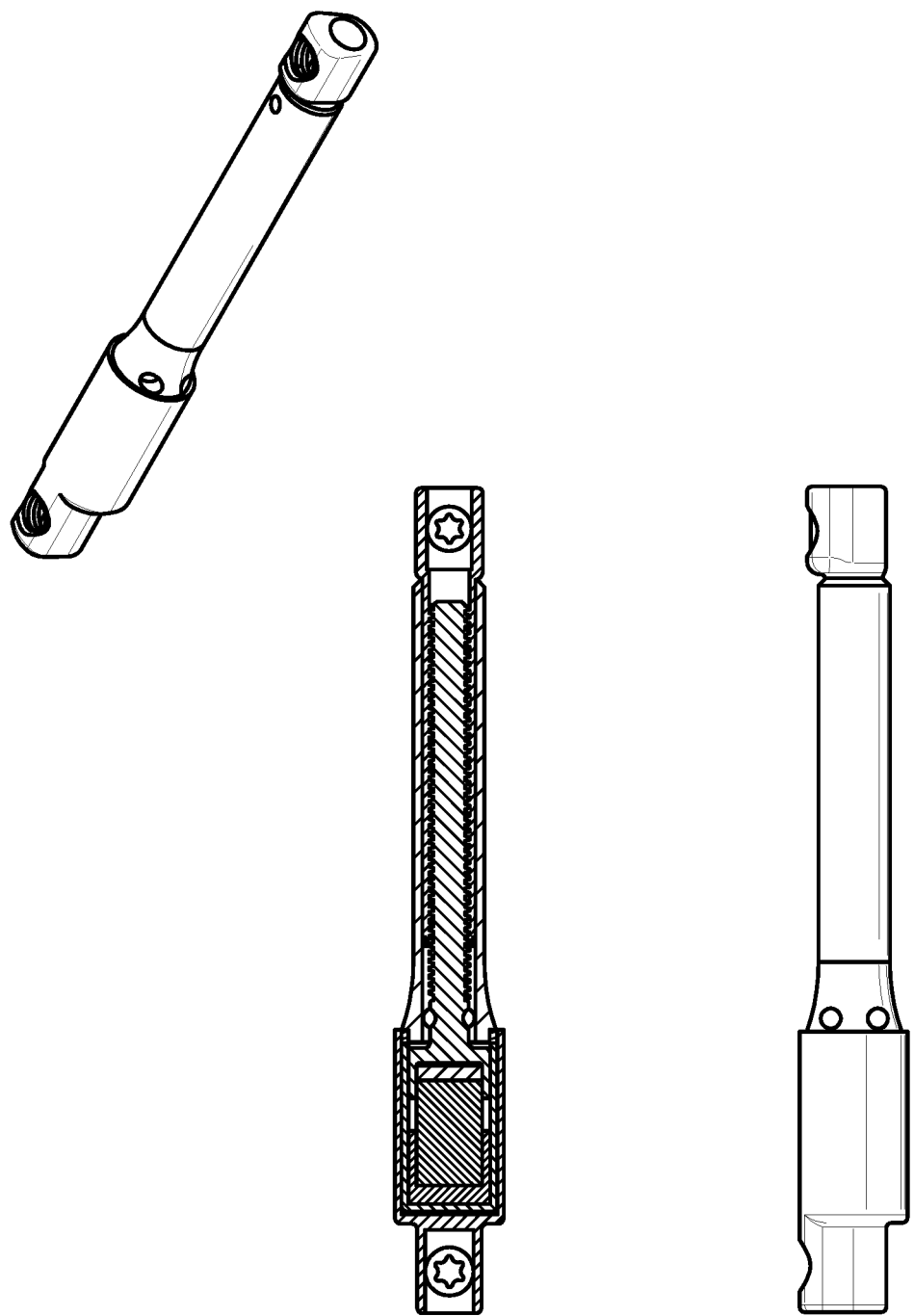
Figure 39:
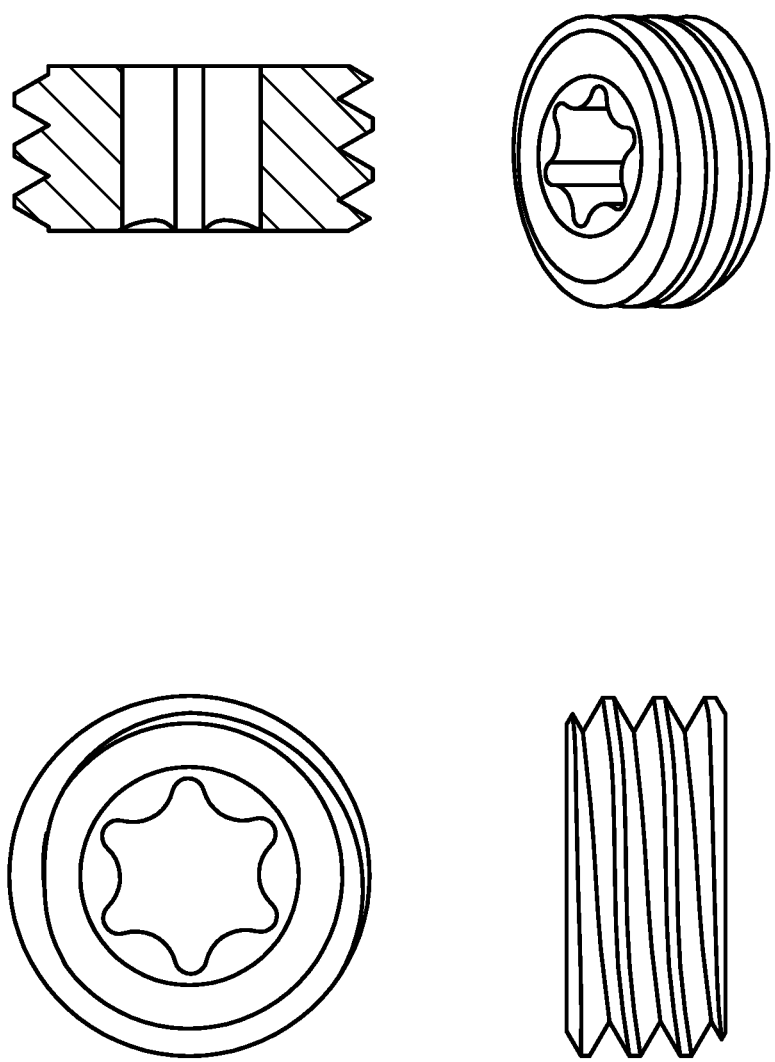
Figure 41:
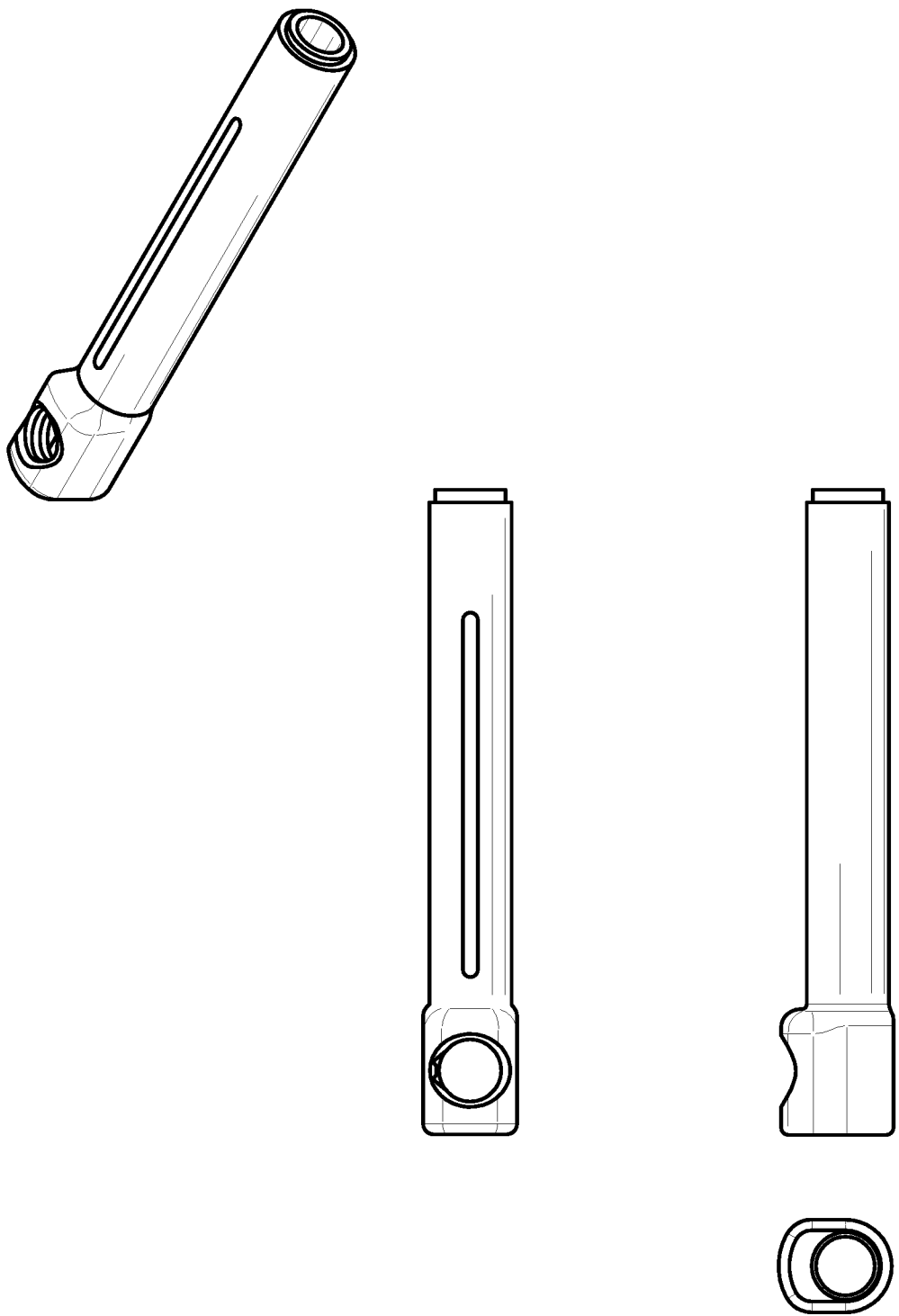
Figure 43:
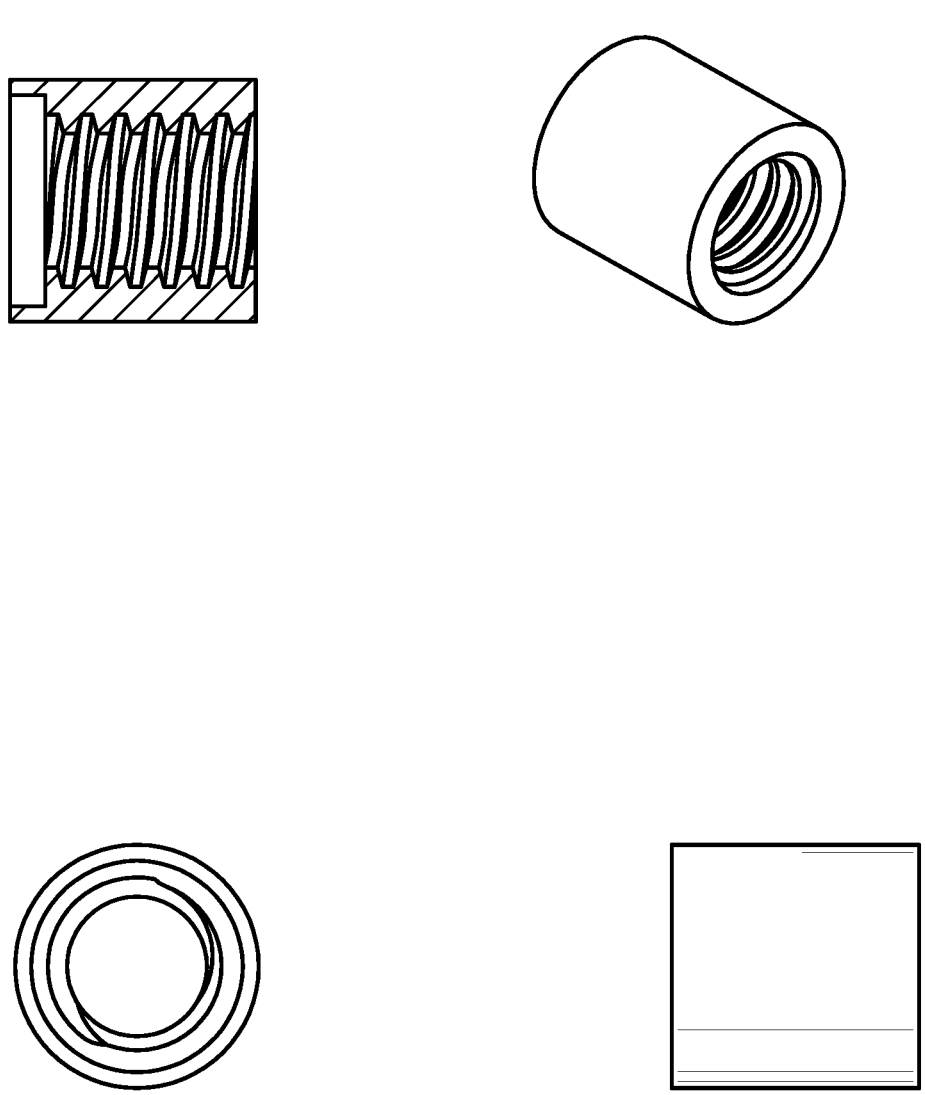
Figure 45:
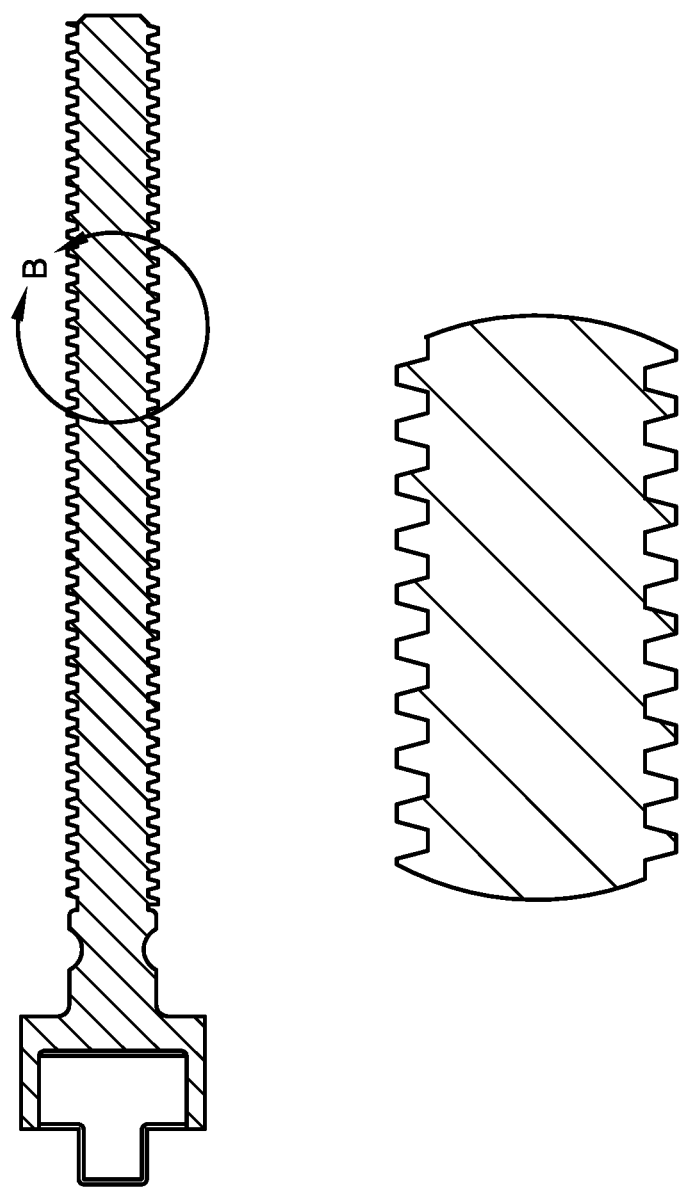
Figure 48:
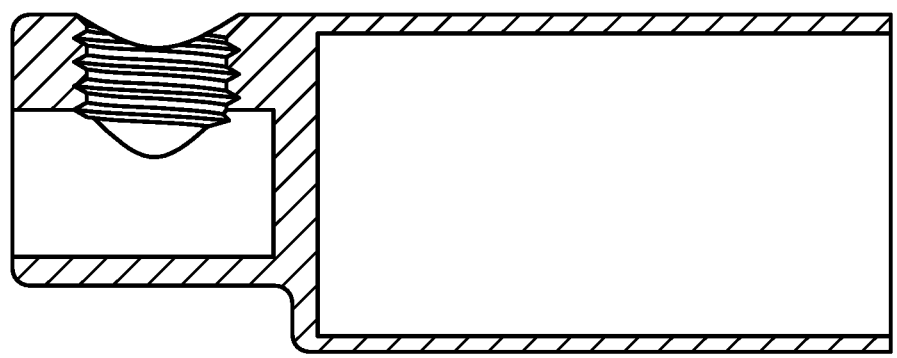
Figure 49:
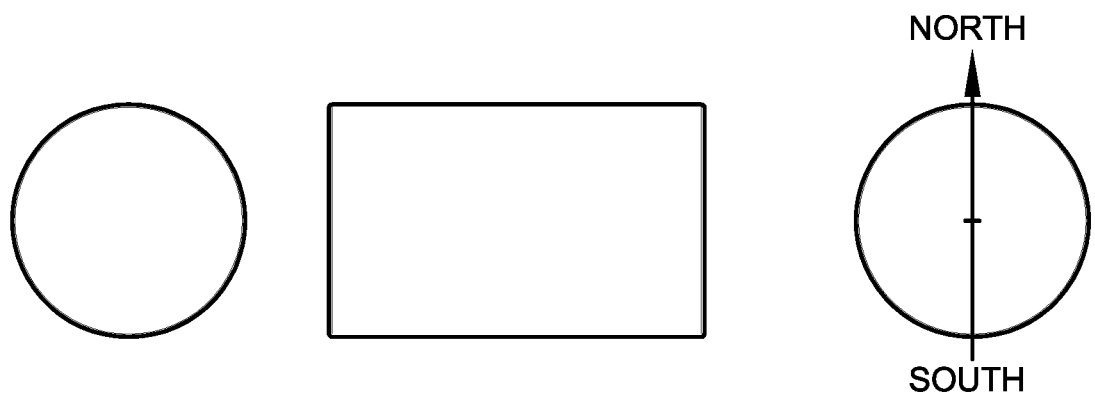
Figure 50:
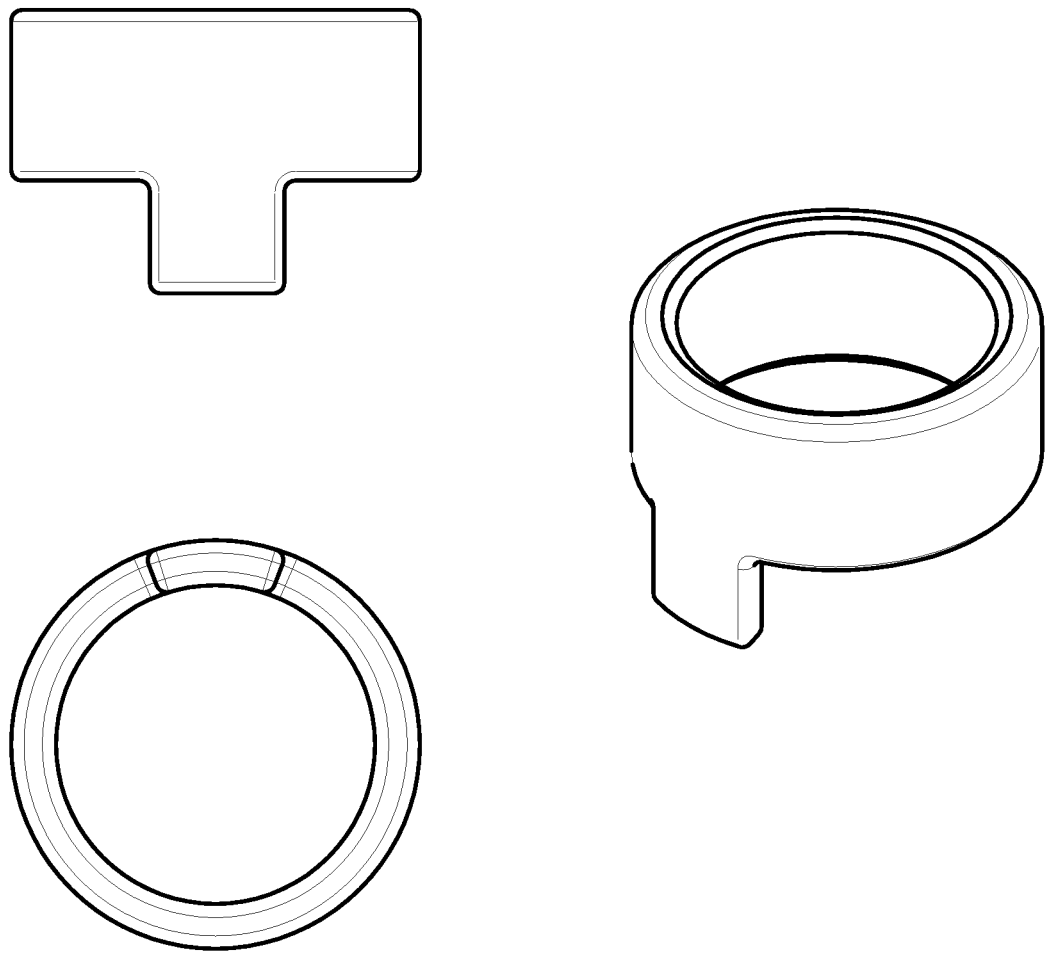
Figure 51:
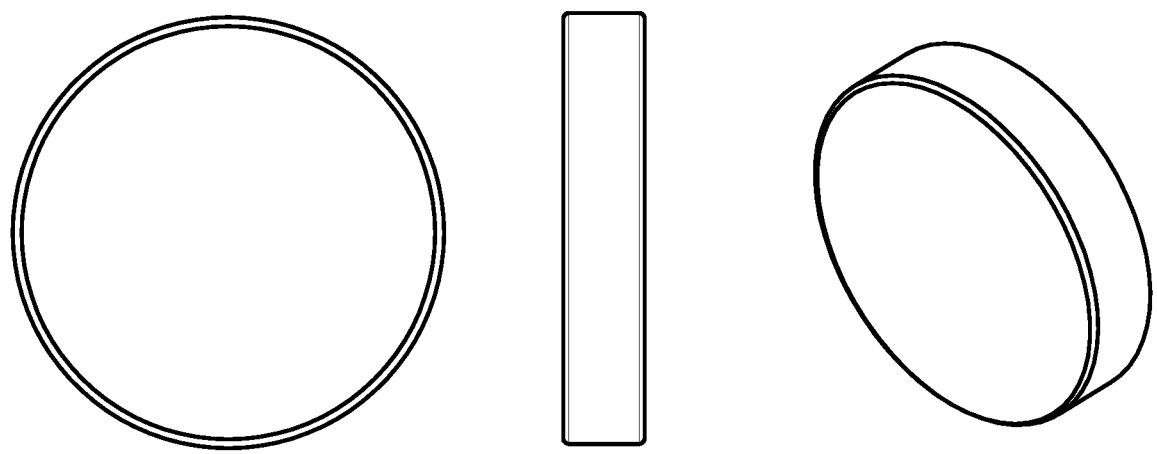
Figure 52:
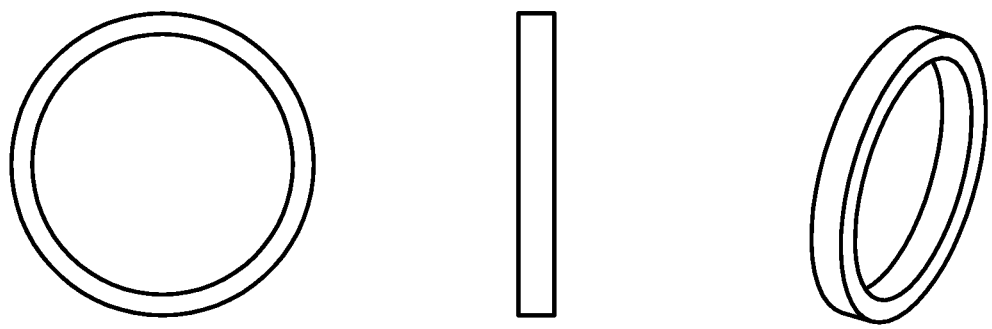
Figure 53:
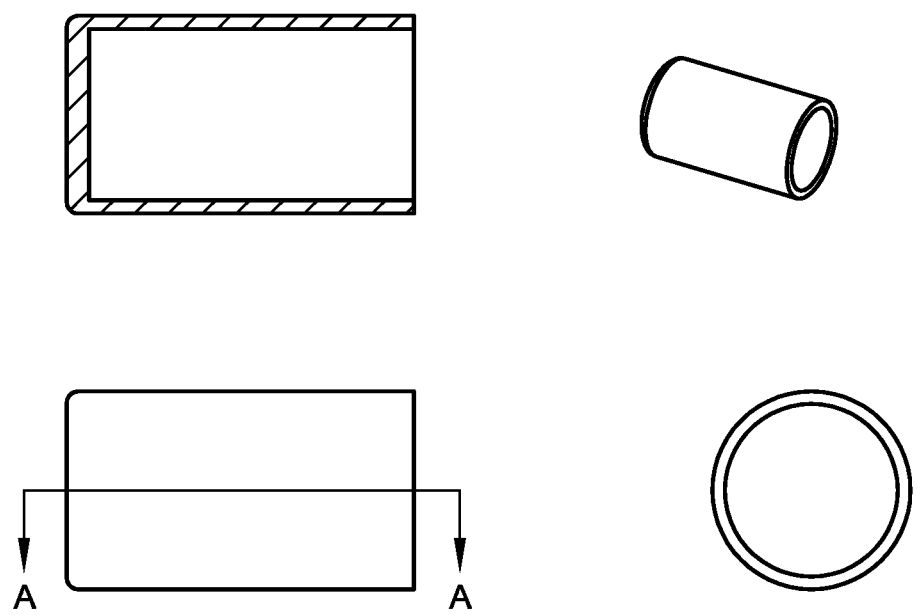

In one implementation, the engagement between the first end 3416 and the magnetic motor component 3406 may be enclosed in a sealed chamber. For example, as illustrated in FIGS. 38 and 53, an enclosure may be configured to house the magnetic motor component 3406 to mitigate fluid entry (e.g., bodily fluid) from entry into the magnetic motor component 3406 area.

Figure 36:
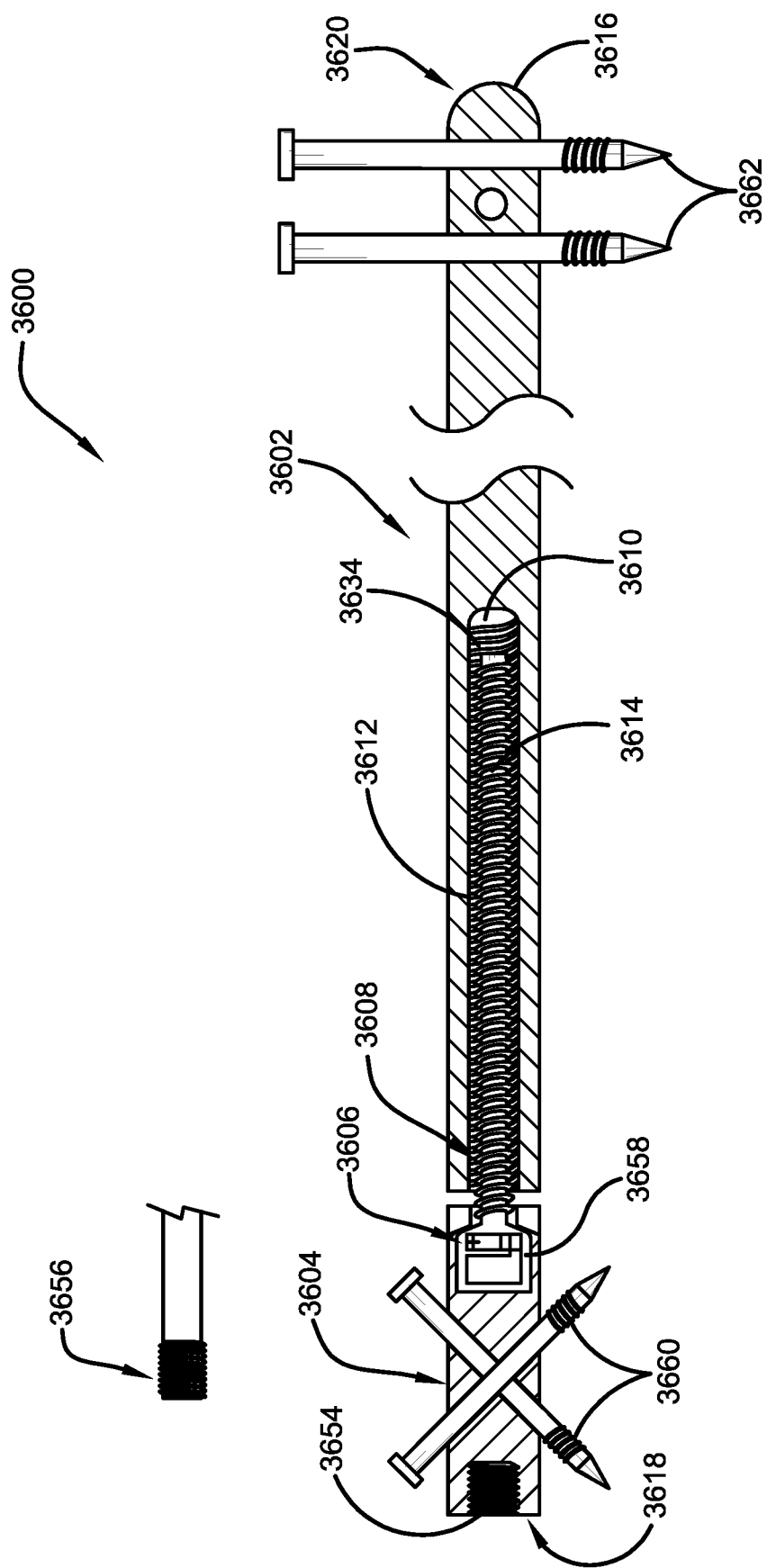
FIG. 36 is a component diagram illustrating an example implementation of one or more portions of one or more components of one or more systems described herein.
Figure 37:
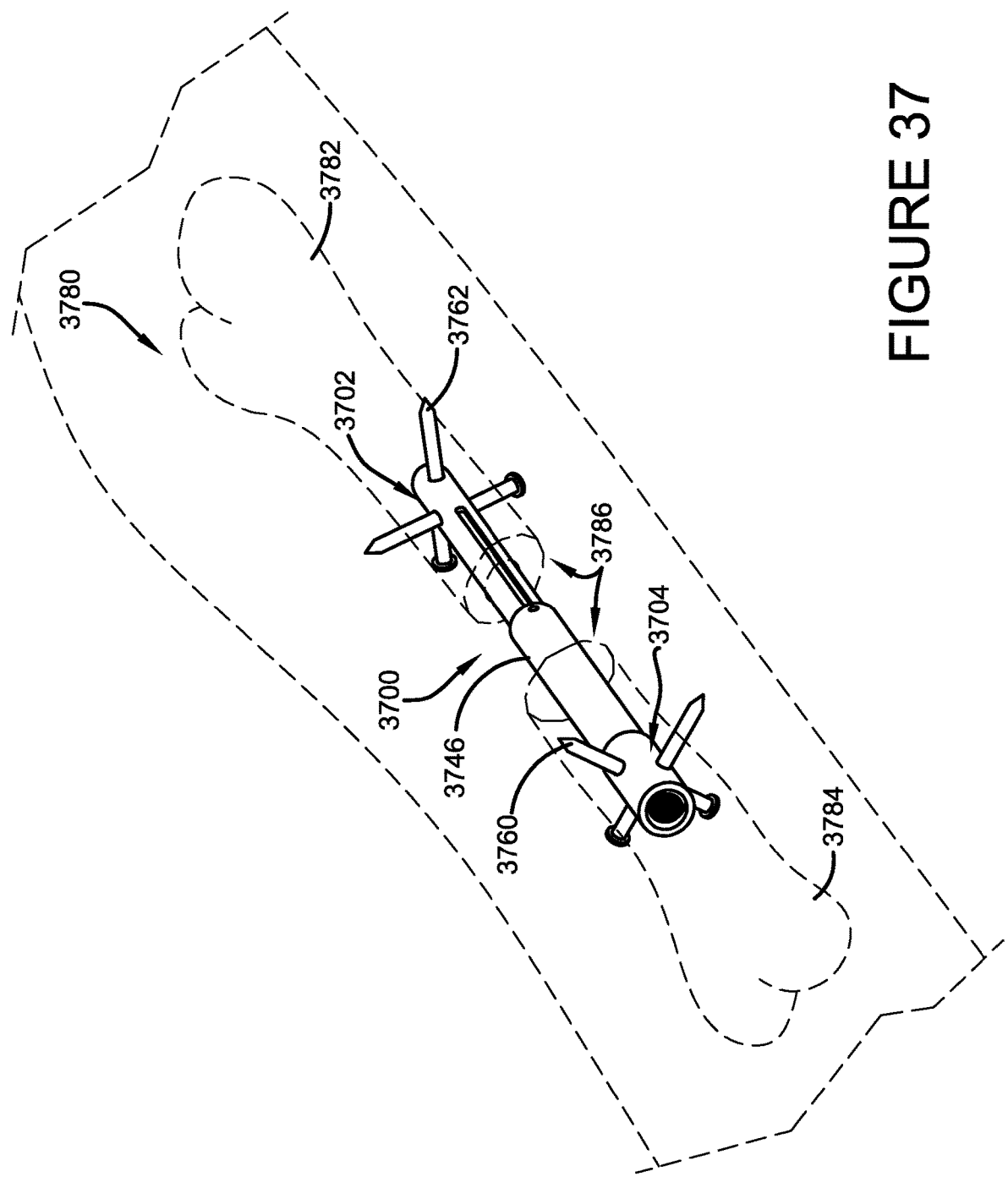
FIG. 37 is an illustration of an example environment where one or more portions of one or more systems described herein may be implemented.

FIGS. 36 and 37 illustrate an implantation of a distraction osteogenesis device 3600, which can be employed as part of a system, to perform distraction osteogenesis. In this implementation, the device 3600 can comprise a tail or first portion 3604, and a second or insertion portion 3602. A magnetic motor 3606 is disposed in the internal chamber 3658 of the tail portion 3604 to provide rotation when subjected to an external magnetic field, such as provided by a magnetic field generation component (e.g., as provided in FIGS. 16, and 28-31). The Magnetic motor 3606 can be engaged with a drive component 3608 that is, at least partially disposed in an internal cavity 3610 of the insertion portion 3602.

A drive engagement component 3612 can be threadedly coupled with the drive component 3608, by coupling the external thread 3614 of the drive component 3608 with internal threads 3634 of the drive engagement component 3612. This threaded coupling can result in linear translation of the drive engagement component, and a the coupled insertion component 3602, when the drive component 3608 is rotated by the magnetic motor 3606.

In one implementation, the insertion portion 3602 can comprise a shaped nose 3616 at a leading end 3620. The nose 3616 can be shaped to facilitate insertion of the device 3600 into the target bone, as illustrated in FIG. 37. In one implementation, the tail portion 3604 comprises a tool engagement component 3654 at the tail end 3618 that can fixedly, selectably engage with a tool 3656. The tool 3656 can be used to facilitate insertion and removal of the device 3600 from the target bone.

In one implementation, as illustrated, upon insertion in the target bone, one or more tail fasteners 3660, 3760, and one or more insertion portion fasteners 3662, 3762 can be engaged with the device 3600. In this way, for example, the device 3600 may be fixedly engaged with the target bone 3780, at a first part 3782 and a second part 3784. By fixing the device 3600 to the target bone 3780, the device 3600 may not move significantly during the distraction osteogenesis procedure.

For example the device may be used in a distraction osteogenesis procedure. As an example, during an initial (e.g., first) operation, an osteotomy (e.g., corticotomy) may be performed on the target bone, such as by cutting the bone into two segments. In this example, the distraction rod can be inserted into the medullary cavity of both portions of the bone, such as by drilling into an insertion point, and inserting the rod through the resulting hole. Further, one or more locking screws/bolts can be fastened at respective ends of the device to the bone, using the appropriate vias. In this example, the magnetic drive can be actuated, such as by an external magnetic field, resulting in distraction (e.g., extension) of the rod to the desired length (e.g., to meet the desired goals of the procedure). Additionally, the device can be left in place while the desired osteogenesis occurs between the two bone segments. Once the desired result has been achieved (e.g., and the bone is healed) a second (e.g., subsequent) operation may be performed to remove the device, such as by using the device removal tool attached to a tail end of the rod.

As illustrated in FIG. 37, the device 3700 can be inserted in the target bone 3780, such as after an osteotomy has been performed. The insertion portion 3702 may be inserted through a hole drilled in the exterior of the bane 3780, and inserted into the medullary cavity of the bone, such as using the tool 3656. Upon insertion, one or more fasteners 3760, 3762 can be engaged with the device 3700 and bone 3780 to hold the device 3700 in place. As an example, after appropriate insertion and fastening, the example device 3700 may be distracted (e.g., expanded) to create a bone separation 3786 at the osteotomy site. In this way, for example the distraction osteogenesis can take place.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A device for bone lengthening, comprising:
    a distraction drive comprising:
        a magnet rotating under application of a magnetic field around a central longitudinal axis;
        a rotational force applicator comprising a hammer that is fixedly engaged with the magnet, and rotating with the magnet; and
        a drive component comprising:
            a rotational force receiver comprising an anvil that is fixed at a first end in direct contact with the rotational force applicator; and
            a linear force applicator comprising a cylindrical body disposed at a second end comprising external threads rotating upon application of a rotational force from the rotational force applicator to the rotational force receiver;
    a tail portion comprising an elongate body disposed along the central longitudinal axis, the tail portion housing at least a portion of the distraction drive in an internal chamber that facilitates the rotation of the distraction drive and mitigates linear translation of the distraction drive with respect to the tail portion;
    an insertion portion comprising an elongate body disposed along the central longitudinal axis, the insertion portion comprising a nose disposed at a leading end, the nose shaped to facilitate insertion into a cavity of a target bone through an opening in the target bone, the insertion portion comprising an internal cavity with an opening at an opposite end from the leading end to receive the second end of the drive component, wherein the tail portion and insertion portion are spaced apart to distract apart along the central longitudinal axis; and
    a drive engagement component comprising a tube-shaped body disposed proximate the opening to the internal cavity, and directly engaged with the insertion portion between the tail portion and the insertion portion, the drive engagement component comprising internal threads complementary to, and in threaded engagement with, the external threads of the linear force applicator to convert the rotation of the external threads to linear translation of the insertion portion.

2. The device of claim 1, the rotational force applicator comprising a tooth-like hammer protruding from the magnet, and the rotational force receiver comprising a tooth-like anvil protruding from the first end of the drive component, and complementary to the hammer.

3. The device of claim 1, the tail portion comprising a spacer disposed between a tail end of the internal chamber and the magnet providing for improved rotation of the magnet.

4. The device of claim 1, one of:
    the drive engagement component fixedly engaged with the insertion portion at the end opposite from the leading end; and the drive engagement component operably, non-fixedly engaged with the insertion portion at the end opposite from the leading end.

5. The device of claim 1, comprising an outer sleeve operably disposed in telescopic engagement with the outside of the insertion portion.

6. The device of claim 5, the insertion portion comprising a groove and a rotation stop disposed in the groove, the groove disposed linearly along the insertion portion, and the rotation stop engaged with the outer sleeve to mitigate rotation of the insertion portion in the bone cavity.

7. The device of claim 1, the insertion portion comprising one or more fastener receivers proximate the leading end for respectively receiving a fastener to fasten the insertion portion to a first part of the target bone.

8. The device of claim 1, the tail portion comprising one or more fastener receivers proximate a tailing end for respectively receiving a fastener to fasten the tail portion to a second part of the target bone.

9. The device of claim 1, the tail portion comprising a tail pin selectably engaged with the tail portion and engaging with a drive collar proximate the first end of the drive component to mitigate linear translation of the drive component in the tail portion.

10. The device of claim 1, the tail portion comprising a tool engagement component that fixedly engages with a tool to facilitate insertion and extraction of the device from the target bone.

11. A method for manufacturing a bone lengthening device, comprising:
operably disposing a magnetic motor component in a cavity in a first elongated portion, the first elongated portion comprising a tail end of a bone lengthening device to fixedly secure to a second portion of a target bone, the first elongated portion comprising an elongate body disposed along a central longitudinal axis with an internal chamber operably housing the magnetic motor and mitigating linear movement of the motor with respect to the first portion while allowing for rotation of the motor in the internal chamber, the magnetic motor comprising:
a magnet rotating around the central longitudinal axis under application of a magnetic field; and
a first protrusion fixedly engaged with the magnet, and rotating with the magnet;
operably engaging a drive component with the motor, the drive component comprising an elongate cylindrical body disposed along the central longitudinal axis, and comprising: a first end and a second end, the first end comprising external screw threads, the second end comprising a second protrusion to operably engage in contact with the first protrusion when the magnet is subjected to the magnetic field resulting in rotation of the threads of the first end around the central longitudinal axis; and
operably engaging a second elongated-portion with the drive component, the second elongated portion comprising an elongate body disposed along the central longitudinal axis, and comprising a leading end of the bone lengthening device insertable into a cavity of a target bone to fixedly engage with a first part of the target bone, the second elongated portion comprising:
an insertion nose shaped to facilitate insertion into the cavity of the target bone;
an internal chamber sized to receive the first end of the drive component; and
a drive engaging component comprising a tube-shaped body in threaded engagement with the drive component, the drive engaging component comprising internal threads complementary to the external screw threads of the first end of the drive component to convert the rotation of the threads of the first end to linear translation of the drive engaging component and the second elongated portion;
wherein the first elongated portion and the second elongated portion are spaced apart to distract apart along the central longitudinal axis.

12. The method of claim 11, comprising:
forming a first fastener receiver in the second elongated portion, the first fastener receiver used to engage with a first bone fastener to secure the second elongated portion to the first part of the target bone; and
forming a second fastener receiver in the first elongated portion, the second fastener receiver used to engage with a second bone fastener to secure the first elongated portion to a second part of the target bone.

13. The method of claim 11, comprising operably disposing a spacer disposed between the tail end of the cavity of the first elongated portion and the magnet providing for improved rotation of the magnet.

14. The method of claim 11, comprising operably disposing an outer sleeve in telescopic engagement with the outside of the insertion portion.

15. The method of claim 14, comprising forming a groove linearly along the second elongated portion, and operably engaging a rotational stop with the groove and the outer sleeve to operably mitigate rotation of the second elongated portion.

16. The method of claim 11, comprising forming tool engagement component in the tail end of the first elongated portion that fixedly engages with a tool to facilitate insertion and extraction of the device from the target bone.

17. A system for bone lengthening, comprising:
a motor component comprising a magnet rotating under application of a magnetic field around a central longitudinal axis that is fixedly engaged with a collar comprising a first protrusion;
a drive component comprising an elongate cylindrical body disposed along the central longitudinal axis, and comprising: a first end and a second end, the first end comprising external screw threads, the second end comprising a second protrusion to operably engage in contact with the first protrusion when the magnet is subjected to the magnetic field resulting in rotation of the threads of the first end around the central longitudinal axis;
an insertion portion comprising an elongate body disposed along the central longitudinal axis, the insertion portion insertable into a cavity of a target bone to fixedly engage with a first part of the target bone, the insertion portion comprising an insertion nose shaped to facilitate insertion into the cavity of the target bone, the insertion portion comprising:
a first fastener receiver engaging with a first bone fastener to secure the insertion portion to the first part of the target bone;
a first internal chamber sized to receive the first end of the drive component; and
a drive engaging component comprising a tube-shaped body, and comprising internal threads complementary to the external screw threads of the first end of the drive component to convert the rotation of the threads of the first end to linear translation of the insertion portion;

a tail portion comprising an elongate body disposed along the central longitudinal axis, the tail portion disposed at an opposite end from the insertion portion to fixedly engage with a second part of the target bone, the tail portion comprising a second internal chamber operably housing the motor component and mitigating linear movement of the motor component with respect to the tail portion while allowing for rotation of the motor component, and a second fastener receiver engaging a second bone fastener to secure the tail portion to the second part of the target bone, wherein the tail portion and insertion portion are spaced apart to distract apart along the central longitudinal axis; and a magnetic field generation component generating the external magnetic field resulting in the linear translation of the insertion portion.

18. The system of claim 17, comprising a tool to facilitate driving the insertion portion into, or removal from, the cavity of the target bone; and the tail portion comprising a tool receiver at its tail end to selectably, fixedly engage the tool.

19. The system of claim 17, the motor component operably engaged with the drive component to provide a hammering action between the first protrusion and the second protrusion when subjected to the magnetic field generated by the magnetic field generation component.

20. The system of claim 17, comprising an outer sleeve operably disposed in telescopic engagement with the outside of the insertion portion to operably provide a cover to the external screw threads of the first end of the drive component upon distraction.

* * * * *